(12) United States Patent
Gardner et al.

(10) Patent No.: US 6,841,376 B2
(45) Date of Patent: Jan. 11, 2005

(54) BISTABLE GENETIC TOGGLE SWITCH

(75) Inventors: Timothy Gardner, Jamaica Plain, MA (US); James J. Collins, Newton Center, MA (US)

(73) Assignee: Cellicon Technologies, Inc., Boston, MA (US)

(*) Notice: Subject to any disclaimer, the term of this patent is extended or adjusted under 35 U.S.C. 154(b) by 80 days.

(21) Appl. No.: 09/872,868

(22) Filed: May 1, 2001

(65) Prior Publication Data

US 2003/0166191 A1 Sep. 4, 2003

Related U.S. Application Data

(63) Continuation-in-part of application No. PCT/US99/28592, filed on Dec. 1, 1999.
(60) Provisional application No. 60/110,616, filed on Dec. 2, 1998.

(51) Int. Cl.[7] .......................... C12N 1/20; C12N 15/00; C12N 15/09; C12N 15/86; C07H 21/04
(52) U.S. Cl. ....................... 435/252.3; 435/325; 435/6; 435/320.1; 435/235.1; 435/455; 435/471; 435/440; 536/23.1; 536/24.1
(58) Field of Search ............................ 435/320.1, 69.1, 435/325, 440, 252.3, 471, 455, 6, 235.1; 536/23.1, 24.1

(56) References Cited

U.S. PATENT DOCUMENTS

| | | | |
|---|---|---|---|
| 4,833,080 A | | 5/1989 | Brent et al. |
| 5,416,008 A | * | 5/1995 | Bailey et al. |
| 5,589,392 A | | 12/1996 | Short |
| 5,814,618 A | | 9/1998 | Bujard et al. ................. 514/44 |
| 5,972,650 A | | 10/1999 | Yao |
| 5,989,910 A | | 11/1999 | Mermod et al. |

FOREIGN PATENT DOCUMENTS

| | | |
|---|---|---|
| EP | 0 136 907 A2 | 4/1985 |
| WO | WO 99/57290 | 11/1999 |
| WO | WO 00/23748 | 6/2000 |
| WO | WO 00/65080 | 11/2000 |

OTHER PUBLICATIONS

Amann et al., Vectors Bearing a Hybrid trp-lac Promoter Useful for Regulated Expression of Cloned Genes in *Escherichia coli*. (1983). *Gene* 25:167–178.

Amann et al., 'ATG Vectors' for Regulated High–Level Expression of Cloned Genes in *Escherichia coli*. (1985). *Gene* 40: 183–190.

Backman et al., Maximizing Gene Expression on a Plasmid Using Recombination in Vitro. (1978). *Cell* 13: 65–71.

Bailey et al., Molecular Genetics and Control Systems: Biochemical Engineering Fundamentals. Second Edition. Chapter 6: 307–372.

Chen et al., Molecular Design of Expression Systems: Comparison of Different Repressor Control Configurations Using Molecular Mechanism Models. (1991). *Biotechnology and Bioengineering* 38: 679–687.

(List continued on next page.)

*Primary Examiner*—Gerry Leffers
(74) *Attorney, Agent, or Firm*—Choate, Hall & Stewart

(57) ABSTRACT

Provided are methods and compositions for regulating gene expression in a cell. The invention provides recombinant genetic toggle switches which contain a first constitutive promoter-regulatory gene operon and a second constitutive promoter-regulatory gene operon. Expression of the regulatory gene from the first operon inhibits expression from the promoter in the second operon, and expression of the regulatory gene from the second operon inhibits expression from the promoter in the first operon. By use of the toggle switch and various switching agents it is possible to reversibly switch the expression of a gene of interest between a stable "on" state and stable "off" state or vice versa via transient exposure to a switching agent.

16 Claims, 17 Drawing Sheets

OTHER PUBLICATIONS

Chen et al., Construction and characterization of a novel cross–regulation system for regulating cloned gene expression in *Escherichia coli*. (1993) *Gene* 130:15–22.

Chen et al., Proces Characterization of a novel cross–regulation system for cloned protein production in *Escherichia coli*. (1995). *Biotechno. Prog.* 11(4): 397–402.

Cohen, Total Control: Now you can keep bugs in line with genetic clocks and switches. (2000). *New Scientist*.

Crowl et al., Versatile expression vectors for high–level synthesis of cloned gene products in *Escherichia Coli*. (1985) *Gene* 38: 31–38.

Dedhia et al., Design of expression systems for metabolic engineering: coordinated synthesis and degradation of glycogen. (1997). *Biotechnol & Bioeng.* 55 (2): 420–426.

Gardner et al., Construction of a genetic toggle switch in *Escherichia coli*. (2000). *Nature*. 403: 339–342.

Gardner et al., Neutralizing noise in gene networks. (2000) *Nature* 405: 520–521.

Gardner, Design and Construction of Synthetic Gene Regulatory Networks. (2000). *Ph.D. Dissertation, Boston University*.

Goeddel et al., Expression in *Escherichia coli* of Chemically Synthesized Genes for Human Insulin. (1979) *Proc. Natl. Acad. Sci. USA*, 76 (1): 106–110.

Gorman et al., Regulation of the Yeast Metallothionein Gene. (1986). *Gene*, 48: 13–22.

Hadcock et al., Cross–regulation between G–protein–mediated Pathways, Stimulation of Adenylyl Cyclase Increases Expression of the Inhibitory G–protein $G_{in2}$. (1990). *The Journal of Biological Chemistry* 265 (25): 14784–14790.

Hadcock et al., Cross–regulation between G–protein–mediated Pathways, Activation of the Inhibitory Pathway of Adenylylcyclase Increases the Expression of $\beta_2$ Adrenergic Receptors. (1991). *The Journal of Biological Chemistry* 266 (18): 11915–11922.

Hasty et al., Noise–based switches and amplifiers for gene expression. (2000). *Proc. Natl. Acad. Sci.USA.* 97(5): 2075–80.

Kaufman, High Level Production of Proteins in Mammalian Cells. (1987). *Genetic Engineering: Principles and Methods* 9: 155–198.

Kramer et al., Isolation of Yeast Genes with mRNA levels controlled by phosphate concentration. (1980). *Proc. Natl. Acad. Sci. USA*. vol. 77(11): 6541–6545.

Lee et al., Genetically Structured Models for lac Promoter–Operator Function in the Chromosome and in Multicopy Plasmids: lac Promoter Function. (1984) *Biotechnology and Bioengineering* XXVI: 1383–1389.

Lee et al., Genetically Structured Models for lac Promoter–Operator Function in the *Escherichia coli* Chromosome and in Multicopy Plasmids: lac Operator Function. (1984). *Biotechnology and Bioengineering* XXVI: 1372–1382.

Monod et al., General Conclusions: Teleonomic Mechanisms in Cellular Metabolism, Growth, and Differentiation. (1961). *Cold Spring Harbor Symposia on Quantitative Biology* XXVI: 389–401.

Moser et al., Characterization and Complementation of pMB1 Copy Number Mutant: Effect of RNA 1 Gene Dosage of Plasmid Copy Number and Incompatibility. (1983). *Journal of Bacteriology* 154 (2): 809–818.

Oshima, Regulatory Circuits for Gene Expression: The Metabolism of Galactose and Phosphate. (1982). *The Molecular Biology of the Yeast Saccharomyces: Metabolism and Gene Expression*: 159–180.

PCT International Search Report from PCT/US99/28592.

Platt, Regulation of Gene Expression in the Tryptophan Operon of *Escherichia coli*. (1975). *The Operon*: 263–302.

Ptashne, Repressor and Its Action. (1971). *The Bacteriophage Lambda* 11: 221–237.

Seo et al., Effects of Recombinant Plasmid Content on Growth Properties and Cloned Gene Product Formation in *Escherichia coli*. (1985). *Biotechnology and Bioengineering* XXVII: 1668–1674.

Shockett et al., Diverse strategies for tetracycline–regulated inducible gene expression. (1996). *Proc. Natl. Acad. Sci. USA*. 93: 5173–5176.

Sledziewski et al., Construction of Temperature–Regulated Yeast Promoters Using the MATα2 Repression System. (1988). *Biotechnology* 6:411–416.

Windass et al., The construction of a synthetic *Escherichia coli trp* promoter and its use in the expression of a synthetic interferon gene. (1982). *Nucleic Acids Research*. 10 (21): 6639–6657.

Cormack, B.P., et al., "*Facs–Optimized Mutants of the Green Fluorescent Protein (GFP)*" Gene, Elsevier Biomedical Press., Amsterdam, NL, vol. 173, 1996, pp. 33–38.

Gardner, Timothy, et al: "*A Theory for Controlling Cell Cycle Dynamics using a Reversibly Binding Inhibitor.*" Proceedings of the National Academy of Sciences of the United States, vol. 95, No. 24, Nov. 24, 1998, pp. 14190–14195.

Ishiura Masahiro, et al., "*Expression of a Gene Cluster kai ABC as a Circadian Feedback Process in Cyanobacteria*", Science (Washington, D.C., vol. 281, No. 5382, pp. 1519–1523.

Lutz, R., et al., "*Independent and Tight Regulation of Transcriptional Units in Escherichia coli Via the LACR/O, The TETR/O and ARAC/L1–L2 Regulatory Elements*", Nucleic Acids Research, Oxford University Press, Surry, GB, vol. 6, No. 25, 1997, pp. 1203–1210.

* cited by examiner

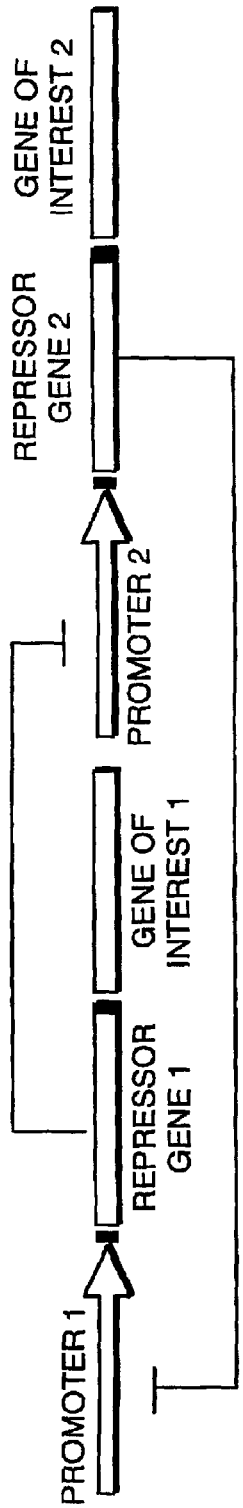
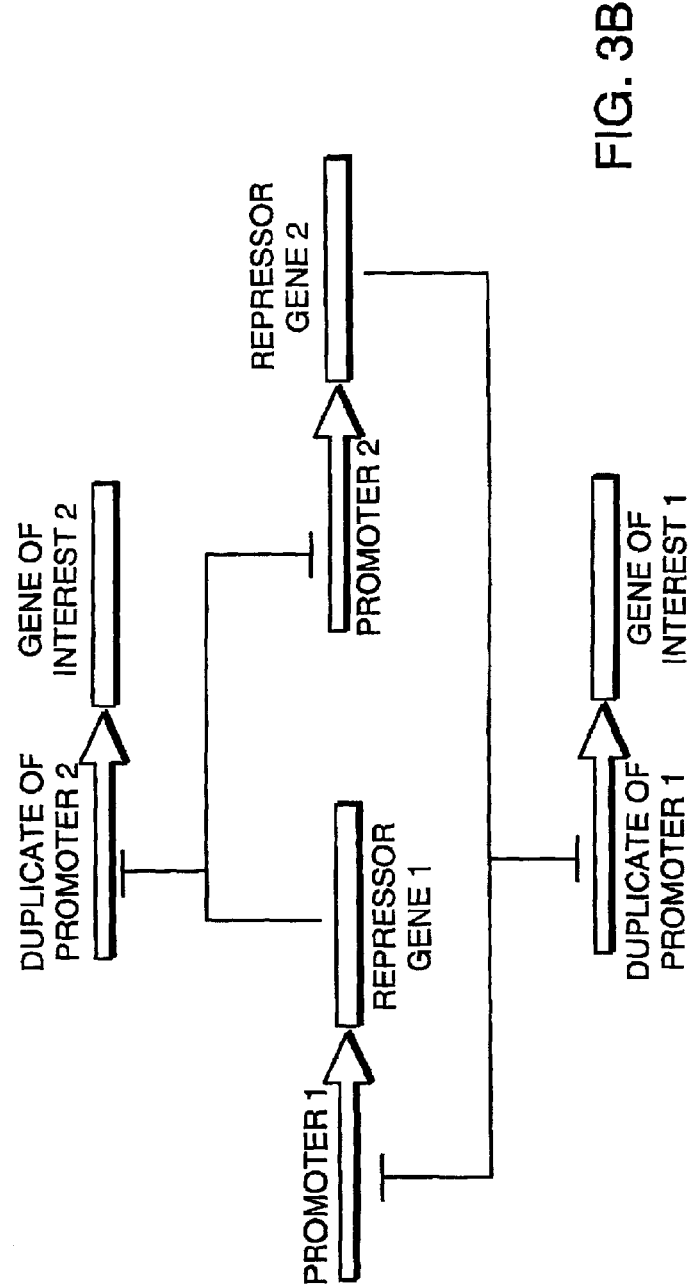
FIG. 3A
FIG. 3B

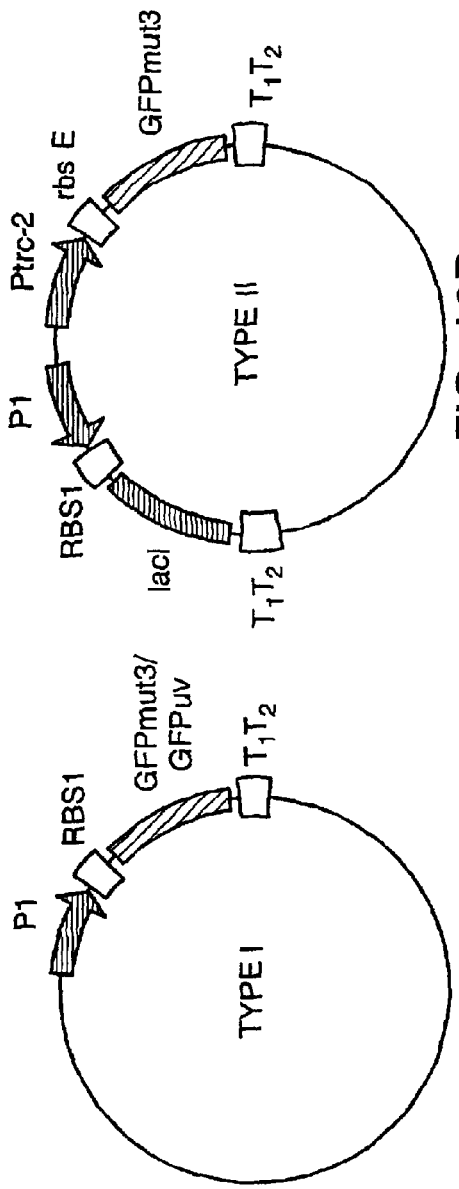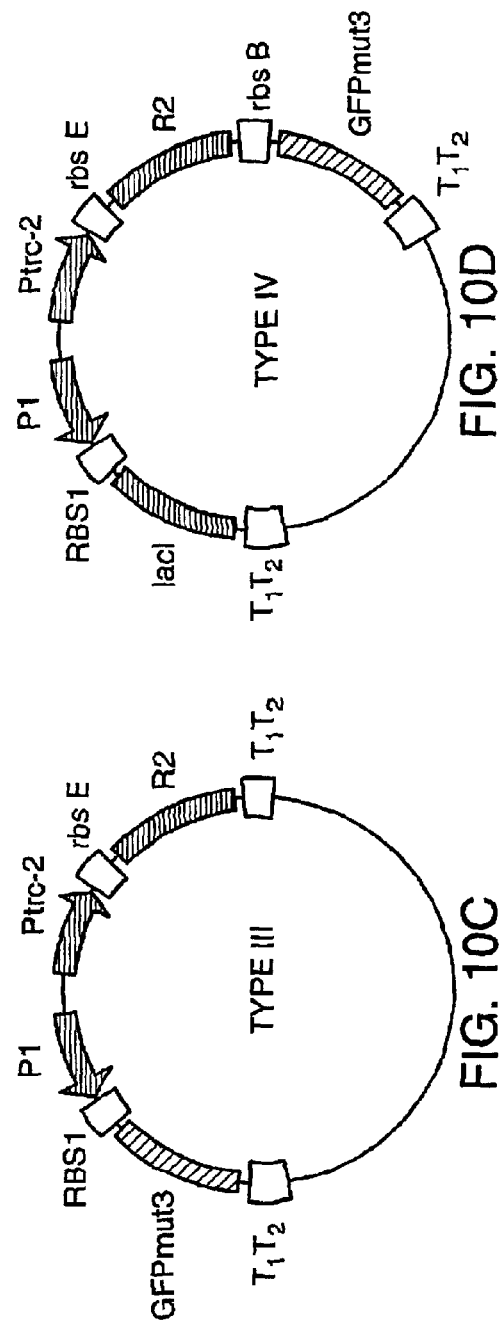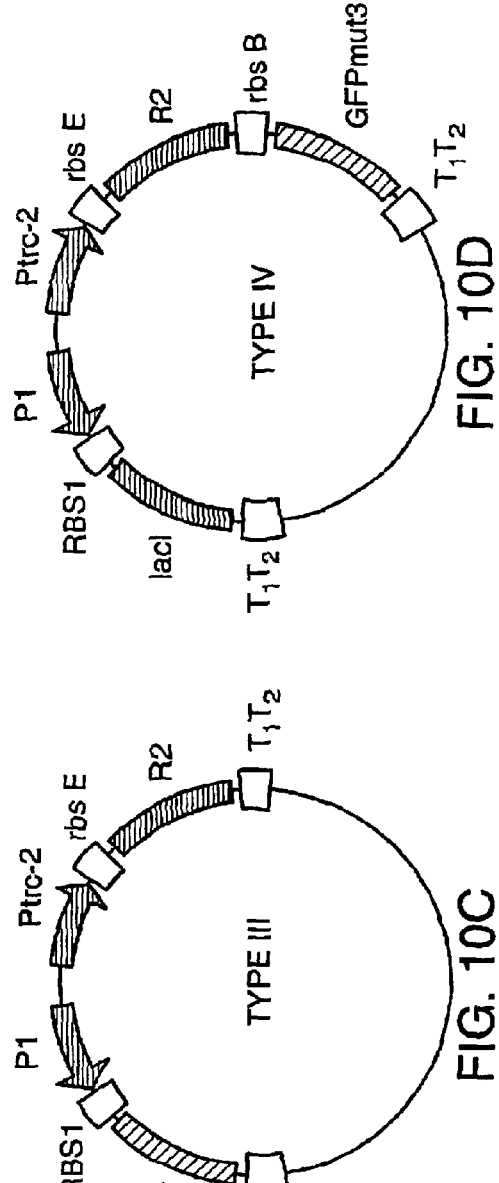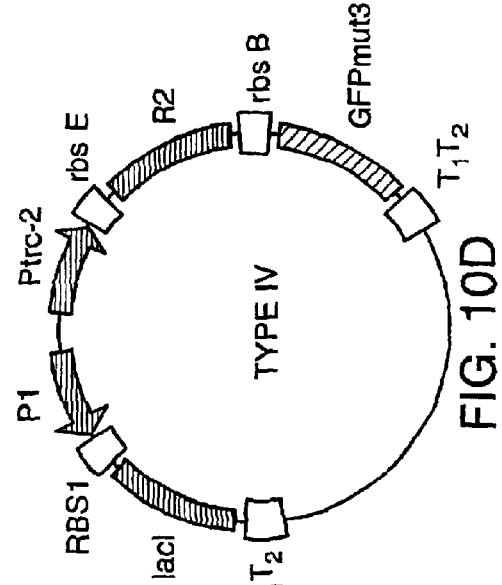
FIG. 10A TYPE I
FIG. 10B TYPE II
FIG. 10C TYPE III
FIG. 10D TYPE IV

| | | |
|---|---|---|
| A | AGGAGGAAAAAAATG | (SEQ ID NO: 4) |
| B | AGGAATTTAAATG | (SEQ ID NO: 5) |
| C | AGGAAACAGACCATG | (SEQ ID NO: 6) |
| D | AGGAAACCGGTTCGATG | (SEQ ID NO: 7) |
| E | AGGAAACCGGTTATG | (SEQ ID NO: 8) |
| F | AGGACGGTTCGATG | (SEQ ID NO: 9) |
| G | AGGAAAGGCCTCGATG | (SEQ ID NO: 10) |
| H | AGGACGGCCGGATG | (SEQ ID NO: 11) |

FIG. 11b

BISTABLE GENETIC TOGGLE SWITCH

RELATED APPLICATIONS

This application claims priority to, and is a CIP of PCT/US99/28592, filed on Dec. 1, 1999, which claims priority to, and the benefit of U.S. Ser. No. 60/110,616, filed on Dec. 2, 1998, the disclosures of which are incorporated by reference herein. Related applications include: U.S. Ser. No. 09/872,339, filed Jun. 1, 2001 now U.S. Pat. No. 06,737,269 and U.S. Ser. No. 09/872,338, filed Jun. 1, 2001 incorporated by reference herein.

GOVERNMENT SUPPORT

Work described herein was supported, in part, by Office of Naval Research Grant N00014-99-1-0554. The U.S. Government has certain rights in the invention.

FIELD OF THE INVENTION

The present invention relates generally to methods and compositions for regulating gene expression in a cell. In particular, the invention provides genetic toggle switch constructs that can switch the expression of one or more genes between a stable "on" state and a stable "off" state or vice versa in response to a transient stimulus.

BACKGROUND OF THE INVENTION

Many areas of biotechnology involve regulating the expression of one or more genes of interest by applying an external agent. Typical approaches for regulating gene expression involve natural or engineered transcription factors that activate or inhibit expression of a specific gene in response to a chemical agent [Gossen and Bujard, Proc. Natl. Acad. Sci. USA, 89:5547, 1992; Rivera, et al., Nat. Med., 2:1028, 1996; Yao and Evans, Proc. Natl. Acad. Sci. USA, 93:3346, 1996; Wang, et al., Proc. Natl. Acad. Sci. USA, 91:8180, 1994]. Transcription factors often are introduced into a cell using DNA constructs that express a transcription factor and a gene of interest.

Stable activation or inhibition of a transcription factor typically requires a continuous application of a chemical agent. For example, continuous activation of a LacI-repressible promoter typically requires the continuous presence of the chemical agent isopropyl β-D-thiogalactopyranoside (IPTG). However, continuous application of a chemical agent is often undesirable because it can have confounding or deleterious effects on the cell or tissue to which it is applied. In addition, the amount of chemical required for continuous application can be very costly, especially when a large volume of cell culture is involved. Therefore, there is a need in the art for methods and compositions for regulating the expression of a gene of interest without the continuous application of one or more stimulating agents.

SUMMARY OF THE INVENTION

The invention provides methods and compositions useful for switching gene expression between two different stable expression states. According to the invention, the expression of one or more genes is changed from a first stable expression state to a second stable expression state by transient application of one stimulus, and from the second stable expression state back to the first stable expression state by transient application of another stimulus.

The recombinant bistable genetic toggle switch of the invention comprises two regulatory genes and two constitutive promoters. FIG. 1A shows a schematic representation of an co exemplary toggle switch of the invention. The toggle switches comprise two regulatory genes ($R_1$ and $R_2$) under the control of their own promoters ($P_1$ and $P_2$, respectively), wherein the expression of one regulatory gene influences the expression of the other regulatory gene. The two regulatory gene-promoter pairs, i.e., $P_1$–$R_1$ and $P_2$–$R_2$, may be defined by one contiguous nucleic acid sequence or a plurality of separate of nucleic acid sequences. A product of the first regulatory gene inhibits or reduces (represses) expression of the second regulatory gene. This inhibition or reduction is removed by application of a switching agent ($SA_2$). A product of the second regulatory gene inhibits or reduces (represses) expression of the first regulatory gene. This inhibition or reduction (depression) is removed by application of another switching agent ($SA_1$). According to preferred embodiments, either regulatory gene can be expressed, however, both preferably are not expressed simultaneously.

The bistable genetic toggle switch has two stable, alternative expression states. In a first state, a first promoter is active and a second promoter is substantially inactive. In a second state, the first promoter is substantially inactive and the second promoter is active. Therefore, in the first stable state, genes that are transcribed from the first promoter are expressed. Alternatively, in the second stable state, genes that are transcribed from the second promoter are expressed. According to the invention, a transient stimulus or switching agent can switch gene expression from the first state to the second state or from the second state to the first state. Preferably, switching between the first state and the second state does not occur in the absence of the switching agent. Accordingly, preferred constructs are bistable in that they can exist in either of two stable expression states, and transient exposure to a switching agent is required to switch from one expression state to another.

An important feature for the stability of each expression state is that the first regulatory gene product being expressed has a stable inhibitory effect on expression of the second regulatory gene product. This inhibitory effect can be overcome by an appropriate stimulus (switching agent) that allows expression of the second regulatory gene product. Expression of the second regulatory gene product switches off the expression of the first gene product and establishes a new stable expression state. Once established, this new expression state is stable and does not require further exposure to the switching agent.

In preferred embodiments of the invention, both regulatory gene products are balanced such that each regulatory gene product has a similar inhibitory effect on expression of the other regulatory gene product. According to the invention, a balanced inhibitory effect is preferred for the creation of two alternative stable expression states and efficient transient stimulus-induced switching between the alternative expression states.

According to the invention, the switching agent can exert its effect at the level of gene expression (transcription and/or translation) and/or at the functional level of the regulatory gene product. Accordingly, the switching agent may interfere with expression of the regulatory gene product by affecting transcription, RNA stability, translation, protein stability, post translational modification, or a combination of the above. Alternatively, the switching agent may act by affecting the functional activity of the regulatory gene product (for example, an inducer may interfere with the repression activity of a repressor protein).

The toggle switch may be coupled to a gene of interest such that switching between stable expression states regulates the expression of that gene of interest. For example, transient exposure to one switching agent can activate expression of a gene of interest, while transient exposure to a second, distinct switching agent can inactivate expression of the same gene of interest. Accordingly, expression of a gene of interest can be linked to the expression of either one of the regulatory genes in the toggle switch. In a preferred embodiment, the gene of interest is transcribed from the same promoter that is coupled to the regulatory gene such that the gene of interest and the regulatory gene are transcribed as a single transcript. In an alternative embodiment, the gene of interest can be transcribed from a separate promoter that is (i) identical to that which is coupled to the regulatory gene, or (ii) regulated by the same gene product, either directly or indirectly, as that which regulates the promoter coupled to the regulatory gene.

In another embodiment, one or more genes of interest are regulated by the expression of each of the regulatory genes. Accordingly, a first switching agent switches "on" stable expression of a first gene of interest and/or switches "off" expression of a second gene of interest. A second switching agent switches "on" stable expression of a second gene of interest and/or switches "off" expression of a first gene of interest.

BRIEF DESCRIPTION OF THE DRAWINGS

FIGS. 3A and 3B are schematic representations showing two exemplary configurations for regulating expression of genes of interest. The genes of interest are shown in a polycistronic configuration (FIG. 3A) or in a co-regulation configuration (FIG. 3B).

FIGS. 10A-D are schematic representations of four plasmids used in the construction of an exemplary toggle switch.

FIGS. 11A-B are schematic representation showing the nucleic acid sequence of promoters (FIG. 11A) and ribosome binding sites (FIG. 11B) used to construct toggle plasmids of the invention.

FIG. 12A shows Class 1 toggle switches (pTAK) and controls; and FIG. 12B shows Class 2 toggle switches (pIKE) and controls. FIG. 12C shows a long-term test of pTAK117 bistability, wherein cells were initially divided, diluted and induced with IPTG for 6 hours (circles) or grown without inducer (squares).

FIG. 14A shows a steady-state gene expression after 17 hour induction; FIG. 14B shows a fraction of toggle cells in the high state at various concentrations of IPTG; and FIG. 14C shows scatter plots (left plots) and histograms (right plots) illustrating the condition of the toggle cells at points 2, 3 and 4 (of FIG. 14A) near the bifurcation point.

DESCRIPTION OF THE INVENTION

The invention provides methods and compositions that extend the functionality of synthetic gene regulatory systems beyond that of currently available systems. Specifically, the invention provides bistable gene regulatory systems that have at least two stable states of gene expression. Transient exposure to a switching means can be used to switch a gene regulatory system of the invention between two alternative stable expression states. Preferably, transient exposure to a switching agent is used to switch the gene regulatory system from one stable state to another stable state. Furthermore, transient exposure to a second switching agent can be used to switch the gene regulatory system back to its original state. In other words, transient exposure to switching agents can be used to reversibly switch the regulatory system between its two stable states. Methods and compositions of the invention are useful for the stable regulation of gene expression, for example, in gene therapy, tissue engineering, biotechnology, and biocomputing.

Figure 1A:
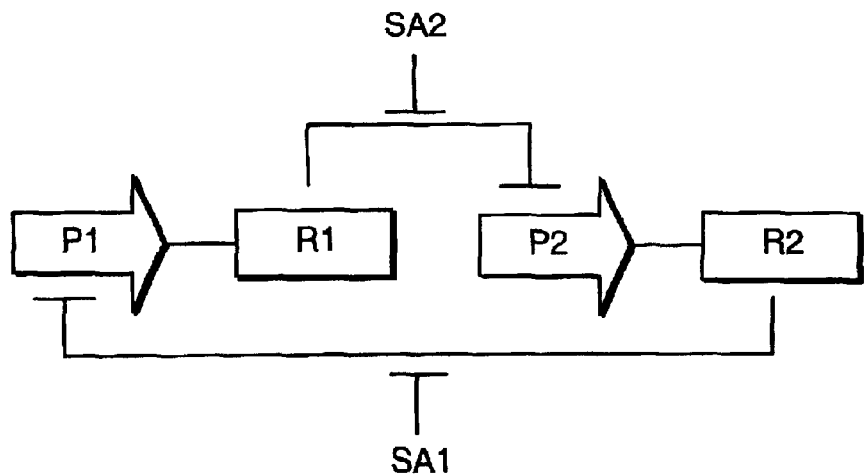
FIGS. 1A and 1B are schematic representations of a preferred genetic toggle switch of the invention.

FIG. 1A is a schematic representation of a recombinant bistable genetic system of the invention that is characterized by two alternative stable states of gene expression. The bistable switch comprises (i) a first nucleic acid (for example, DNA or RNA) construct comprising a first constitutive promoter ($P_1$) in operable association with a first regulatory gene ($R_1$) encoding, for example, a first repressor protein, and (ii) a second nucleic acid (for example, DNA or RNA) construct comprising a second constitutive promoter P2) in operable association with a second regulatory gene ($R_2$), for example a second repressor protein. In this system, $R_1$, when produced, represses the activity of the second constitutive promoter, and $R_2$, when produced, represses the activity of the first constitutive promoter. This system provides a genetic toggle switch that is active either in one state, for example, where RI is being produced, or in another state, for example, where $R_2$ is being produced. An exemplary system is shown in more detail in FIG. 1B.

Figure 1B:
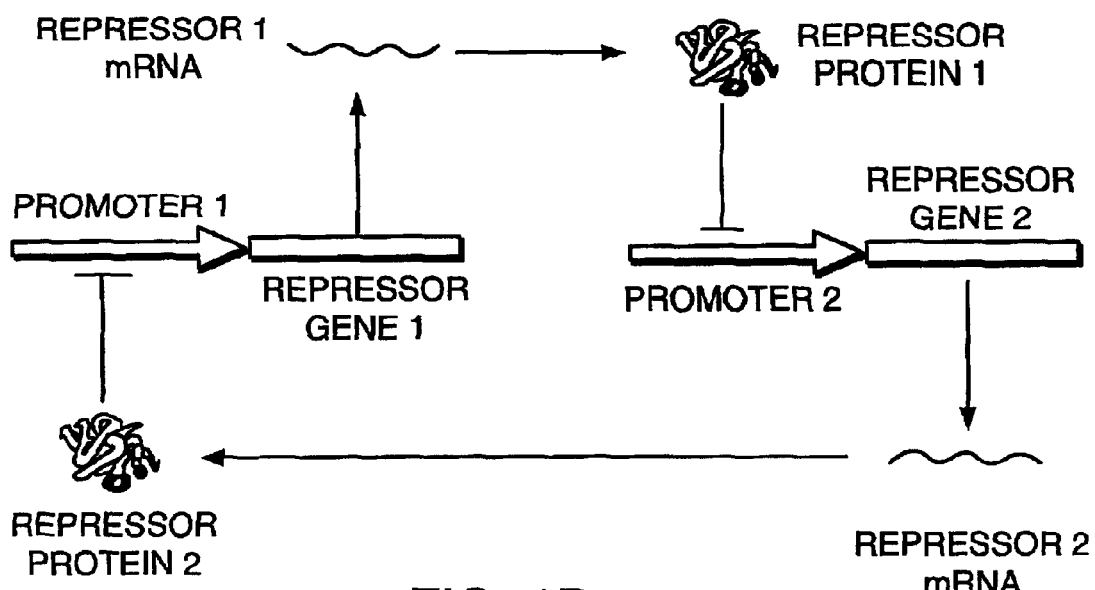

In FIG. 1B, a preferred bistable genetic toggle system includes a first constitutive promoter (promoter 1) that promotes transcription of a first regulatory gene (repressor gene 1), and a second constitutive promoter (promoter 2) that promotes transcription of a second regulatory gene (repressor gene 2). Transcription of the repressor gene 1 produces repressor 1 mRNA, which when translated produces repressor protein 1. Repressor protein 1 inhibits transcription from promoter 2. In contrast, transcription of repressor gene 2 produces repressor 2 mRNA, which when translated produces repressor protein 2. Repressor protein 2 inhibits transcription from promoter 1. In other words, the gene product of the first regulatory gene inhibits transcription from the second promoter, and the gene product from the second promoter inhibits transcription from the first promoter.

Figure 2:
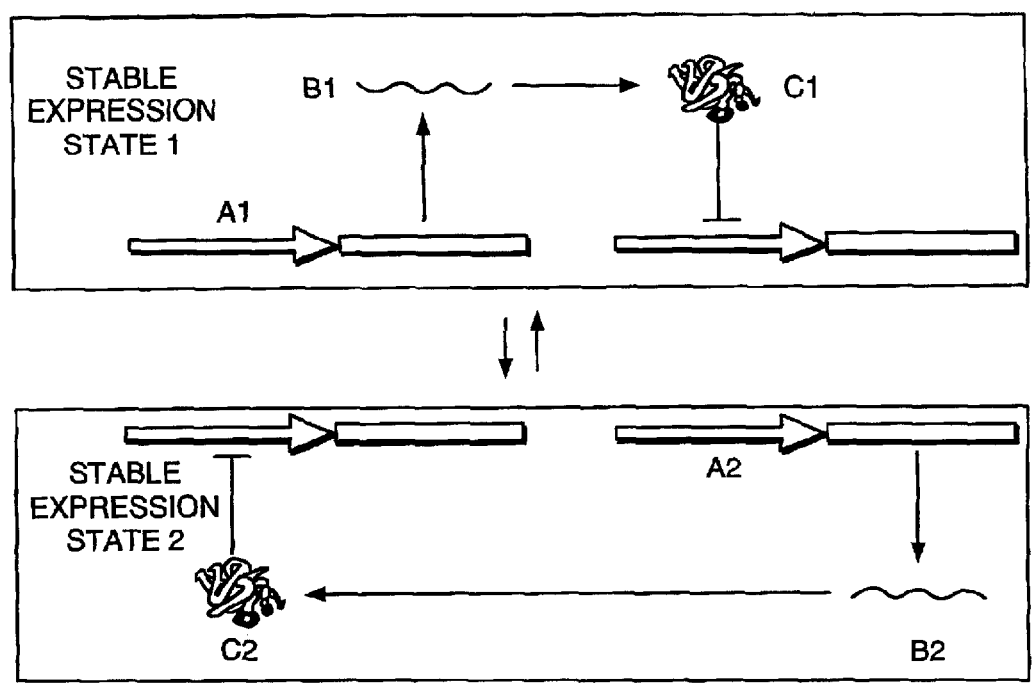
FIG. 2 is a schematic representation showing the two stable expression states of a bistable genetic switch of the invention.

The genetic toggle can exist in either of two stable states (FIG. 2) in which one of the regulatory genes is expressed and active. The genetic toggle switch can be switched from a first stable state expressing a first regulatory gene to a second stable state expressing a second regulatory gene by the transient application of a switching agent that inhibits expression or activity of the first regulatory gene. This inhibition may occur at a transcriptional level (A1), a translational level (B1) or a functional level (C1). Inhibition of the first regulatory gene product by the switching agent allows expression of the second regulatory gene from its promoter. The second regulatory gene product further inhibits the first regulatory gene product by inhibiting its expression. The second regulatory gene product eventually reaches a level of expression that prevents expression of the first regulatory gene and, therefore, inhibits the first regulatory gene product in the absence of the switching agent. At this point, the toggle switch is in a second, stable state of gene expression, and the switching agent is no longer required. The bistable toggle switch of the invention can then be switched back to the first stable state by transient application of a different switching agent that inhibits the expression or activity of the second regulatory gene product. This inhibition may occur at a transcriptional level (A2), a translational level (B2) or a functional level (C2). As described above for the establishment of the second state, the first state is reestablished and is stable even after removal of the switching agent.

According to the invention, the switch from one stable state to another stable state is reversible, and can be repeated using the appropriate switching agents. It is contemplated that the switch may be switched from one state to the other state at least 5 times, more preferably at least 10 times, more preferably at least 100 times and most preferably an indefinite number of times. In preferred embodiments of the invention, the switch from one state to another state does not occur in the absence of a switching agent. In order to prevent switching in the absence of such an agent, the inhibitory properties of each regulatory gene must be sufficiently strong to prevent expression of the other inhibitory gene from establishing itself. If a first regulatory gene is not sufficient to prevent expression of a second regulatory gene from establishing itself in the absence of a switching agent, the system is monostable and will return to default expression of the second regulatory gene in the absence of the agent.

According to the invention, the inhibitory properties of a regulatory gene depend on the expression level of the gene product and the inherent inhibitory activity of the gene product. In turn, the expression level of a gene product is a function of transcription, RNA stability, translation (if the gene product is a protein), and protein stability (if the gene product is a protein). In a preferred bistable switch of the invention, the inhibitory strength of the first and second regulatory gene products are balanced such that the inhibitory strength of the first regulatory gene product is the same as that of the second regulatory gene product. The inhibitory strengths of the two regulatory gene products can be balanced by modifying their expression levels and functional activity. Accordingly, a regulatory gene product that has a high functional activity can be balanced with a regulatory gene product that has a lower functional activity that is expressed at a higher level. While a first regulatory protein with high functional activity can be expressed at a lower level, it is important that the low level of expression be sufficiently stable to maintain constant inhibition of the second regulatory protein. If not, the system will not be bistable.

In a preferred embodiment, a regulatory gene encodes a molecule that inhibits gene expression in a cooperative fashion. A cooperative regulatory molecule of the invention is characterized by an inhibition saturation curve that is non-hyperbolic, and preferably is sigmoidal. Accordingly, for a regulatory molecule that inhibits transcription by binding to a target DNA sequence, the inhibition is cooperative when the binding of a first molecule to a first target DNA increases the affinity a second molecule for a second target DNA.

1. Toggle Switch Components

A preferred bistable genetic toggle switch comprises at least two constitutive promoters, each of which is operably linked to a gene encoding a repressor of gene expression. Both of the promoter-repressor pairs may be present in a single contiguous nucleic acid or may be present in separate nucleic acid sequences. A preferred repressor represses gene expression by inhibiting or reducing transcription. Alternatively, a repressor may repress gene expression by inhibiting translation, including translation initiation and/or message stability, or a combination of the above. According to the invention, gene expression in a genetic toggle switch can be inhibited by a repressor means. A repressor of gene expression is preferably a repressor protein. Alternatively, one or both repressors of a genetic toggle switch are repressor nucleic acid molecules.

Depending on whether the genetic toggle switch is intended to function in a prokaryotic or a eukaryotic organism, each promoter may be any prokaryotic promoter, preferably a constitutive promoter, including, for example, the $P_{trc}$, Plac, $P_L$, Pr, Prm, and $P_{ltet}$ promoters. Alternatively, one or both promoters may be any eukaryotic promoter, preferably a constitutive promoter, including promoters that are constitutive only in specific cell or tissue types, including, for example, the CMV, SV40, HSV-tk, RSV-LTR, β-actin, keratin 6, and EF-1α promoters. The promoters may naturally include or may be modified to include an operator sequence that binds specifically to a double stranded DNA (dsDNA) binding protein encoded by one of the regulatory genes in the toggle switch. According to the invention, an operator is a nucleic acid to which a regulatory protein binds to exert its regulatory effect on gene expression. One or more operator sequences may be positioned upstream, downstream and/or within a promoter of the invention. An operator preferably is associated with a constitutive promoter. According to the invention, a promoter is constitutive if it directs a minimal basal level of gene expression that is sufficient to repress the expression of another promoter in the context of a genetic toggle switch. Accordingly, a constitutive promoter can be activated by an inducer, but remains functional in the absence of the inducer. Useful promoters include naturally occurring promoters and modified promoters. Examples of modified constitutive promoters are described, for example, in PCT/US00/11091, PCT/US98/10907, and U.S. Pat. No. 4,833,080. Furthermore, the constitutive promoter may be modified to include a switching sequence that binds specifically to an inhibitory compound, for example, an inhibitory compound capable of switching the genetic toggle switch between states. One or more switching sequences may be positioned upstream, downstream and/or within the constitutive promoter. According to the invention, constitutive promoters also include tissue specific promoters and response specific promoters, provided that they are functional in specific tissues or under specific conditions.

In a preferred embodiment, the regulatory proteins encoded by the first and second regulatory genes (for example, "repressor gene 1" or "repressor gene 2" of FIG. 1B) must each be capable of inhibiting transcription from one of the two constitutive promoters by binding selectively to the operator sequence adjacent to or within the promoter sequence itself. The repressor genes may be cloned from prokaryotic or eukaryotic organisms or they may be designed using protein engineering methods. Examples of such dsDNA binding proteins include NF-KB, TetR, LacI, Pip. Additional repressor genes may be identified through a variety of approaches including, for example, i) text or homology-based searches of gene databases, ii) traditional or high-throughput biochemical screening (including DNA footprinting, gel-shift assays, ELISA assays, microarray-based assays, flow-cytometry, and immunochemical assays), iii) random mutagenesis and screening for sequence-specific dsDNA binding properties (including phage-display and ribosome display), (iv) rational design using physical, thermodynamic, statistical, bioinformatic and computational theories and methods, and (v) a combination of these approaches.

A repressor gene may also be modified to enhance the ability of the encoded protein to inhibit transcription. Such modifications include fusing the repressor domain of a naturally occurring transcriptional regulator to a dsDNA binding protein. Examples of such repressor domains include: a v-erbA oncogene product repressor domain; a Drosophila Krueppel protein repressor domain; a KRAB domain of the kox1 gene family; S. cerevisiae Ssn6/Tup1 protein complex; yeast SIRI protein and NePI, and have been used in previous work to enhance the inhibition of transcription by dsDNA binding proteins [Fussenegger, et al., Nature Biotechnol., 18:1203, 2000; PCT/US00/1109]. Additional repressor domains may be identified through text or homology-based searches of gene databases or through biochemical screening and analysis.

The toggle switches of the invention may be used to express one or more genes of interest. It is contemplated that a variety of configurations may be used in the practice of the invention. For example, FIG. 3(A) shows a toggle switch comprising two genes of interest, each being under the control of a different promoter. In this configuration, each promoter, repressor gene and gene of interest is encoded by a single nucleic acid sequence (polycistronic configuration). However, it is contemplated that the elements need not be disposed within a single sequence.

In FIG. 3(B), the toggle switch comprises four separate elements in a co-regulatory configuration, namely, (i) a repressor gene 1 in operative association with constitutive promoter 1, (ii) a repressor gene 2 in a operative association with constitutive promoter 2, (iii) gene of interest 1 in operative association with a duplicate copy of promoter 1, and (iv) gene of interest 2 in operative association with a duplicate copy of promoter 2. During operation, the product of repressor gene 1 can repress both the expression of repressor gene 2 and gene of interest 2. Furthermore, the product of repressor gene 2 can repress both the expression of repressor gene 1 and gene of interest 1. It is contemplated, however, that any one of a variety of configurations, for example, a combination of the polycistronic and co-regulatory configurations, may be used to produce toggle switches of the invention.

2. Switching Agents

According to the invention, a switching agent causes a bistable genetic toggle switch to flip from one stable state to another stable state by interfering with one of the regulatory gene products. The switching agent can interfere with a regulatory gene product at different levels. For example, the agent can directly reduce the functional activity of the regulatory gene product. Alternatively, or in addition, the agent can reduce the expression of the regulatory gene product by affecting transcription of the regulatory gene, RNA stability, translation, protein stability, post translational modification or a combination of the above.

A switching agent can be a natural or synthetic molecule, for example, a protein or nucleic acid, peptide nucleic acid or small molecule, for example, a small organic or inorganic molecule. Alternatively, an agent can be a physical property, for example, temperature, light, osmotic pressure, pH, or membrane potential.

According to preferred embodiments of the invention, two different agents are used to switch the bistable toggle between "on" and "off" states. A first agent acts to switch the toggle switch into a first stable state. A second, different agent acts to switch the toggle switch into second stable state. The different agents preferably are independently chosen from natural and synthetic molecules, and physical conditions.

Figure 4:
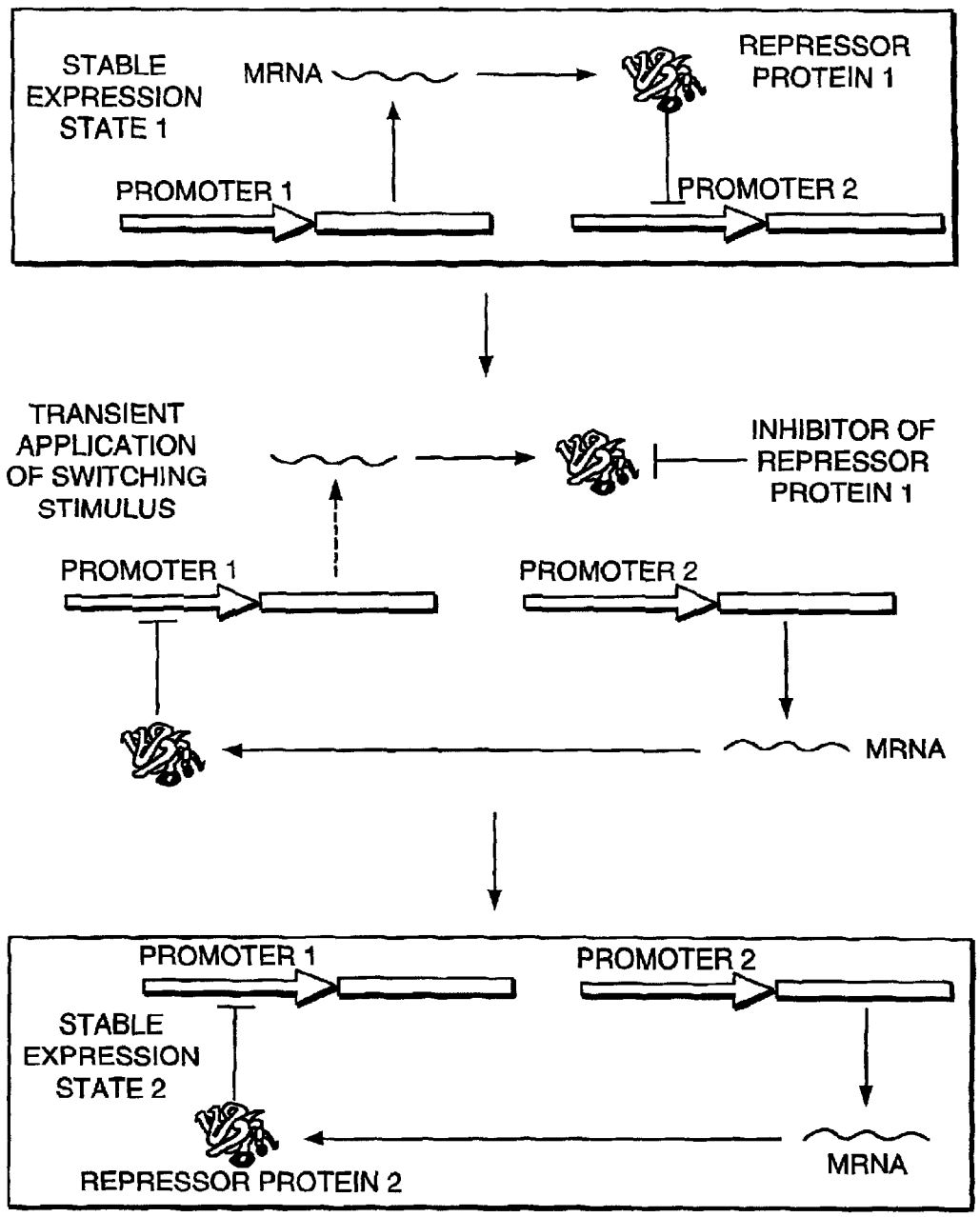
FIG. 4 is a schematic representation illustrating switching from a first expression state to a second expression state upon application of a transient stimulus (inhibitor of repressor protein activity).

FIG. 4 shows the transition of an exemplary switch from a first stable expression state (Expression State 1) to a second stable expression state (Expression State 2). In the first stable o expression state, the repressor protein 1 is capable of inhibiting or reducing transcription from promoter 2. However, upon application of the switching agent, the repressor activity of repressor protein 1 is inhibited. As a result, promoter 2 expresses repressor protein 2 which in turn inhibits transcription from promoter 1.

As discussed in more detail below, the switching agent may exert its effect by one or more of the following modes of action.

A—Switching Agent Mediated Decrease in Regulatory Gene Product Activity

A switching agent may reduce the activity or function of a regulatory gene product. For example, when the regulatory gene product is a repressor, the switching agent may be an inducer, for example, a chemical or physical agent, that interacts with the repressor to prevent it, or reduce its ability to bind to the cognate operator.

Figure 5:
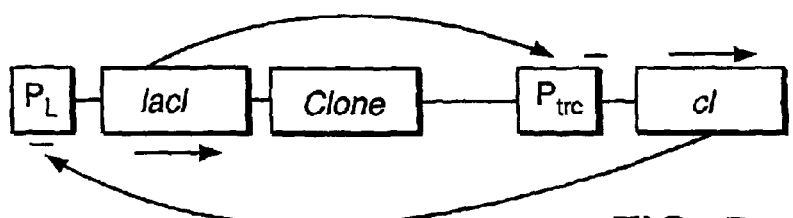
FIG. 5 is a schematic representation of an exemplary toggle switch construct

By way of example, the toggle switch in FIG. 5 comprises two operons, one containing $P_L$ promoter—lacI repressor—gene of interest (Clone) and the other containing $P_{trc}$ promoter—cI repressor. The switch from expression via the $P_L$ promoter to expression via the $P_{trc}$ is induced by the addition of IPTG which binds to the lacI repressor protein and reduces its ability to repress the $P_{trc}$ promoter.

The lacI-Clone genes are under the transcriptional control of the $P_L$ promoter (which is derived from bacteriophage λ), and the cI gene is under the control of the $P_{trc}$ promoter (which is a fusion of promoters derived from the Lac operon and the tryptophan operon). In this embodiment, the lacI repressor protein represses transcription by the $P_{trc}$ promoter while the cI repressor protein represses transcription by the $P_L$ promoter. If the system is initially expressing the lacI-Clone, then transient application of IPTG results in the formation of an IPTG-lacI complex. As a result of complex formation, the lacI repressor loses or reduces its ability to repress the $P_{trc}$ promoter. Accordingly, the addition of IPTG results in an increase in the levels of expressed cI repressor and consequently a decrease in the transcription activity of the $P_L$ promoter which, in turn, causes a decrease in lacI repressor levels. As a result, the construct switches the expression of the cI gene "on" and the lacI-Clone genes "off," even after the removal of IPTG.

B—Switching Agent Mediated Decrease in Regulatory Gene Transcription

In an embodiment of the invention where the regulatory gene products are protein repressors of gene transcription, a variety of biochemical compounds can uniquely inhibit the transcription of one of the repressor genes by binding to the dsDNA of the constitutive promoter in operative association with the repressor gene, or to switching sequences positioned upstream, downstream or within the promoter, in a sequence-specific manner. In general, an agent can inactivate a regulatory gene product by binding to dsDNA and inhibiting transcription. Useful molecules that exhibit this dsDNA binding activity include, for example, i) nucleic acids that form a triple helix with dsDNA, ii) small-molecule compounds that bind specific dsDNA sequences, and iii) dsDNA binding proteins.

Nucleic acids, including DNA and RNA oligonucleotides, and chemically modified variants of RNA and DNA oligonucleotides, are capable of binding to the major groove of the double-stranded DNA helix. Triplex-forming nucleic acids bind specifically and stably, under physiological conditions, typically to homopurine stretches of dsDNA. Chemical modifications of triplex-forming nucleic acids, such as the coupling of intercalating compounds to the nucleic acid or the substitution of a natural base with a synthetic base analogue, can increase the stability of the triplex DNA. The formation of triplex DNA by triplex-forming nucleic acids can inhibit the initiation or elongation of transcription by RNA polymerase proteins. The design of triplex-helix forming nucleic acids and their use in the regulation of gene expression is described, for example, in Gowers & Fox, Nucleic Acids Res., 27:1569, 1999; Praseuth, et al., Biochim. Biophys. Acta, 1489:181, 1999; Kochetkova & Shannon, Methods Mol. Biol., 130:189, 2000; Sun, et al., Curr. Opin. Struct. Biol., 6:327, 1996.

A variety of natural and synthetic chemical compounds have been demonstrated to bind to specific dsDNA sequences. The compounds, which act by a variety of mechanisms, include netropsin and distamycin [Coll, et al., Proc. Natl. Acad. Sci. USA, 84:8385, 1987], Hoechst 33258 [Pjura, et al., J Mol. Biol., 197:257, 1987], pentamidine [Edwards, et al., Biochem., 31:7104, 1992], and peptide nucleic acid [Nielsen, in Advances in DNA Sequence-Specific Agents, (London, JAI Press), pp. 267–78, 1998]. Rational modification [Baily, in Advances in DNA Sequence-Specific Agents, (London, JAI Press), pp. 97–156, 1998; Haq and Ladbury, J Mol. Recog., 13:188, 2000] and combinatorial chemistry [Myers, Curr. Opin. Biotech., 8:701, 1997] can be used to modify the sequence specificity and binding characteristics of these compounds. The binding of such compounds to dsDNA can inhibit the initiation of transcription or elongation of mRNA transcripts by RNA polymerase proteins.

A large number of proteins exist naturally that are capable of binding to specific dsDNA sequences. These proteins typically utilize one of several dsDNA binding motifs including, for example, a helix-turn-helix motif, a zinc finger motif, a C2 motif, a leucine zipper motif, or a helix-loophelix motif. The binding of such proteins to dsDNA can inhibit the initiation of transcription or elongation of mRNA transcripts by RNA polymerase proteins. Improved understanding of the principles of DNA sequence recognition by these proteins has permitted rational modification of their sequence-specificity. The design of dsDNA binding proteins and the use of dsDNA binding proteins in the regulation of gene expression is described, for example, in Vinson, et al., Genes Dev., 7:1047, 1993; Cuenoud and Schepartz, Proc. Natl. Acad. Sci. USA, 90:1154, 1993; Park, et al., Proc Natl. Acad. Sci USA, 89:9094, 1992; O'Neil, Science, 249:774, 1990; Wang, et al., Proc. Natl. Acad. Sci. USA, 96:9568, 1999; Berg, Nature Biotech., 15:323, 1997; Greisman, Science, 275:657, 1997; Beerli, Proc. Natl. Acad. Sci. USA, 97:1495, 2000; Kang, J. Biol. Chem., 275:8742, 2000.

C—Switching Agent Mediated Decrease in Regulatory Gene Translation

In an embodiment of the invention where the regulatory gene products are protein repressors of gene transcription, a variety of biochemical compounds can selectively inhibit the translation of mRNA encoding one of the repressor genes. The agent can accomplish this effect by one or more of several available mechanisms, including binding to the mRNA sequence, or binding to and catalyzing the cleavage of the mRNA sequence in a sequence-specific manner. Molecules that are useful to inhibit translation include (i) full and partial length antisense RNA transcripts, (ii) antisense RNA and DNA oligonucleotides, and peptide nucleic acids, (iii) RNA and DNA enzymes, and (iv) sequence-specific RNA-binding chemical compounds.

Antisense RNA transcripts have a base sequence complementary to part or all of any other RNA transcript in the same cell. Such transcripts have been shown to modulate gene expression through a variety of mechanisms including the modulation of RNA splicing, the modulation of RNA transport and the modulation of the translation of mRNA [Denhardt, Annals N Y Acad. Sci., 660:70, 1992, Nellen, Trends Biochem. Sci., 18:419, 1993; Baker and Monia, Biochim. Biophys. Acta, 1489:3, 1999; Xu, et al., Gene Therapy, 7:438, 2000; French and Gerdes, Curr. Opin. Microbiol., 3:159, 2000; Terryn and Rouze, Trends Plant Sci., 5: 1360, 2000].

Antisense oligonucleotides can be synthesized with a base sequence complementary to a portion of (for example, 5–100 nucleotides, more preferably 10–50 nucleotides, and most preferably 12–20 nucleotides in length) any RNA transcript in the cell. Antisense oligonucleotides may modulate gene expression through a variety of mechanisms including modulation of RNA splicing, modulation of RNA transport and modulation of the translation of mRNA [Denhardt (1992), supra]. The properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C) [Wagner, Nat. Medicine, 1:1116, 1995; Varga, et al., Immun. Lett., 69:217, 1999; Neilsen, Curr. Opin. Biotech., 10:71, 1999; Woolf, Nucleic Acids Res., 18:1763, 1990].

Both RNA and DNA molecules have demonstrated the ability to accelerate the catalysis of certain chemical reactions such as nucleic acid polymerization, ligation and cleavage [Lilley, Curr. Opin. Struct. Biol., 9:330, 1999; Li and Breaker, Curr. Opin. Struct. Biol., 9:315, 1999; Sen and Geyer, Curr. Opin. Chem. Biol., 2:680, 1998; Breaker, Nature Biotech., 15:427, 1997; Couture, et al., Trends Genet., 12:510, 1996; Thompson, et al., Nature Medicine, 1:277, 1995; U.S. Pat. Nos.: 4,987,071; 5,712,128; 5,834,186; 5,773,260; 5,977,343; 6,022,962]. That is, RNA and DNA molecules can act as enzymes by folding into a catalytically active structure that is specified by the nucleotide sequence of the molecule. In particular, both RNA and DNA molecules have been shown to catalyze sequence-specific cleavage of RNA molecules. The cleavage site is determined by complementary pairing of nucleotides in the RNA or DNA enzyme with nucleotides in the target RNA. Thus, in principle, the RNA and DNA enzymes can be designed to cleave any RNA molecule [Usman, et al., Nucl. Acids Mol. Biol., 10:243, 1996; Usman, et al., Curr. Opin. Struct. Biol., 1:527, 1996; Sun, et al., Pharmacol. Rev., 52:325, 2000]. Hence, RNA and DNA enzymes can disrupt the translation of mRNA by binding to, and cleaving mRNA molecules at specific sequences.

Chemical compounds such as aminoglycoside antibiotics demonstrate the ability to bind to single-stranded RNA molecules with high affinity and some sequence-specificity [Schroeder, et al., EMBO J., 19:1, 2000]. Rational and combinatorial chemical modifications have been employed to increase the affinity and specificity of such RNA-binding compounds [Afshar, et al., Curr. Opin. Biotech., 10:59, 1999]. In particular, compounds may be selected that target the primary, secondary and tertiary structures of RNA molecules. Such compounds may modulate the expression of specific genes through a variety of mechanisms including disruption of RNA splicing or interference with translation. For example, high-throughput screening methods can lead to the identification of small molecule inhibitors of group I self-splicing introns [Mei, et al., Bioorg. Med. Chem., 5:1185,1997].

3. Toggle Switch Uses

A genetic toggle switch of the invention may be used to regulate the expression of any gene or genes of interest. This can be accomplished by (i) operably linking the genetic toggle switch DNA construct to the gene or genes of interest, (ii) transferring the resulting DNA construct into a host cell, and optimally (iii) transiently applying one switching agent to switch the genetic toggle switch into a first stable expression state (see FIG. 4) assuming that the gene of interest is expressed in the first expression state. Transient application of a different switching agent can then switch the genetic toggle switch into another state whereby expression of the gene interest is reduced or turned off.

A genetic toggle switch may be operably linked to a gene or genes of interest in two approaches. In one approach, (see FIG. 3A), each promoter of the genetic toggle switch transcribes a repressor gene and a gene of interest. The repressor gene and the gene of interest are each placed downstream of a signal that directs the initiation of translation of the coding sequence. In prokaryotic cells, the translation initiation signal may be a consensus ribosome binding signal followed by an ATG codon. In eukaryotic cells, the translation initiation signal depends on the position of the gene in the mRNA transcript. For the gene nearest to the 5' end of the transcript, the translation initiation signal may be the first ATG codon downstream of the 5' mRNA cap. Translation of this first gene in the transcript may be enhanced by introducing a Kozak consensus sequence around the ATG start codon. For genes downstream of the first gene, the translation initiation signal can be an internal ribosome entry site (IRES).

Alternatively, a gene of interest can be placed downstream of a second or duplicate copy of one of the constitutive promoters used in the toggle switch (see FIG. 3B) or downstream of an distinct promoter that is repressed by one of the repressors used in the toggle switch. The duplicate promoters and genes of interest may be placed in the same nucleic acid construct as the toggle, or in a different nucleic acid construct. In this approach, the repressor genes that are expressed by the genetic toggle switch co-regulate the duplicate promoters and their associated downstream genes.

The toggle switch constructs of the invention may be used in clinical applications such as gene therapy. For example, Rendahl et al. [Rendahl, K G et al. (1998) Nature Biotechnology 16:757–761] demonstrated a successful method for the delivery and controllable expression of a recombinant erythropoietin (epo) gene in mice. This work demonstrates the feasibility of regulating expression of the epo gene (which stimulates the production of red blood cells) in the treatment of hemoglobinopathies or anemia in humans. In Rendahl et al., the epo gene was placed under the control of a tetracycline controlled transcriptional activator. The presence of tetracycline interferes with gene expression by binding the transcriptional activator. Thus, the expression of the epo gene and the consequent production of red blood cells can be turned off by the administration of a certain threshold level of tetracycline. However, once the concentration of tetracycline fell below the threshold level, expression of the epo gene started once again.

While this approach appears promising, it suffers from the drawback that it requires sustained ingestion of tetracycline in order to maintain the epo gene in a suppressed state. Longterm ingestion of tetracycline may not be practical for a variety of reasons, such as side effects from longterm antibiotic administration, drug resistance, toxicity, inconvenience and expense. On the other hand, expression of epo gene (or any other transgene) under the control of the toggle switch constructs of the invention allows maintenance of gene expression in either the "on" or "off" state until the toggle is switched by the transient (rather than sustained) ingestion of the appropriate switching agent (e.g., tetracycline).

Toggle switch constructs may also be used to control cell cycle. For example, recent work has shown that a protein which reversibly binds any one of the cell-division cycle (CDC) proteins can modulate the frequency of cell division or stop and restart cell division completely [Gardner, T S. et al., (1998) Proc. Natl. Acad. Sci USA, 95: 14190–14195]. This scheme requires the controllable expression in vivo of the binding protein. The toggle switch construct is an ideal system for controlling expression of the binding protein. It can be turned "on" by transient administration of a switching agent that inhibits one of the toggle repressors, thus causing the cell cycle to stop or to change its frequency. The cell remains in this state until it is desired to restart the cell cycle or return it to its normal frequency. At such time, the toggle switch construct can be reversed again by transient application of a switching agent that inhibits the other repressor in the toggle. Control of cell division in this manner may, for example, be applied to control cell growth, improve the manufacture of engineered tissues, and to treat cancer.

Methods and compositions of the invention also are useful as sensors of endogenous or intracellular conditions. Some of the agents discussed above may be produced by the endogenous biochemical apparatus of a cell ("endogenous switching compounds"). RNA transcripts, for example, complementary to all or part of the mRNA transcript of the repressor genes in the genetic toggle switch, may be expressed from endogenous or transgenic promoter sequences. The DNA encoding such RNA transcripts may be endogenous to a cell, including RNAs transcribed from endogenous genes, or derived from artificial DNA constructs transferred into a cell, including viral vectors, expression plasmids and artificial chromosomes. Endogenous switching agents may cause a genetic toggle switch construct to switch from one stable expression state to the alternate stable expression state, for example, by inhibiting the transcription or translation of the active repressor gene. The expression state of a genetic toggle switch can be monitored by using one or more reporter genes for each expression state. For example, expression of a β-galactosidase. Thus, the genetic toggle switch may be used to detect a biochemical event associated with production of the switching agent. Any genetic toggle switch construct that is used to detect biochemical events within the cell may also be switched by externally applied switching agents as described above.

In order to use the genetic toggle switch as a detector of biochemical events within the cell, it may be necessary to modify the components of the toggle switch such that it responds to endogenous switching agents. For example, the genetic toggle may be modified to switch in response to endogenous transcription factors by positioning, upstream, downstream, or within one of the two constitutive toggle promoters, one or more copies of the DNA sequence recognized by the transcription factor. Alternatively, the genes encoding the repressor genes may be modified to include sequences complementary to all or part of an RNA transcript endogenous to the cell. Further modifications of the genetic toggle switch, including the modification of the transcription rates from the constitutive promoters, the modification of repressor stability and binding affinity, and the modification of the rate of translation or degradation of repressor mRNA, may be necessary to adjust the sensitivity with which the genetic toggle switch responds to the presence of endogenous switching agents.

Once the genetic toggle switch construct has been modified to switch in response to the endogenous switching agent, it may be operably linked to one or more genes of interest and introduced into a cell by methods known in the art.

A preferred use of a genetic toggle switch construct is to obtain information on the cellular and physiological function of genes and proteins. For years, scientists have studied gene function by adding, deleting or modifying genes in cells or model organisms and observing the ensuing phenotypic changes. However, such irreversible genetic changes can lead to experimental complications. First, they do not provide clean negative experimental controls, because genetically modified cells must be compared directly with unmodified cells. Thus, it is often unclear whether observed phenotypic differences between samples and controls result from the introduced genetic changes or are artifacts of the genetic manipulations. Second, irreversible genetic changes to cells typically produce compensatory changes in gene expression that mask the roles of the deleted or modified genes.

Accordingly, conditional expression of a gene of interest using a toggle switch construct provides clean negative experimental controls. A single population of genetically identical cells that contain a gene of interest coupled to and regulated by a toggle switch is split into two samples. The gene of interest is activated in one sample, and inactivated in the other sample. The physiological properties of the activated and inactivated cells are evaluated using one or more methods known in the art, including light microscopy, fluorescence microscopy, immunofluorescent staining, flow cytometry, northern blots, western blots, southern blots, cDNA arrays, subtractive hybridization, differential display, serial analysis of gene expression (SAGE), oligonucleotide arrays, enzyme linked immunosorbent assays (ELISA), and antibody arrays. The properties of the active and inactive cells can be compared directly to determine the effect of the gene of interest on cell function and physiology. In addition, the gene of interest can be rapidly switched on or off, denying cells sufficient time to compensate for the missing gene.

Existing conditional expression systems, including the Tet-On/Tet-Off [Gossen, M & Bujard, H, Proc. Natl. Acad. Sci. USA, 89:5547–5551, 1992], ecdysone-regulated [No D, et al., Proc. Natl. Acad. Sci. USA, 93:3346–3351, 1996], anti-progestin regulated [Wang, Y, et al., Proc. Natl. Acad. Sci. USA, 91:8180–8184, 1994], and dimerization-based systems [Rivera, V M, et al., Nature Medicine, 2:1028–1032, 1996], and other approaches utilize externally applied compounds to directly regulate gene expression such as synthetic zinc-finger proteins [Beerli, R R, et al. Proc. Natl. Acad. Sci. USA, 97:1495–1500, 2000], antisense oligonucleotides [Delihas, N, et al., Nat. Biotechnology, 15: 751–753, 1997], and synthetic ribozymes [Bramlage, B, et al., Trends Biotechnology, 16: 434–438, 1998], all require the continuous application of chemical or biochemical compounds. The continuous application of such compounds can have undesirable or deleterious consequences for the cells, tissues, or animals to which they are applied. In addition, continuous application of inducers can confuse experimental results. For example, tetracycline, a commonly used inducer, is not perfectly specific for its target transcription factors. Tetracycline derivatives have been shown to interact with neural transcription factors [Chen, M, et al., Nature Medicine, 6: 797–801, 2000] and can cause defective embryonic development in animal models [Mayford, M, et al., Science, 274: 1678–1683, 1996]. Moreover, continuously applied inducing compounds such as tetracycline and mifepristone can accumulate over time in the tissues of animal subjects. The accumulated reservoirs result in slow clearance of inducers from the body and, consequently, long switch shut-off times.

Accordingly, toggle switch constructs of the invention, which require only a transient application of an switching agent to switch gene expression "on" or "off", avoid the side-effects of systems that require continuous application of inducing compounds.

Other useful embodiments of the invention include: use of multiple toggles in an array (e.g., to control multiple genes in cancer cell lines); use of single or multiple toggle sensors in cell culture (e.g., to monitor multiple genes); use of toggle switches to control cytokine production in human gene therapy through topical/oral antisense oligonucleotide administration; use of toggle switches to turn "on" and "off" genes of interest in a transgenic animal (e.g., to control expression of Hodgkins gene in a transgenic mouse); use of sensors in stem cells to redirect differentiation; use of toggle switches as sensors in mice to switch "on" or "off" a gene in response to activation of another gene; and use of toggle switches as sensors in high throughput screens to detect responses to combinatorial chemistry libraries.

The following examples serve to illustrate certain preferred embodiments and aspects of the present invention and are not to be construed as limiting the scope thereof.

EXAMPLES

Example 1

Experimental Considerations for Toggle Switches

A. General Considerations

The following sections address experimental and theoretical aspects of genetic toggle switches.

i. Imbalanced Repressor Expression

Theoretical modeling and experimental results show that an imbalance between the transcription or translation efficiency of the repressor genes can disrupt the bistable function of a toggle switch. In such a situation, one repressor can dominate and shut down expression of the other even after transient application of a switching stimulus that acts on the dominant repressor. Thus, if bistability is not exhibited in an initial toggle switch construct, it may be due to the imbalance of transcription or translation between the two repressors of the switch. To achieve balanced transcription efficiency of the two repressors, the expression levels from different promoters can be assayed using RT-PCR, Northern blots, reporter gene assays, or other methods known in the art. Promoters with the most closely matched transcription efficiencies are preferably selected. In addition, promoter strengths may be adjusted using random mutagenesis and screening techniques known in the art Alternatively, translation initiation signals, repressor codon usage, or other characteristics of the repressor mRNAs may be modified as described below to adjust translation efficiency.

ii. Leaky Repression

The bistability of a genetic toggle switch can also be disrupted if one or both repressors fail to sufficiently inhibit the expression of the other repressor, i.e. repression is leaky. If one repressor is leaky, the more effective repressor may dominate. If both repressors are leaky, the toggle switch may settle at an intermediate expression state in which both promoters are partially active. Accordingly, a preferred toggle switch includes repressor genes that are non-leaky in that each repressor gene tightly represses expression of the other repressor gene.

iii. Toxicity of Switching Agents

A switching agent or inducer that is used to switch a toggle between stable expression states may have deleterious effects on host cells. Accordingly, preferred repressors respond to non-toxic switching compounds. For example, if IPTG is toxic in humans, a LacI repressor can be replaced with a Pip repressor which is inducible by the human-approved antibiotic Synercid™.

iv. Homologous Recombination

To simplify the construction of the toggle switch it may be desirable to use two copies of the same genetic element. For example, the same promoter may be used for both transcription units, or the same repressor domain may be used for both repressor genes. However, duplication of DNA fragments may enhance the opportunity for homologous recombination within the host cell. These events could destroy the toggle switch construct. If homologous recombination is a problem, duplication of element may be avoided or silent mutagenesis may be used to decrease the level of homology.

v. Performance Testing

The performance of a bistable genetic switch can be evaluated in five areas: (1) long-term stability, (2) reversibility, (3) switching time, (4) leakiness, and (5) dynamic range.

(1) Long-term Stability

To test long-term stability, switching agents (for example, tetracycline or IPTG) may be applied to switch the toggle into each of its two expression states. The switching agents may then be removed, and the time during which the toggle remains in its respective state, for example, hours, days or weeks is observed. In principle, the toggle switch will not switch to the opposite state without external stimulation. However, the noise and variability that is inherent in cellular gene expression may cause cells that contain the toggle switch to flip stochastically to the opposing state. If such a phenomenon is observed, the efficiency of both promoters may be increased to make the switch more robust. Long-term stability tests also are necessary to verify that the observed bistability is not merely an artifact of a very slow settling system, i.e., a system that takes a very long time to return back to the steady state after it has been perturbed. Such behavior might be misinterpreted as bistability in short-term expression experiments.

(2) Reversibility

A single population of cells may be repeatedly switched back and forth between the two stable expression states in order to observe whether the reversibility of the switch continues to be effective after several cycles. Although reversibility is not expected to be a problem, it is critical to many anticipated applications of the toggle. Thus, thorough analysis of this characteristic is important.

(3) Switching Time

An ideal toggle switch preferably flips immediately from one state to the other after application of a switching agent. The kinetics of switching in the toggle switch may be observed by taking samples before, during, and after switching (in both directions) at frequent intervals. Such sampling is facilitated by the use of reporter genes that encode secreted proteins. If necessary, the rate of switching may be improved by applying methods to increase the rates of degradation of repressor mRNA or protein.

(4) Leakiness

The toggle switch likely will have the greatest practical utility if it exhibits undetectable levels of leakage expression of the genes that are switched off in either expression state. Leakage expression may be carefully assayed using the highly-sensitive ELISA assays of reporter genes such as hHGF and hVEGF. If necessary, leakage expression can be improved using methods described below which include the addition of repressor domains, repositioning the operator sites in the toggle promoters, and mutating repressor or promoter DNA to increase the binding affinity of the repressor for its operator site.

(5) Dynamic Range

Due to the regulatory feedback in the toggle switch design, the switch may exhibit greater dynamic range than current inducible switches. Dynamic range may be measured by assaying the maximum expression of genes in the "on" state and comparing them to the minimum expression of genes in the "off" state. If necessary, it may be possible to improve the dynamic range further by adjusting the properties of the individual components of the toggle.

B. Optimization of Repressor Expression

As discussed previously, the efficiency of repressor expression is an important feature of the toggle switches of the invention. Repressor expression may be altered in prokaryotic and eukaryotic cells by manipulating one or more of the following features: the strength of RNA polymerase (RNAP) binding to DNA ($K_{mu}$ or $K_{mv}$); the maximum rate of mRNA synthesis by RNAP ($\lambda 1$ or $\lambda 2$); the strength of inhibitor binding to the DNA ($K_{iu}$ or $K_{iv}$); the rate of translation of mRNA into functional protein ($k_1$ or $k_2$); and the rate of protein degradation, i.e., protein stability, ($d_1$). These features are further described below.

i. RNAP Binding

In prokaryotic cells, recognition of the promoter sequence by RNAP is mediated by helper proteins called sigma factors that bind to two sites in the promoter: the Pribnow box (or −10 region) and the −35 region. Typically, each of these sites has an ideal sequence called a consensus sequence. The strength of binding of sigma factors, and thus the strength of RNAP binding, is determined by how closely these regions match their consensus sequence [Darnell et al (1990), supra]. Furthermore, modifications of a region upstream of the −35 region, called the UP element, have been shown to dramatically alter the rate of transcription [Estreem, S T et al. (1998) Proc. Natl. Acad. Sci. USA 95:9761–9766; Yamada, M, et al. (1991) Gene 99:109–114]. The UP element, which has also been shown to have a consensus sequence, probably enhances the binding of the RNAP complex. By modifying the sequence of the –10, –35 and UP regions, e.g., by introducing a deletion, point mutation or insertion, the strength of RNAP binding and, hence, the promoter strength, can be altered. Relative promoter strengths can be determined by quantitative assays of the expression of reporter genes such as the green fluorescent protein (GFP), β-galactosidase ((β-gal), or chloramphenicol acetyl transferase (CAT). Thus one of skill in the art may determine whether, for example, a mutation has increased or decreased the level of expression of a gene.

ii. Transcription Elongation

Once the RNAP binds to a promoter, it opens the DNA double helix and moves forward, adding ribonucleotides to the mRNA transcript. The rate of transcription is determined partially by the nucleotide content, and partially by the secondary structure (if any) of the mRNA. High guanosine and cytosine content of the mRNA tends to slow the transcription rate [Darnell et al. (1990) supra]. Furthermore, secondary structures that form in the mRNA behind the transcription complex can interfere with the transcription process [Darnell et al. (1990) supra]. Although the DNA content of the coding region cannot be substantially altered (only silent mutations alter the mRNA sequence without changing the protein properties), a leader region of mRNA may be inserted upstream of the coding region. This region can be designed to slow the rate of transcription elongation. A change in the rate of transcription elongation may be determined using methods known in the art. For example, pulse labeling mRNA transcripts with radioactive nucleotides can be used to track mRNA both temporally and spatially.

iii. Inhibitor Binding

Special sequences of DNA called operators often are found within or near a promoter. The inhibitor proteins (repressors) block transcription by binding to these operators. A given repressor typically recognizes only one specific operator sequence. The affinity of the repressor for the operator can be altered by modifying the operator sequence, e.g., by introducing a point mutation, insertion or deletion. Exemplary operator sequences useful in the practice of the invention include, for example, $O_{lac}$, $O_{lex}$, $O_{tet1}$, $O_{tet2}$, $O_{R1}$, $O_{R2}$, $O_{R3}$, $O_{L1}$, $O_{L2}$, and $O_{L3}$.

iv. Translation Rate

The rate of translation of mRNA into an amino-acid sequence is governed primarily by three factors: (i) the ribosome binding site (RBS), (ii) the secondary structure of the mRNA, and (iii) the codon usage in the coding region. The RBS typically is located 5–10 bases upstream of the start codon. Translation is most efficient when this sequence matches a consensus sequence called the Shine-Dalgarno (SD) sequence [Darnell et al. (1990) supra; Backman, K & Ptashne, M. (1978) Cell 13:65–71; Jacques, N & Dreyfus, M. (1990) Molecular Microbiology 4:1063–1067; Shine, J & Dalgarno, L. (1975) Nature 254:34–38]. Thus, translation rate can be altered by modifying the RBS, e.g., by introducing a point mutation, insertion or deletion. As in transcription, the formation of secondary structures by the mRNA can interfere with translation machinery. Thus, modification of the leader region of the mRNA or introduction of silent mutations into the coding region may be used to change translation rate. Finally, in various organisms certain codons are favored, i.e., tRNAs for certain codons are more abundant than others. Translation is more efficient when the favored codons are used [Jacques & Dreyfus (1990) supra]. Thus, coding usage can be optimized by introducing silent mutations that utilize the favored codons.

v. Protein Stability

The stability of a protein can be altered by introducing mutations into the amino acid sequence that make the protein more or less resistant to denaturation or proteolytic degradation., Powerful experimental techniques such as directed evolution, DNA shuffling and two-hybrid screening are known in the art and may be used to rapidly screen large numbers of mutant proteins for the desired stability characteristics. In addition, protein degradation rate may be altered by attaching a short, organism-specific, oligonucleotide sequence [Andersen et al. (1998) Appl. Environ. Microbiol. 64:2240–2246] to the 3' end of the gene which encodes the protein. This sequence targets the encoded protein for rapid degradation by the cell.

Design Considerations for Prokaryotic Cells

In one preferred embodiment, the cell containing the genetic cassettes of the invention is a prokaryotic cell. It is contemplated that a variety of prokaryotic host cells including gram-negative and gram-positive cells can be useful in the practice of the invention and may include, for example, *Escherichia coli, Bordetella pertussis, Bacillus subtillis, Salmonella typhimurium*, and *Staphylococcus aureus*. Most preferably, the prokaryotic host cell is *E. coli*.

Figure 6:
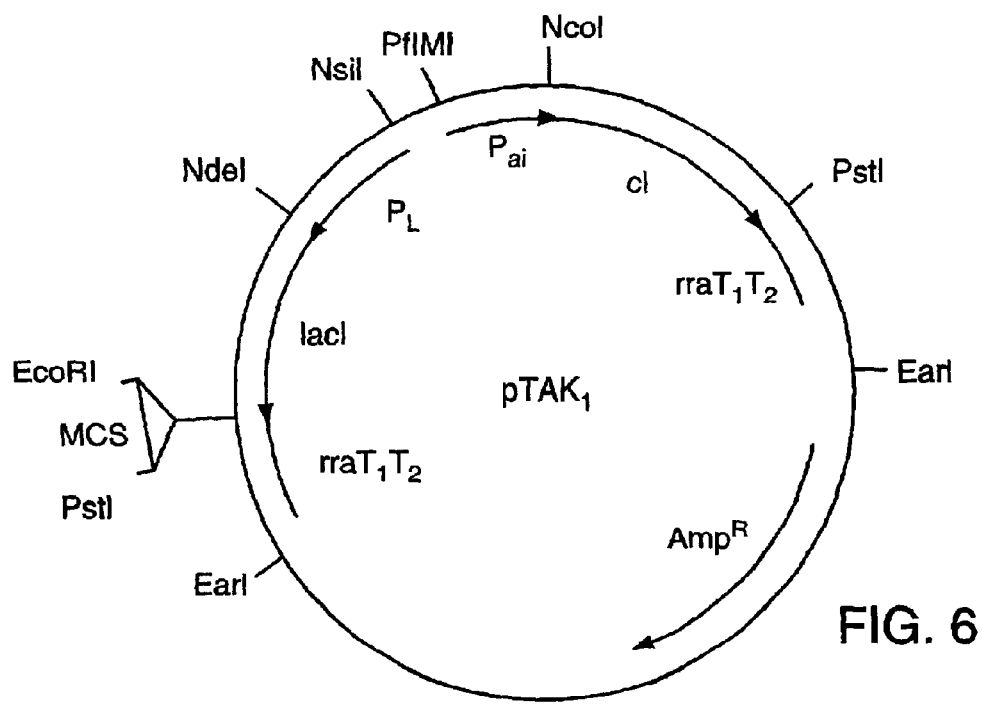
FIG. 6 is a schematic representation of a pTAK$_1$ plasmid carrying an exemplary toggle switch construct.

While the toggle switch construct described herein comprises the $P_L$-LacI-GFPuv and $P_{trc}$-cI operons (see, FIG. 5) which are inserted into the pTAK$_1$ plasmid (see, FIG. 6), those of ordinary skill in the art recognize that the modular design of the pTAK$_1$ plasmid allows insertion of any promoter and any coding sequence into this plasmid to obtain the desired configuration for the toggle switch construct of the invention. For example, where it is desirable to insert a repressor gene other than lacI and/or cI to pTAK$_1$, the repressor gene is amplified and then used to replace lacI and/or cI. Repressor genes may be obtained from wild-type *E. coli* or as plasmids from a number of commercial suppliers and manipulated using methods known in the art.

While the invention is illustrated using *E. coli*-based constructs, toggle switches which function in other prokaryotic cells are expressly contemplated to be within the scope of the invention. Switches which contain *E. coli* promoters may function without modification in related bacterial species such as gram-negative bacteria, or may be modified to bring about transcription of the gene of interest.

While the toggle switch constructs of the invention are illustrated by the exemplary $P_L$-LacI-Clone and $P_{trc}$-cI operons in the toggle switch construct, the invention is not limited to the type of promoter, repressor protein or switching agent used. Any repressor protein may be used so long as it reduces transcription by cognate promoter. Similarly, any switching agent may be used so long as it increases transcription by the promoter that is acted on by the particular repressor protein.

Prokaryotic repressor-promoter-switching agent combinations suitable for use in the toggle switch constructs are known in the art, such as those described in the Swiss-Prot protein database [Annotated Protein Sequence Database; http://expasy.hcuge.ch/sprot/sprottop.html]. Suitable prokaryotic promoters are exemplified by those in Table 1.

TABLE 1

Examples of E. coli constitutive promoters, repressors, and switching agents suitable for toggle switch constructs

| REPRESSOR | PROMOTER | SWITCHING AGENT |
| --- | --- | --- |
| ArsR | Arsenic operon | Arsenate or oxidized arsenic, antimony & bismuth |
| AscG | ASC operon | Unknown |
| LacI | $P_{trc}$ | IPTG |
| CscR | Sucrose operon | D-fructose |
| DeoR (NucR) | Deoxyribose operon | deoxyribose-5-phosphate |
| DgoR | DGORKAT operon | D-galactonate |
| FruR | Fructose operon | D-fructose |
| GalR | Galactose operon | Galactose |
| GatR | Galactitol operon | Unknown |
| CI | $P_L$ | Nalidixic acid; UV light |
| LexA | SOS response regulon | UV light & RecA protein |
| RafR | Raffinose operon | Raffinose |
| TetR | Tetracycline resistance operon | Tetracycline |
| QacR | Multi-drug resistance operon | multiple hydrophobic cations |
| PtxS | Gluconate operon | 2-ketogluconate |

Application of the switching agents of Table 1 to a cell which contains a repressor of Table 1 and its cognate constitutive promoter in the toggle switch construct can be used to switch "on" or "off" the expression of a particular gene of interest.

D. Design Considerations for Eukaryotic Cells

It is contemplated that toggle switches of the invention may be harbored in a eukaryotic cell. Preferred eukaryotic cells include, for example, yeast cells, plant cells, insect cells, algae and mammalian cells (including human cells). Particularly preferred eukaryotic cells include myeloma cells, fibroblast 3T3 cells, monkey kidney or COS cells, chinese hamster ovary (CHO) cells, mink-lung epithelial cells, human foreskin fibroblast cells, human glioblastoma cells, and teratocarcinoma cells, HER 293, L929, and HeLa cells.

Constitutive eukaryotic promoters typically comprise two elements: the minimal promoter sequence, for example from base pairs +1 to −65; and an enhancer sequence encompassing several hundred base pairs upstream of the minimal promoter. The minimal promoter sequence contains the TATA box consensus sequence and is necessary but not sufficient for RNA polymerase II binding and transcription. In the absence of the enhancer the minimal promoter typically does not efficiently initiate transcription (Darnell, J., et al. (1990) supra; Gossen & Bujard, J. (1992) supra; Lubon, H., et al. (1989) Molecular and Cell Biology, 9:1342–1345; Thomsen, D R., et al. (1984) supra). Thus, a strong eukaryotic constitutive promoter requires both a minimal promoter region and an upstream enhancer region. Exemplary strong constitutive eukaryotic promoters which direct efficient transcription in the absence of an activator and which lack an operator sequence are known in the art (e.g., those disclosed in the Swiss-Prot protein database) and are exemplified by those listed in Table 2.

TABLE 2

Examples of Strong Constitutive Eukaryotic Promoters

| Promoter | Parent Organism/Gene |
| --- | --- |
| $P_{hCMV}$ | Human Cytomegalovirus Immediate Early Promoter [Gossen, M. & Bujard, H. (1992); Gossen, M., et al. (1995)] |
| $P_{HSVtk}$ | Herpes Simplex Virus Thymidine Kinase Promoter [Smith, GM., et al. (1988) EMBO J., 7: 3975–3982] |
| $P_{SV40}$ | Simian Virus Early Promoter [Wildeman, AG. (1988) supra] |
| $P_{EF-1\alpha}$ | Human [Takeuchi, Y., et al. (1999) Mar. Biotechnol., 1(5): 448–0457] |
| RSV-LTR | Rat Sarcoma Virus Promoter [Franz, WM., et al. (1997) Cardiovasc. Res., 35(3): 560–6] |
| Keratin 6 | Human [Mazzalupo, S., et al. (2001) Mech. Dev., 100: 65–69] |

While the promoters in Table 2 direct efficient transcription, these promoters typically are not repressed because they lack an operator sequence. Thus, in order to repress the exemplary promoters in Table 2, operator sequences need to be operably linked to the promoter sequence.

Because of the differences between eukaryotic and prokaryotic transcriptional machinery, a bacterial promoter typically is not recognized and transcribed by the eukaryotic RNA polymerase II. However, it has been previously shown that hybrid eukaryotic promoters (i.e., promoters composed of a constitutively transcribed eukaryotic promoter and a bacterial operator sequence) are efficiently transcribed in the absence of the associated bacterial repressor protein, and are effectively repressed in the presence of the bacterial repressor. For example, a hybrid promoter has been constructed by splicing the E. coli LexA operator sequence into the HSV tk promoter. Expression from this promoter was reduced 10-fold in mammalian cells that synthesized the E. coli LexA repressor protein [Smith, G M. (1988) supra]. Thus, toggle switches which are functional in eukaryotic cells may be constructed using an approach similar to that described above for E. coli.

Figure 7:
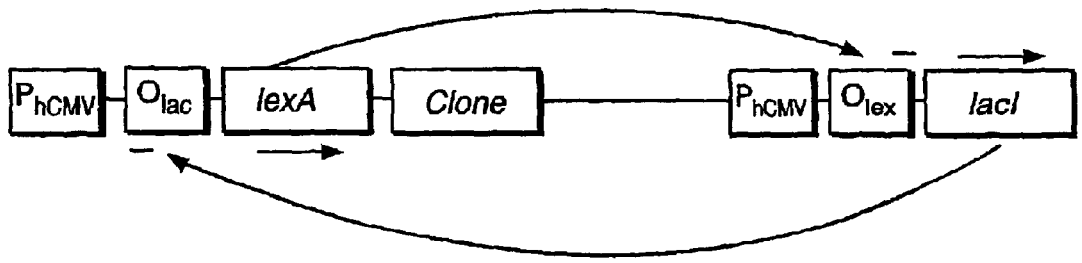
FIG. 7 is a schematic representation of an exemplary eukaryotic toggle switch construct.

A eukaryotic toggle switch can be constructed from hybrid promoters containing a constitutive eukaryotic promoter and an appropriate E. coli operator. This is illustrated by the construction of the exemplary toggle switch containing one operon comprising the $P_{hCMV}$ promoter, the lexA operator gene and the lac repressor gene and another operon comprising the $P_{hCMV}$ promoter, the Lac operator, and the lexA repressor gene as shown in FIG. 7. The Human Cytomegalovirus Immediate Early Promoter, $P_{hCMV}$ directs constitutive transcription of both genes lexA and lacI. The LexA protein, encoded by the lexA gene, represses transcription at operator site $O_{lex}$. The LacI protein, encoded by the lacI gene, represses transcription at operator site $O_{lac}$. An additional gene or genes of interest (Clone) is placed under the control of one of the $P_{hCMV}$ promoters.

E. Transfer Genetic Toggle Switches into a Host Cell

A genetic toggle switch, and the genes of interest to which it is operably linked, may be inserted into any of several types of DNA vectors used to transfer DNA into a cell. Examples include linear DNA, plasmid DNA, shuttle vectors, modified viruses and artificial chromosomes. The vector containing the genetic toggle switch may then be introduced into any prokaryotic or eukaryotic cell using any of several methods including naked DNA uptake, receptor-mediated endocytosis, viral infection, lipofection, DEAE-Dextran transfection, calcium chloride transformation, calcium phosphate transfection, and electroporation. Once the vector is introduced into a cell, it may be stably maintained in the cell by applying an appropriate selective agent for example, an antibiotic, for example, neomycin, zeocin, ampicillin, and kanamycin. In other circumstances, for example, when the requisite genes are incorporated into the genome of the host cell by, for example, homologous recombination, selective agents may not be required.

F. Application of a Switching Agent

In order to effectively modulate repressor activity at the expression level (for example, transcription and/or translation) or at the post-translational level (for example, allosteric or steric inhibition of DNA-binding), a switching agent must enter the cytoplasm and possibly the nucleus of the cell containing the genetic toggle switch construct. Agents may be added directly to the cell's growth medium where they will pass through the cell membrane and into the cytoplasm, or hey may be introduced into the bloodstream or tissues of an animal containing the genetic toggle switch construct. Methods suitable for introduction of an agent into an animal include intravenous injection, subcutaneous injection, transdermal uptake, and oral injection. Agents may also be added directly to cell growth medium, or introduced into an animal by the methods described above, along with additional chemical compounds that may enhance the permeability of the cell membrane to the agents [Good, L, et al. (2001) Nature Biotech 19: 360–364]. Alternatively, the agent may be introduced into a cell, tissue or animal using methods typically used to mediate DNA vector uptake, including DEAE-Dextran transfection, lipofection, electroporation, and viral infection.

Example 2

Mathematical Analysis of Bistability

Toggle switches of the invention may be designed and tested theoretically using mathematical and computer modeling principles which integrate nonlinear dynamics, chemical physics, biochemistry, and molecular biology. Mathematical and computer modeling of biological systems has been found to be reasonably predictive of the behavior of recombinant constructs, such as cross-regulation constructs [Chen, et al. (1993) Gene 180:1522; Chen et al. (1995) Biotechnol. Prog. (US) 11(4):397–402; Bailey et al., U.S. Pat. No. 5,416,008], oscillatory expression constructs [Elowitz, M. et al. (2000) Nature 403:335–338], and noise-reduction constructs [Becskei, A., et al. (2000) Nature 405:590–593].

According to the invention, the design of a genetic toggle switch can be based on mathematical models describing the dynamic interactions of two mutually inhibitory genes (e.g., as exemplified in FIG. 1A). This type of system exhibits two stable states. In each state, only one of regulatory gene 1 ($R_1$) and regulatory gene 2 ($R_2$) is maximally expressed by the host cell. The following analysis is based on a toggle switch wherein the switching agents that cause the switch to transition from one stable state to another stable state are inducers. The behavior of the genetic toggle switch construct can be modeled using the following pair of equations:

$$\frac{du}{dt} = \frac{k_1 \lambda_1 / \delta_1}{1 + K_{mu}(1 + v^\gamma / K_{iv}^\gamma)} - d_1 u \quad \text{(i)}$$

where, $$\frac{dv}{dt} = \frac{k_2 \lambda_2 / \delta_2}{1 + K_{mv}(1 + u^\beta / K_{iu}^\beta)} - d_1 v \quad \text{(ii)}$$

u=concentration of gene product of regulatory gene 1,
v=concentration of gene product of regulatory gene 2,
$\lambda_1$=maximum rate of synthesis of gene 1 mRNA by RNA polymerase,
$\lambda_2$X=maximum rate of synthesis of gene 2 mRNA by RNA polymerase,
$\delta_1$=rate of degradation of gene 1 mRNA,
$\delta_2$=rate of degradation of gene 2 mRNA,
$k_1$=rate of synthesis of gene product of regulatory gene 1 by the ribosome,
$k_2$=rate of synthesis of gene product of regulatory gene 2 by the ribosome,
$K_{mu}$=Michaelis constant for RNAP binding and transcription of regulatory gene 1,
$K_{mv}$=Michaelis constant for RNAP binding and transcription of regulatory gene 2,
$K_{iu}$=equilibrium constant for inhibitory binding of gene product of regulatory gene 1 to promoter 2,
$K_{iv}$=equilibrium constant for inhibitory binding of gene product of regulatory gene 2 to promoter 1,
$d_1$=rate of degradation of gene products of regulatory genes 1 and 2,
$\beta$=cooperativity of binding of gene product of regulatory gene 1,
$\gamma$=cooperativity of binding of gene product of regulatory gene 2.

The equations are based on the assumption that gene expression can be modeled using the law of mass action. Although gene expression typically does not involve a large number of particles, considerable evidence exists that such approximations provide a reasonable description of gene expression. For example, earlier work using a reconstituted enzyme system [Schellenberger et al., Adv. Enzyme Regul. 19, 257–284 (1980)] demonstrated the effectiveness of non-linear mathematics in predicting novel qualitative behaviors, including multistability and hysteresis, in biochemical reaction networks. In addition, a variety of physical and mathematical approaches, including logical or discrete [Glass et al., J. Theor. Biol. 54, 85–107 (1975); Glass & Kauffman, J. Theor. Biol. 39, 103–129 (1973); Kauffman, J. Theor. Biol. 44, 167–190 (1974); Thomas, J. Theor. Biol. 73, 631–656 (1978); Thomas, J. Theor. Biol. 153, 123 (1991)], piece-wise linear [Tchuraev, J. Theor. Biol. 151, 71–87 (1991)], non-linear [Arkin & Ross, Biophys. J. 67, 560–578 (1994); Bhalla & Iyengar, Science 283, 381–387 (1999); Glass, J. Chem. Phys. 63, 1325–1335 (1975)], statistical-mechanical [Shea & Ackers, J. Mol. Biol. 181, 211–230 (1985); Smith et al., Math. Biosci. 36, 61–86 (1977)] and stochastic [Arkin et al., Genetics 149, 1633–1648 (1998); McAdams & Arkin, Proc. Natl. Acad. Sci. USA 94, 814–819 (1997); McAdams & Arkin, Annu. Rev. Biophys. Biomol. Struct. 27,199–224 (1998)] formulations of the underlying biochemical dynamics, have had varying degrees of success in describing the behavior of gene networks.

The first term in each equation describes the synthesis of nascent proteins. Both transcription by the RNA polymerase and translation by the ribosome are included in the first term. Transcription, modeled with Michaelis-Menton kinetics, is competitively inhibited by the opposing gene product. Inhibition is achieved by the binding, as a homo-multimer, of one gene product to one or more sites in the opposing gene's promoter region. The multimeric interaction and the multiple binding sites are accounted for by the cooperativity exponents 0 and 7 in the first term of each equation.

The second term describes the rate of degradation of proteins. In *E. coli*, the dilution of proteins as a result of cell growth is assumed to be the major determinant of the degradation rate. Since this rate is assumed to be identical for all proteins in the cell, a single rate constant, $d_1$, is used in the model for protein degradation. However, the assumption of a single rate constant is not necessary for a functional toggle switch. The bi-stable behavior can exist in a toggle switch with unequal degradation rates of the proteins, but a compensating adjustment in the promoter strengths, $\alpha_1$ and $\alpha_2$, may be necessary as described below. Additional assumptions, implicit in this model, are (i) mRNA turnover is rapid, and (ii) translation of each mRNA transcript occurs at its maximum rate, i.e. proteins are rapidly synthesized from the mRNA by an excess of ribosomes. These assumptions are supported by studies of transcription and translation [Alberts, B et al. (1994) Molecular Biology of the Cell, Garland Publishing, Inc., New York; Darnell, J et al. (1990) Molecular Cell Biology, Scientific American Books, Inc., New York].

Figure 8A:
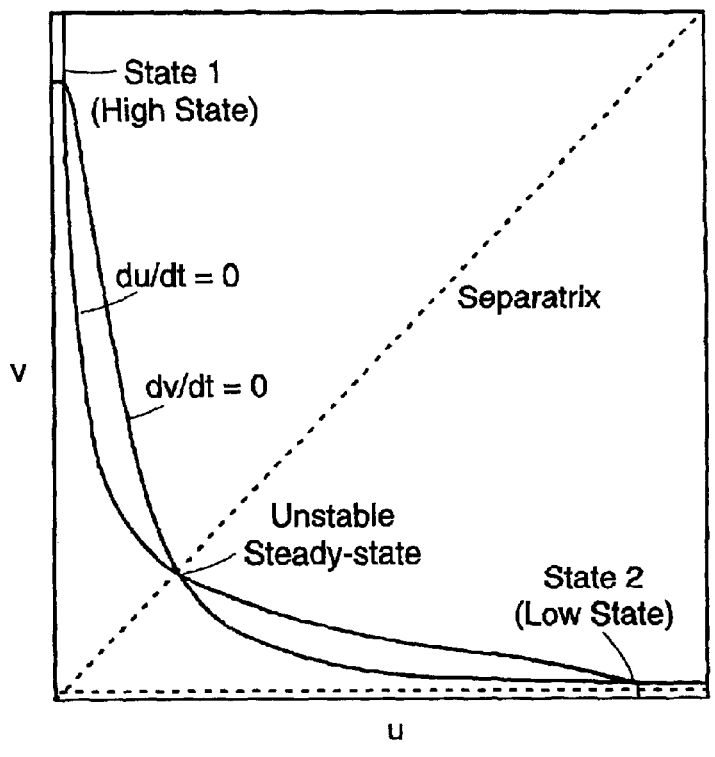
FIGS. 8A and 8B are graphs describing the behavior of a toggle switch construct with balanced promoter strengths (FIG. 8A) or with imbalanced promoter strengths (FIG. 8B).
Figure 8B:
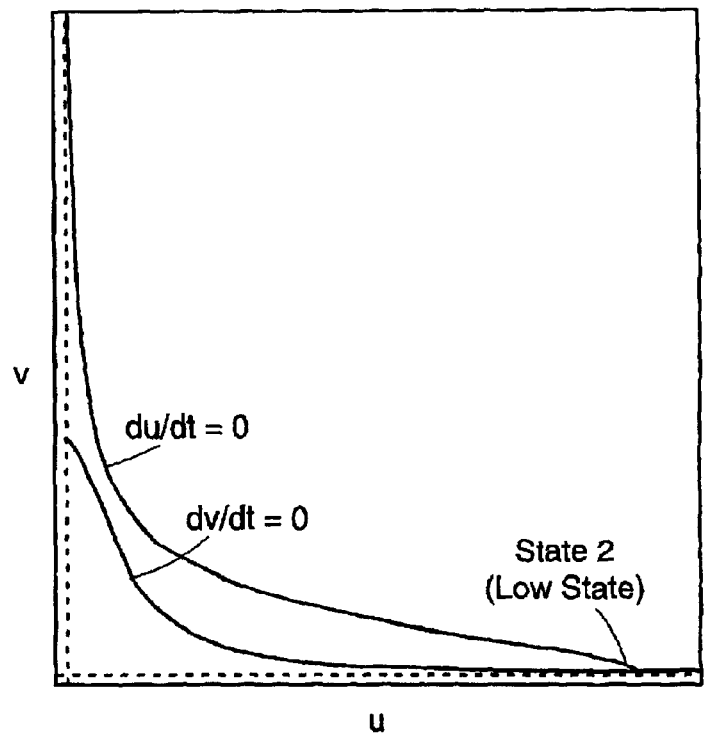

FIG. 8 shows the geometric structure of equations (i) and (ii). FIG. 8A represents a modeled bistable toggle network with balanced promoter strengths. FIG. 8B represents a modeled monostable toggle network with imbalanced promoter strengths.

As shown in FIG. 8A, a cell with the toggle switch construct genes settles to State 1 if its initial state is anywhere above the Separatrix (i.e., in the first basin of attraction); it settles to State 2 if its initial state is anywhere below the Separatrix (i.e., in the second basin of attraction). FIG. 8A reveals the origin of the bi-stability. The nullclines (du/dt=0 and dv/dt=0 in FIG. 8A) intersect in three places producing one unstable and two stable steady-states.

Figure 9A:
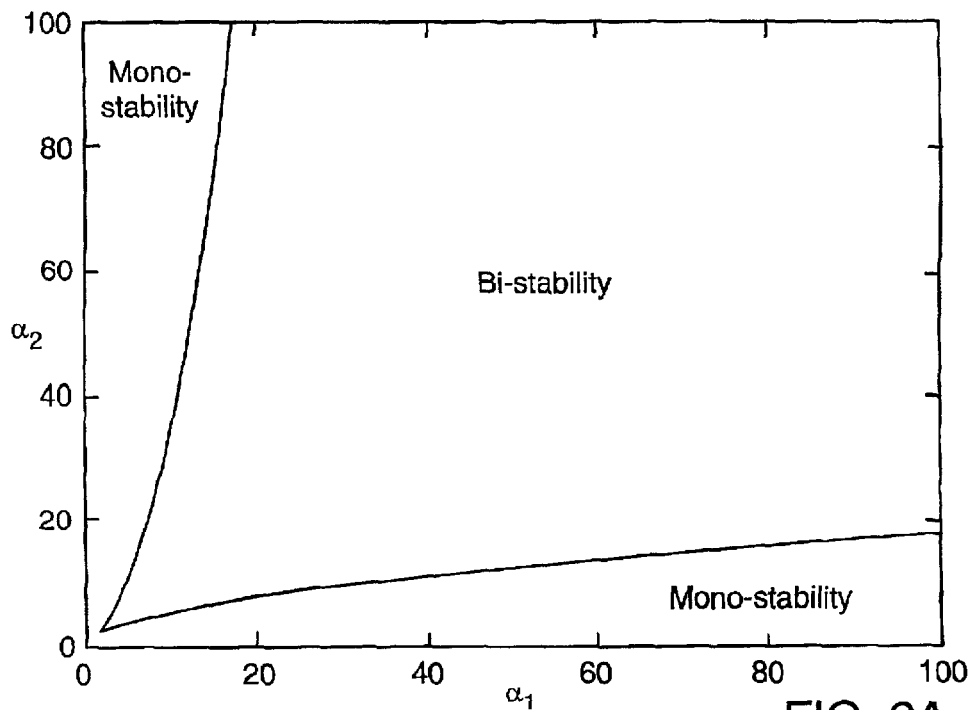
FIGS. 9A-D are graphs providing a bifurcation analysis of an exemplary toggle switch construct.

From FIG. 8A, three key features of the system become apparent. First, the nullclines intersect three times, rather than once, because of their sigmoidal shape. The sigmoidal shape arises for $\beta$, $\gamma>1$. Thus, in one embodiment, the bi-stability of the system depends on the cooperative binding of the inhibitory proteins to the DNA. Second, the strengths of the promoters preferably are matched. The terms "matched" and "balanced" when used herein in reference to the strengths of a first and second promoters mean that the effective strengths of the first and second promoters ($\alpha_1$ and $\alpha_2$ as described below) are within the bi-stable region illustrated, for example, in FIG. 9A. Promoter strength may be determined by conventional quantitative assays of the expression of reporter genes such as the green fluorescent protein (GFP), $\beta$-galactosidase ($\beta$-gal), or chloramphenicol acetyl transferase (CAT).

In order to construct a first and second promoters with matched strengths, the skilled artisan should use the same type of assay to quantitatively determine the strength of each promoter. If the strengths of the promoters do not fall within the bi-stable region illustrated in FIG. 9A, one or both promoters may be modified and their strengths re-quantitated. Modification of one or both promoters may be repeated, if necessary, until the strengths of the promoters fall within the bi-stable region of FIG. 9A. If the strengths are not matched, the nullclines intersect only once producing a single stable steady-state (FIG. 8B). This may occur in plasmid pIKE105 discussed in Example 4. Third, the state of the toggle is switched by the application of a transient pulse of an inducing stimulus that pushes the system away from the stable steady state, over the separatrix, and into the opposite basin of attraction.

To build a working genetic toggle switch construct which produces robust bi-stable behavior in vivo, it is helpful to understand the effects of the eleven parameters in the first pair of equations (i) and (ii). This analysis is facilitated by rescaling time and non-dimensionalizing the variables into the following pair of equations (iii) and (iv):

$$\frac{d\hat{v}}{d\tau} = \frac{\alpha_2}{1+\hat{u}^\gamma} - \hat{v} \quad \text{(iii)}$$

$$\frac{d\hat{u}}{d\tau} = \frac{\alpha_1}{1+\hat{v}^\beta} - \hat{u} \quad \text{where,} \quad \text{(iv)}$$

$$\tau = d_1 t,$$

$$\hat{u} = \frac{u}{K_{iu}(1/K_{mv}+1)^{1/\beta}},$$

$$\hat{v} = \frac{v}{K_{iv}(1/K_{mv}+1)^{1/\gamma}},$$

$$\alpha_1 = \frac{k_1\lambda_1/\delta_1}{d_1 K_{iu}(1+K_{mu})(1/K_{mv}+1)^{1/\beta}} \quad \text{and,}$$

$$\alpha_2 = \frac{k_2\lambda_2/\delta_2}{d_1 K_{iv}(1+K_{mv})(1/K_{mu}+1)^{1/\gamma}}.$$

Nine parameters in equations (i) and (ii) collapse into two. Thus, the range of dynamic behaviors that can be produced by this system is easily understood by analysis of only four parameters. The two new parameters, $\alpha_1$ and $\alpha_2$, are the effective strength of promoters 1 and 2, respectively. The parameters $\alpha_1$ and $\alpha_2$ are lumped parameters that describe the net effect of RNAP binding, open-complex formation, transcript elongation, transcript termination, repressor binding, ribosome binding and polypeptide elongation. The cooperativity described by $\beta$ and $\gamma$ can arise from the multimerization of the repressor proteins and the cooperative binding of repressor multimers to multiple operator sites in the promoter. An additional modification to equations (iii) and (iv) is needed to describe induction of the repressors. Since bistability arises in the absence of inducers, this modification is not included in the present discussion. As used herein, the terms "effective promoter strength" and "promoter strength" when used in reference to a nucleic acid sequence are used interchangeably to refer to the ability of the nucleic acid sequence to initiate transcription of an oligonucleotide sequence into mRNA and translation into protein. Promoter strength may be experimentally determined using, methods known in the art, for example, Northern blots RNAase protection assays, reporter gene expression, and SDS polyacrylamide gel electrophoresis. Promoter strength is the net effect of the RNAP binding affinity, the transcription rate, the inhibitor binding affinity and the translation efficiency and mRNA degradation rate. These physical quantities can be manipulated in the experimental system to achieve the desired promoter strength as described above.

FIG. 9 shows the result of two-parameter bifurcation analyses of the system. It can be seen in FIG. 9A that the region of bi-stability grows larger as the strength of both promoters is increased; thus, the system becomes more robust. In other words, as the absolute strengths of the promoters increase, the system exhibits bi-stable behavior for larger relative imbalances in their strength. In FIG. 9B, the bifurcation analysis reveals that the slopes of the bifurcation lines, for $\alpha_1$ and $\alpha_2$ are determined by $\beta$ and $\gamma$. If both $\beta$ and $\gamma$ are less than or equal to 1, then bi-stability is difficult to achieve. Calculations show that in order to achieve bi-stability, regardless of the value of $\beta$ and $\gamma$, $\alpha_1$ and $\alpha_2$ should not be less than 1. Calculations also show that if one promoter is too weak or too strong, then the system falls outside the bi-stable region in FIG. 9C.

Figure 9B:
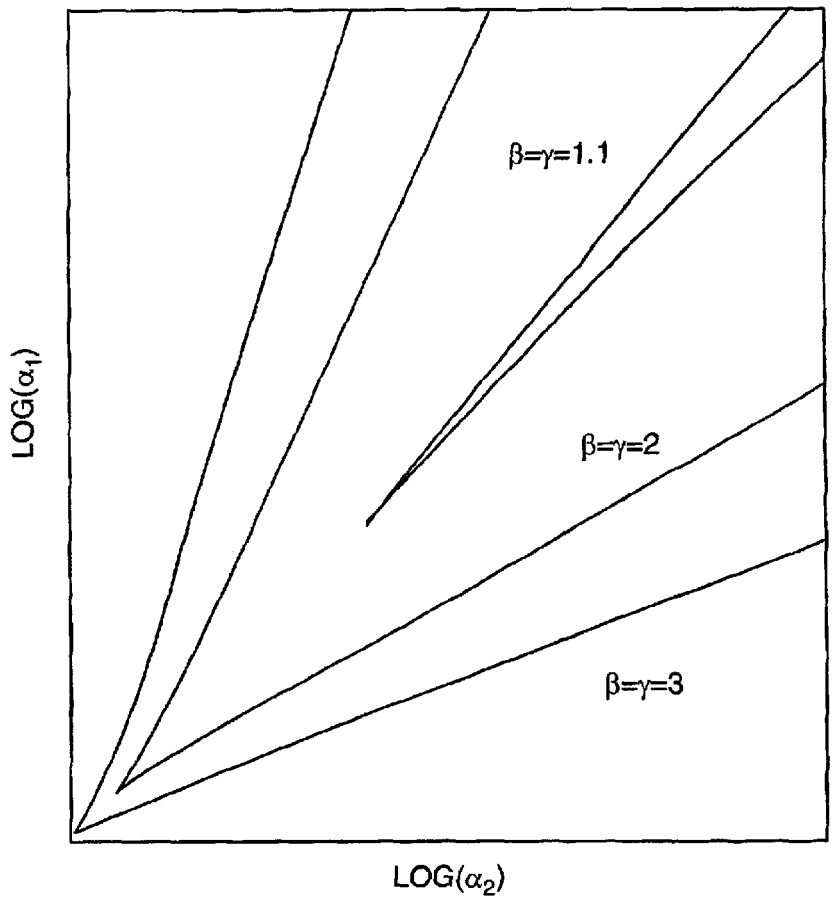
Figure 9C:
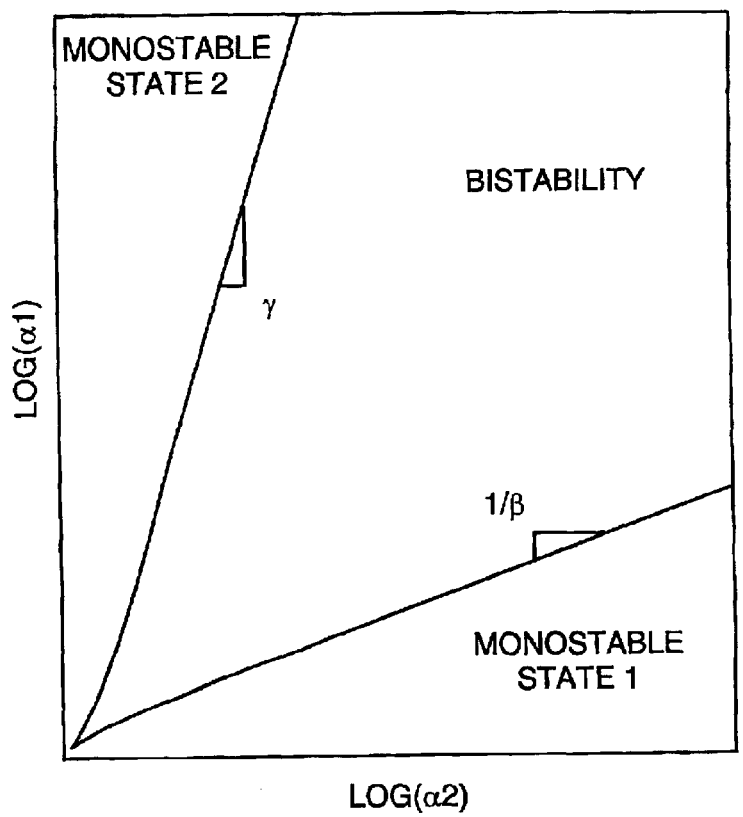

FIG. 9B shows that there is a "tradeoff" between the values of $\beta$ and $\gamma$ on the one hand and the values of $\alpha_1$ and $\alpha_2$ on the other. As the values for $\beta$ and $\gamma$ increase, stability is attainable for decreased values of $\alpha_1$ and $\alpha_2$. Thus, to obtain bi-stability, one of the inhibitors preferably represses expression with cooperativity greater than one. This suggests that repressor multimerization, or multiple operator sites in the promoter, may be helpful to obtain bi-stability. Higher-order multimerization may increase the robustness of the system, allowing weaker promoters to achieve bi-stability. The robustness of a system refers to its ability to exhibit the desired behavior under non-ideal conditions and unintended perturbations, e.g., thermal fluctuations, mismatched promoter strengths, external agents that interfere with protein function or internal perturbations to gene expression such as DNA replication. Cooperativity is an inherent property of some protein repressors. Cooperative binding may arise through multimerization of the protein and through multiple binding sites in the promoter. Protein repressors which exhibit a preferred degree of cooperativity are known in the art (e.g., those listed in the protein database SwissProt).

Figure 9D:
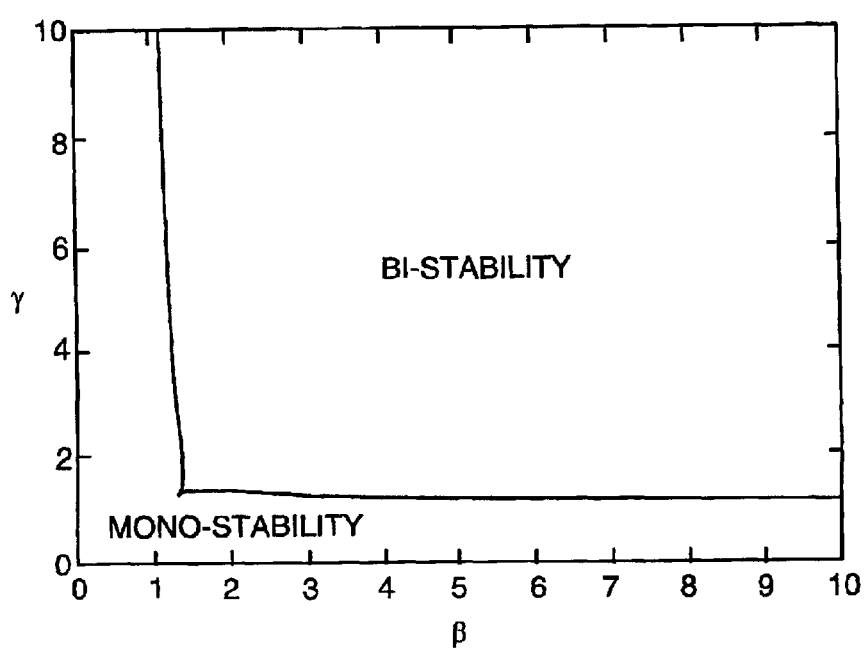

Furthermore, in one embodiment, if one promoter is too weak (e.g., $\alpha_1$ or $\alpha_2 < 2$ for $\beta = \gamma = 2$), then bi-stability is unattainable regardless of the strength of the opposing promoter. In another embodiment, the bifurcation analysis suggests that the repressors preferably bind the DNA as dimers (i.e., $\beta = \gamma = 2$) for $\alpha_1 = \alpha_2 = 10$ (FIG. 9D).

According to the invention, if the first and second repressor proteins bind as homodimers, the bi-stability of the toggle switch construct theoretically is optimal if the strengths of the first and second promoters are manipulated such that the strength of each of the first and second promoters (i.e., $\alpha_1$ and $\alpha_2$) have a value of greater than 2. However, where the first and second repressor proteins bind as homomultimers other than dimers, the minimum permissible value for $\alpha_1$ or $\alpha_2$ is reduced. This minimum approaches a value of 1 as the degree of multimerization increases, but typically does not fall below 1. The strengths of the first and second promoters may be adjusted by manipulating RNAP binding, transcription elongation, inhibitor/activator binding, translation rate, and/or protein stability as described herein.

Theoretical curves in this example were calculated numerically from equations (iii) and (iv) using Matlab (Mathworks), XPP-AUTO, software for simulation and analysis of differential equations (G. B. Ermentrout, University of Pittsburgh, available at http://www.pitt.edu/-phase/), or AUTO, a bifurcation package included in the XPP-AUTO software (E. Doedel, McGill University).

While the above theory is described for an exemplary system with a competitive DNA-binding inhibitor, the same theory applies equally to systems with other types of inhibition. For example, inhibition through protein-protein binding, uncompetitive, and non-competitive interactions result in the same qualitative features of bi-stability.

Example 3

Construction of Exemplary Toggle Switches

This Example demonstrates the successful construction and testing of a variety of toggle switches which exhibit bi-stability and an ideal switching threshold.

All the toggle switches described herein were constructed using *E. coli* plasmids conferring ampicillin resistance and containing the pBR322 ColEl replication origin. Each toggle switch comprised two repressors and two constitutive promoters wherein each promoter was inhibited by the repressor transcribed by the opposing promoter. The toggle switch genes were arranged as a Type IV plasmid as shown in FIG. 10D. In FIG. 10D, the promoters are denoted by solid rectangles with arrowheads, genes are denoted with solid rectangles, ribosome binding sites and terminators ($T_1, T_2$) are denoted by outlined boxes. The Ptrc-2 promoter ($P_2$) with RBS-E (RBS2) and the lac gene ($R_1$) were used in all Type II, III and IV plasmids (FIGS. 10B, 10C and 10D, respectively). RBS-B (shown in FIG. 11) was used for the reporter gene in all Type IV plasmids. Different $P_1$ promoters, RBS1 ribosome binding sites, and/or $R_2$ repressors, were used for the various toggle switches. The two opposing promoters and repressor genes were arranged back-to-back in opposite orientation to minimize unintended phenomena such as transcription read-through and antisense transcription. Though all genes were contained on a single plasmid, the two halves of the toggle could, in principle, be placed on separate plasmids without altering the functionality of the toggle.

i. Plasmid Construction

Two classes of toggle switches were constructed—the pTAK class (Class 1) and the pIKE class (Class 2). Both classes contained the Lac repressor (lacI) in conjunction with the Ptrc-2 promoter for the first promoter-repressor pair. For the second promoter-repressor pair, the pTAK plasmids (Class 1) contained the $P_L S1$ con promoter in conjunction with a temperature-sensitive mutant of the $\lambda$ repressor (cIts). The pTAK plasmids were switched between states by a pulse of IPTG or by a thermal pulse. For the second promoter-repressor pair, the pIKE plasmids (Class 2) contained the $P_L$tetO-1 constitutive promoter in conjunction with the TetR repressor (tet R). The pIKE plasmids were switched between states by a pulse of IPTG or a pulse of anhydrotetracycline (aTc). In total, four variants of the pTAK based toggles and two variants of the pIKE based toggles were constructed and tested herein.

Plasmids were constructed using basic molecular cloning techniques described in standard cloning manuals [Ausubel et al. in *Current Protocols in Molecular Biology* (Wiley, New York, 1987); Sambrook et al. in *Molecular Cloning: A Laboratory Manual* (Cold Spring Harbor Laboratory Press, Plainview, N.Y., 1989)]. Restriction enzymes were purchased from New England Biolabs and Promega; PfuTurbo polymerase was purchased from Stratagene; all other enzymes were purchased from New England Biolabs; all synthetic oligonucleotides were purchased from Operon Technologies. All genes, promoters and transcription terminators were obtained by PCR amplification using PfuTurbo proofreading polymerase and synthetic primers with overhanging ends containing the appropriate restriction sites. Ribosome binding sites were included in the overhanging ends of the primers. Site mutations were performed using either the Stratagene QuickChange or ExSite protocols in accordance with the manufacturers instructions.

Genes, promoters and transcription terminators were obtained as follows: Ptrc-2 from pTrc99a (AP Biotech), $P_L$ from pXC46 (ATCC), $P_L$tetO-1 by total synthesis according to the published sequence [Lutz & Bujard (1 997) Nucleic Acids Res. 25:1203–1210], lacI from pTrc99a, cIts from pGW7 (ATCC), tetR from pcDNA6/TR (Invitrogen), gfuv from pGFPuv (Clontech), gapmut3 from pJBAI11 (gift of J. B. Andersen, Technical University of Denmark), and rrnT1T2 terminators from pTrc99a. All plasmids contained the ampicillin resistance region and ColEl origin of replication from the pTrc99a plasmid. All cloning was performed by TSS transformation [Ausubel et al. in *Current Protocols in Molecular Biology* (Wiley, New York, 1987)] into either *E. coli* strain JM2.300 (CGSC), JC158 (CGSC), or TAP106 (ATCC). DNA sequencing was performed using a Perkin-Elmer ABI Prism 377 Sequencer.

In all toggle plasmids, the gfpmut3 reporter gene was arranged as the second cistron downstream of the Ptrc-2 promoter. Thus, transcription from Ptrc-2 (and repression of $P_1$) results in the expression of GFPmut3. For clarity, this state is termed the "high" state. The opposing state, in which $P_1$ is transcribed and Ptrc-2 is repressed, is termed the "low" state. Unless otherwise indicated, GFPmut3 is the reporter used in all plasmids. Gfpmut3, a mutant of wild-type GFP containing S65G and S72A substitutions, is optimized for flow cytometry [Cormack et al. (1996) Gene 173:33–38]. This mutant is approximately 50–70 times brighter than GFPuv when expressed in *E. coli* and assayed in a FACS-Calibur flow cytometer.

Figure 11A:
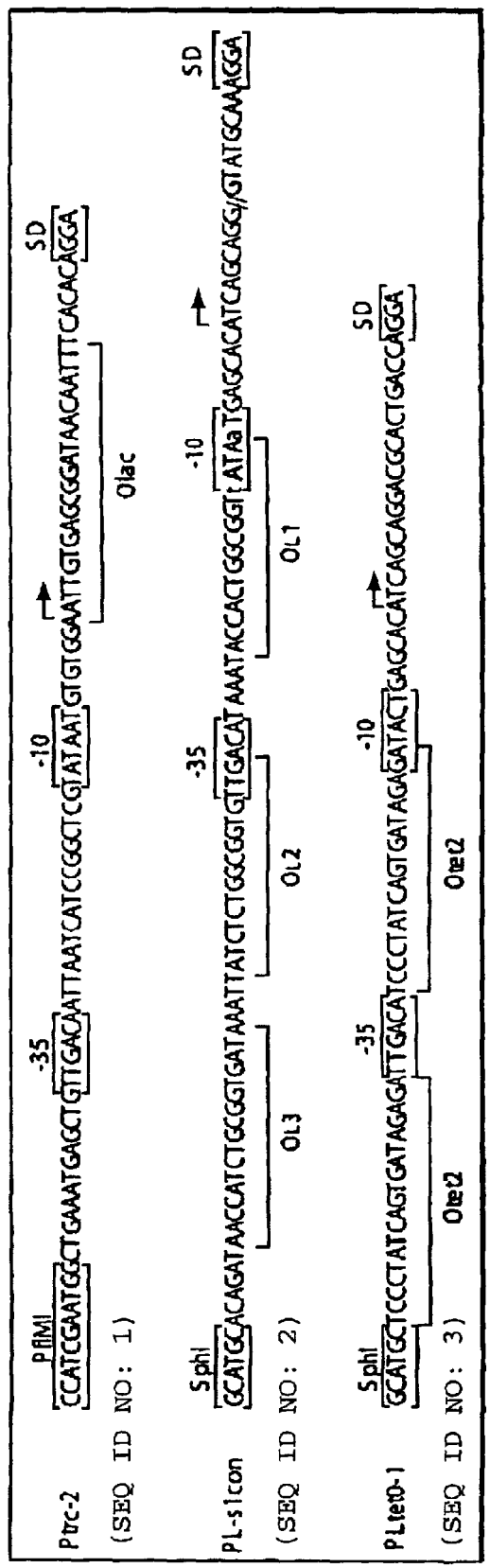

The promoters used in the toggle were $P_L$tetO-1 (TetR repressed), Ptrc-2 (LacI repressed) and $P_L$Slcon (CI repressed). The ranked order of the transcriptional efficiencies of the promoters is $P_L$Slcon>Ptrc-2>$P_L$tetO-1. In all variants of the toggle switch, the sequence of the three promoters was unchanged. The rates of synthesis of the repressors ($\alpha_1$ and $\alpha_2$ in the model) or the reporter genes were modified by exchanging the downstream ribosome binding sites (RBS). The structures of the three promoters and the various ribosome binding sites used in the toggle switches are illustrated in FIGS. 11A and B, respectively (SEQ ID NOs: 1–11). In FIG. 11A, the upstream limit of each promoter is marked by the indicated restriction site. Operator sites are marked by a single underbracket. The initiation of transcription is denoted with arrows. SD denotes the Shine-Dalgarno sequence. Mutations in the −10 sequence of $P_L$slcon are indicated with lowercase letters. In FIG. 11B, the Shine-Dalgarno sequences "AGGA" and start codons "ATG" are included. The various sequences are ranked in order of their translational efficiency (A being the highest, H being the lowest).

Bases −48 to +27 of the Ptrc promoter, where +1 is the initiation of transcription, were amplified by PCR from pTrc99a to form the Ptrc-2 promoter. Ptrc-2 is a highly efficient fusion of the Ptrp and Plac promoters and is nearly identical to the commonly used Ptac promoter. $P_L$Slcon is a shortened version of the wild-type $P_L$ promoter with additional mutations conferring a consensus −10 sequence. $P_L$Slcon was amplified from bases −75 to the Shine-Dalgarno sequence of pXC46. Thus $P_L$slcon eliminates the $P_{L2}$ secondary promoter and the L1 and L2 integration host factor binding sites of the wild-type $P_L$promoter [Giladi et al. (1992) J. Mol. Biol. 224:937–948]. Elimination of $P_{L2}$, L1, L2 and introduction of the −10 mutations serve to weaken the native strength of the extremely strong $P_L$ promoter while retaining all three operators for λ repressor binding. The $P_L$tetO-1 promoter, obtained through total synthesis according to the published sequence [Lutz & Bujard (1997) Nucleic Acids Res. 25:1203–1210], contains two copies of the $O_2$ operator of the TnIO tetracycline resistance operon—one between the consensus −35 sequence and the −10 sequence of $P_L$, and one upstream of the −35 sequence. The $P_L$tetO-1 promoter was substantially less efficient than both Ptrc-2 and $P_L$slcon, but it was effectively repressed by the wild-type TetR repressor.

Sequences of the promoter, repressor, and reporter genes for the following plasmids are shown in the attached Sequence Listing.

TABLE 3

Plasmids pTAK117 (SEQ ID NO: 12), pTAK131 (SEQ ID NO: 13), pTAK132 (SEQ ID NO: 14). Toggle location (nucleotides): 11–1630 plus 4407–6067 of SEQ ID NOs: 12–14.

| Feature Name | Feature Type | Location (nucleotides) |
|---|---|---|
| Ptrc | Promoter | 11–98 |
| CI | Repressor gene | 99–714 |
| GFP | Reporter gene | 914–1630 |
| PLslcon | Promoter | 5496–6067 (complementary strand) of SEQ ID NO: 12; 5499–6067 (complementary strand) of SEQ ID NOs: 13–14 |
| LacI | Repressor gene | 4407–5489 (complementary strand) |

TABLE 4

Plasmids pTAK130 (SEQ ID NO: 15). Toggle location (nucleotides): 11–1630 plus 4407–6069 of SEQ ID NO: 15.

| Feature Name | Feature Type | Location |
|---|---|---|
| Ptrc | Promoter | 11–98 |
| CI | Repressor gene | 99–714 |
| GFP | Reporter gene | 914–1630 |
| PLslcon | Promoter | 5499–6069 (complementary strand) |
| LacI | Repressor gene | 4407–5489 (complementary strand) |

TABLE 5

Plasmids pIKE105 (SEQ ID NO: 16), pIKE107 (SEQ ID NO: 17). Toggle location (nucleotides): 11–1549 plus 4326–5506 of SEQ ID NOs: 16–17.

| Feature Name | Feature Type | Location |
|---|---|---|
| Ptrc | Promoter | 11–98 |
| TetR | Repressor gene | 108–731 |
| GFP | Reporter gene | 833–1549 |
| PtetO-1 | Promoter | 5418–5503 (complementary strand) of SEQ ID NO: 16; 5418–5506 (complementary strand) of SEQ ID NO: 17 |
| LacI | Repressor gene | 4326–5408 (complementary strand) | ii. Strains, Growth Conditions, Chemicals

The host cell for all promoter assays and toggle switch experiments was *E. coli* strain JM2.300 [λ-, lacI22, rpsL135 (StrR), thi-1] (CGSC strain 5002). JM2.300, which contains few mutations and is a fast growing strain that can tolerate enormous overexpression of plasmid-bound genes. Because JM2.300 contains no λ repressor and carries a non-functional Lac repressor (lacI22), it is considered to be a suitable host for the toggle switch.

All cells were grown in LB medium (Difco) with 100 μg/ml ampicillin plus inducers as indicated in the text. All Type I and pIKE series plasmids were grown at 37±1° C., unless otherwise indicated. All pTAK series plasmids were grown at 32±1° C. except during thermal induction. Thermal induction was carried out at 42±1° C., unless otherwise indicated. For all expression tests, cells were maintained in logarithmic growth phase by periodic 500–1000 fold dilution into fresh medium.

Ampicillin and IPTG were purchased from Sigma Anhydrotetracycline was purchased from ACROS Organics. All other chemicals were obtained from Fisher.

iii. Assay of Gene Expression and Promoter Strength

The following expression data was collected using a Becton-Dickinson FACSCalibur flow cytometer with a 488 nm argon excitation laser and a 515–545 nm emission filter. Prior to each assay, cells were pelleted and resuspended in 0.22 μm filtered phosphate buffered saline (58 mM $Na_2HPO_4$, 17 mM $NaH_2PO_4$, 68 mM NaCl, pH=7.4). Cells were assayed at low flow rate and fluorescence was calibrated using InSpeck Green fluorescent beads (Molecular Probes). All measurements of gene expression were obtained from three independent cultures maintained simultaneously under identical conditions. For each culture, 40,000 events were collected. All flow data were converted to ASCII format using MFI (E. Martz, University of Massachusetts, Amherst, available at http://marlin.bio.umass.edu/mcbfacs/flowcat.html\##mfi) and analyzed with Matlab (Mathworks).

The strengths, in calibrated fluorescence units, of the promoter/RBS pairs used to construct the toggle switches are listed in Table 6. Measurements of promoter strengths were performed using Type I plasmids (FIG. 10A) and assays were performed as described above. Leakage expression from the promoters under filly repressed conditions is also listed in Table 6.

TABLE 6

Gene Expression by Plasmids

| PLASMID | TYPE | P1 | RBS1 | RBS2 | GFP EXPRESSION |
|---|---|---|---|---|---|
| Bare Promoters | | | | | |
| pMKN7a* | I | Ptrc-2 | E | — | 732 ± 108 |
| pBAG102 | I | $P_L$tetO-1 | C | — | 5.5 ± 0.1 |
| pBAG103 | I | $P_L$tetO-I | A | — | 660 ± 42 |
| pBRT21.1* | I | $P_L$slcon | D | — | 9,390 ± 840 |
| pBRT21.1*† | I | $P_L$slcon | D | — | 14,300 ± 400 |
| pBRT123 | I | $P_L$slcon | G | — | 387 ± 21 |
| pBRT124 | I | $P_L$slcon | F | — | 972 ± 43 |
| pBRT125 | I | $P_L$slcon | H | — | 15.9 ± 3.2 |
| LacI Repression | | | | | |
| pTAK102 | II | $P_L$slcon | D | — | 36.0 ± 3.8 |
| pTAK103a | II | $P_L$slcon | G | — | 137 ± 8 |
| cI Repression | | | | | |
| pTAK106 | III | $P_L$slcon | D | — | 2.5 ± 0.3 |
| pTAK107 | III | $P_L$slcon | G | — | 2.0 ± 0.1 |
| TetR Repression | | | | | |
| pIKE108 | III | $P_L$tetO-1 | A | — | 5.8 ± 1.0 |
| pIKE110 | III | $P_L$tetO-1 | C | — | 2.3 ± 0.2 |
| Toggles | | | | | |
| pTAK117 | IV | $P_L$slcon | D | B | Bistable |
| pTAK130 | IV | $P_L$slcon | G | B | Bistable |
| pTAK131 | IV | $P_L$slcon | F | B | Bistable |
| pTAK132 | IV | $P_L$slcon | H | B | Bistable |
| pIKE105 | IV | $P_L$tetO-1 | A | B | Monostable |
| pIKE107 | IV | $P_L$tetO-1 | C | B | Bistable |

*Estimated from flow-cytometer assay of GFPuv-expressing promoters.
†Grown at 32° C.

The efficacy of repression was tested using Type II plasmids (for LacI repression) (FIG. 10B) or Type III plasmids (for cI or TetR repression) (FIG. 10C). The efficiency of the three repressors, as used in the toggle switches can be estimated by comparing the strength of the bare promoters in Type I plasmids against their leakage expression under repressed conditions. For example, the extremely efficient λ repressor (cI), expressed from Ptrc-2-E, achieves ~6000 fold (14,300/2.5) repression of the $P_L$Slcon-D promoter (Table 6). On the other hand, the TetR repressor, also expressed from Ptrc-2-E, achieves only ~100 fold (660/5.8) repression of the $P_L$tetO-1-A promoter (Table 6).

iv. Demonstration of Bi-stability

In order to test the limits of bistability of the toggle switch, the a1 parameter was varied experimentally by inserting RBS1 sequences of varying efficiency into pTAK (Class 1) and pIKE (Class 2) toggle switches of Type IV. Four pTAK series plasmids (Class 1) were constructed with RBS1 sequences D,F,G and H, and two pIKE series plasmids (Class 2) were constructed with RBS1 sequences A and C (Table 6). All four pTAK plasmids exhibited bistability, while only one pIKE plasmid (pIKE107) exhibited bistability.

Figure 12A:
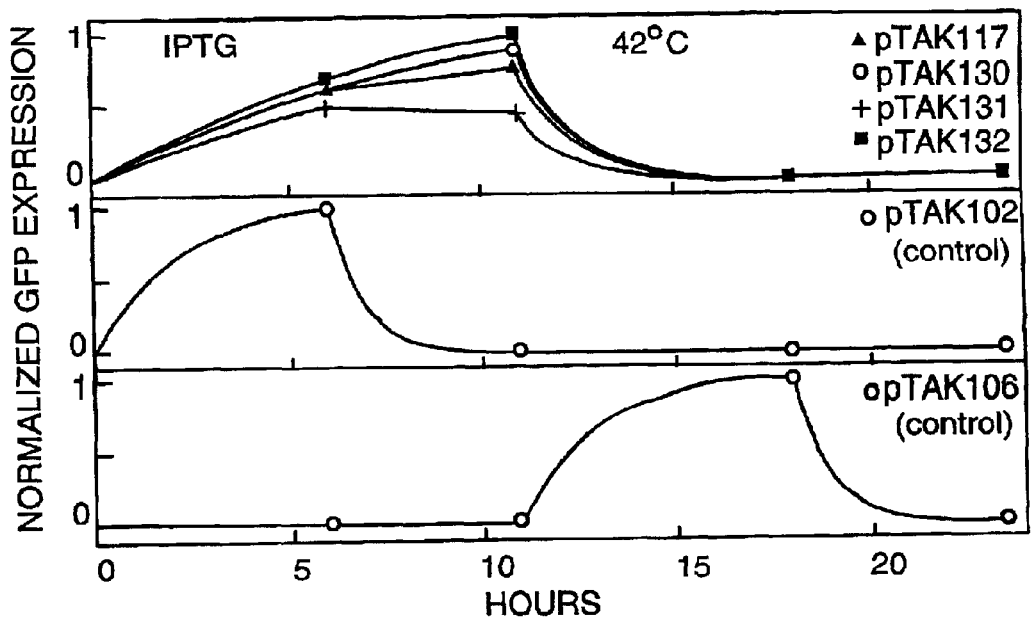
FIGS. 12A-C are graphs demonstrating bistability. The shading indicates times when the cells were grown in the presence or absence of switching agents.
Figure 12B:
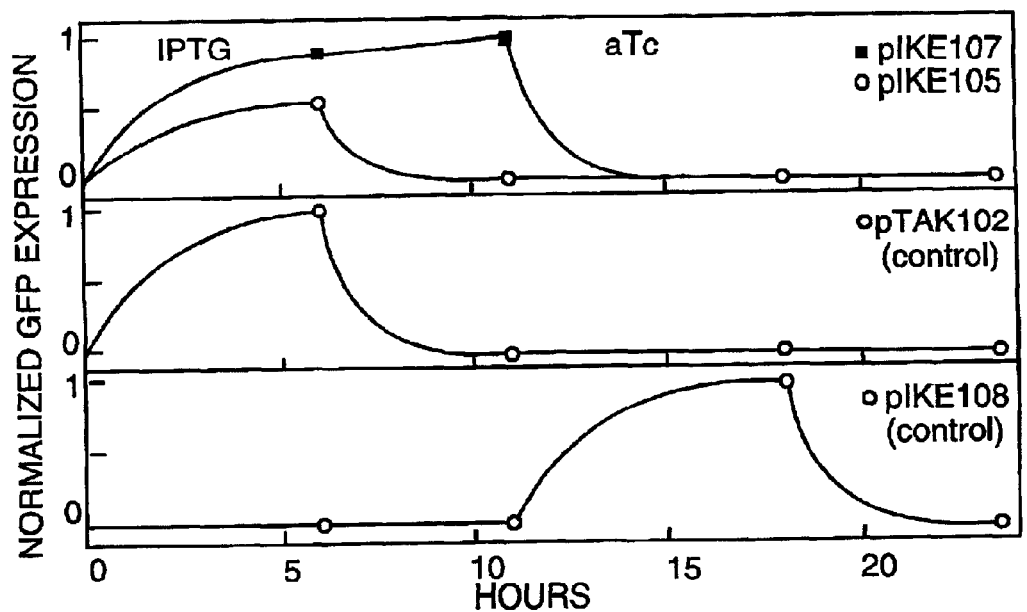

The existence of bistability is illustrated in FIG. 12. In this experiment, the toggle and control plasmids were grown in E. coli strain JM2.300 for 23.5 hours. At 6, 11, 18 and 23.5 hours, samples were taken and cells were pelleted, washed once in LB or PBS, and diluted 500–1000 fold into fresh medium with or without inducers as appropriate. Cells were initially grown for 6 hours with 2 mM IPTG, inducing GFPmut3 expression in all toggles and the IPTG-inducible pTAK102 control plasmid (FIG. 12A and B). The thermally-inducible pTAK106 control (FIG. 12A) and the aTc-inducible pIKE108 control (FIG. 12B) did not express GFPmut3 in the presence of IPTG. Cells were washed and diluted into fresh medium with no IPTG and grown an additional 5 hours. The five bistable toggle plasmids, which had been switched to the high state by the IPTG pulse, continued to express GFPmut3 in the absence of inducer, while the pTAK102 control plasmid and the monostable pIKE105 toggle plasmid, returned to the low state (FIGS. 12A and 12B). Cells were diluted into fresh medium and induced at 42° C. (pTAK plasmids only—FIG. 12A) or grown in the presence of 500 ng/ml aTc (pIKE plasmids only—FIG. 12B). After 7 hours growth, GFPmut3 expression in all toggles had been shut off, while GFPmut3 expression in the thermally-inducible pTAK106 control and the aTc-inducible pIKE108 control was up-regulated. Cells were washed and diluted into fresh medium with no inducers or returned to standard temperature. After an additional 5.5 hours, the five bistable toggle plasmids, which had been switched to the low state, continued to repress GFPmut3 expression, while the pTAK106 and pIKE108 controls returned, as expected, to their non-induced condition.

Figure 12C:
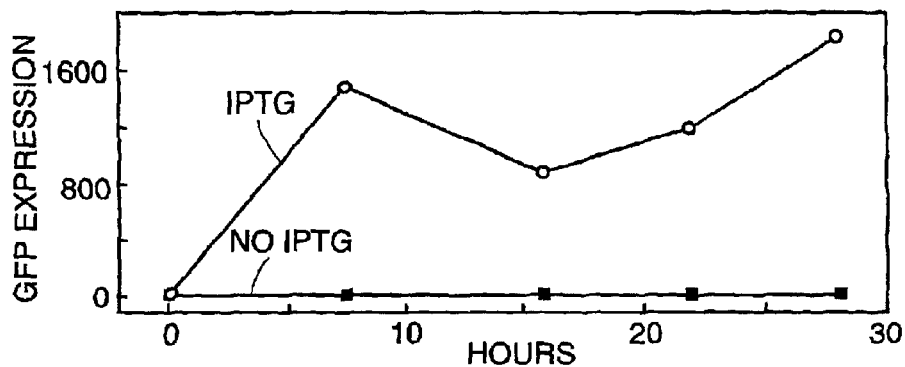

FIG. 12C shows the long-term stability of the two states of the pTAK117 toggle switch. In this experiment, a single culture of pTAK117 cells (initially in the low state) was divided into two groups and diluted. The first group was grown in medium with no inducers (squares) while the second group was grown in medium plus 2 mM IPTG (circles). After 6 hours, cells were pelleted, washed once in LB and diluted 1000 fold into fresh medium with no inducer. Both groups of cells were grown for an additional 22 hours while taking samples and diluting into fresh medium every 6–8.5 hours. The two groups of pTAK117 cells remained in their initial high or low states for the entire 22 hour period.

Although all of the toggle plasmids contained the same configuration of elements, one plasmid, pIKE105, did not exhibit bistability. Without wishing to be bound by theory, this result probably is due to the reduced efficiency of the TetR repressor relative to the λ repressor, and may be explained by reference to FIG. 13. To maintain bistability, the reduced efficiency requires a corresponding decrease in the strength of the $P_L$tetO-1 promoter relative to the $P_L$Slcon promoter. The $P_L$tetO-1 in the pIKE105 plasmid apparently is not sufficiently reduced in strength to achieve bistability. However, the strength reduction provided by the $P_L$tetO-1 promoter in the pIKE107 plasmid is sufficient.

Figure 13:
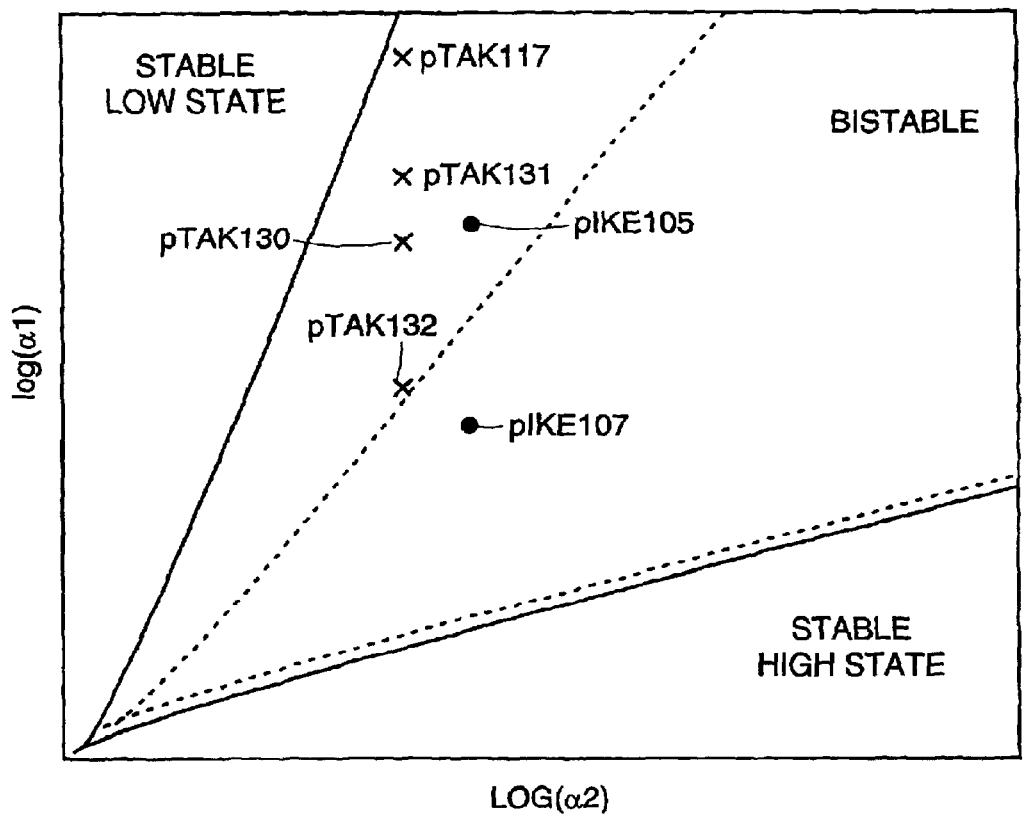
FIG. 13 is a schematic representation of the proposed structure of the bistable regions for the Class 1 (pTAK) and Class 2 (pIKE) toggle switches.

In FIG. 13, the Class 1 bifurcation region and toggles are denoted by continuous lines and crosses, respectively. The Class 2 bifurcation region and toggles are denoted by hatched lines and circles, respectively. The positions of the bifurcation curves and plasmids are qualitative estimates. The pTAK series plasmids contain the λ repressor, which dimerizes and binds cooperatively to three operator sites, and the Lac repressor, which forms a tetramer before binding to its operator site. Thus, both repressors should exhibit high cooperativity in the repression of their corresponding promoters (both β and λ are large) and hence, produce a broad bistable region. The pTAK117 plasmid, with the extremely strong $P_L$slcon-D promoter, likely exists somewhere near the edge of the bistable region. All other pTAK toggles contain weaker $P_L$Slcon promoters. Thus, the effective rate of Lac repressor synthesis ($\alpha_1$) was reduced and the toggles were shifted closer to the center of the bistable region.

The pIKE105 toggle, which contains the weaker $P_L$tetO-1-A promoter, synthesizes Lac repressor at a lower rate than pTAK117. At the same time, $\alpha_2$ was increased moderately because the TetR repressor was shorter, and thus more efficiently transcribed, and more tightly binding to its operator sites ($K_d \sim 10^{-11}$M for TetR to Otet2 [Hillen & Berens (1994) Annu. Rev. Microbiol. 48:345–369] versus $K_d \sim 10^{-9}$for λto $O_{L1}$–$O_{L3}$ [Johnson et al. (1981) Nature 294:217–223) the pIKE105 toggle could be expected to move further into the bistable region. However, the TetR dimer binds non-cooperatively to only two operator sites, while the λ dimer binds cooperatively to three operators. Thus, the exponent γ was reduced, the bistable region narrowed. The pIKE105 plasmid falls in the region of low state monostability. When the strength of the $P_L$tetO-1 promoter was reduced by replacing RBS-A with RBS-C, as in pIKE107, the value of $\alpha_1$ was reduced and the plasmid shifted back into the bistable region thereby generating bistability.

v. Generation of "Perfect" Switching Thresholds

The ideal switching threshold, or bifurcation, in the pTAK117 toggle switch is illustrated both theoretically and experimentally in FIG. 14.

Figure 14A:
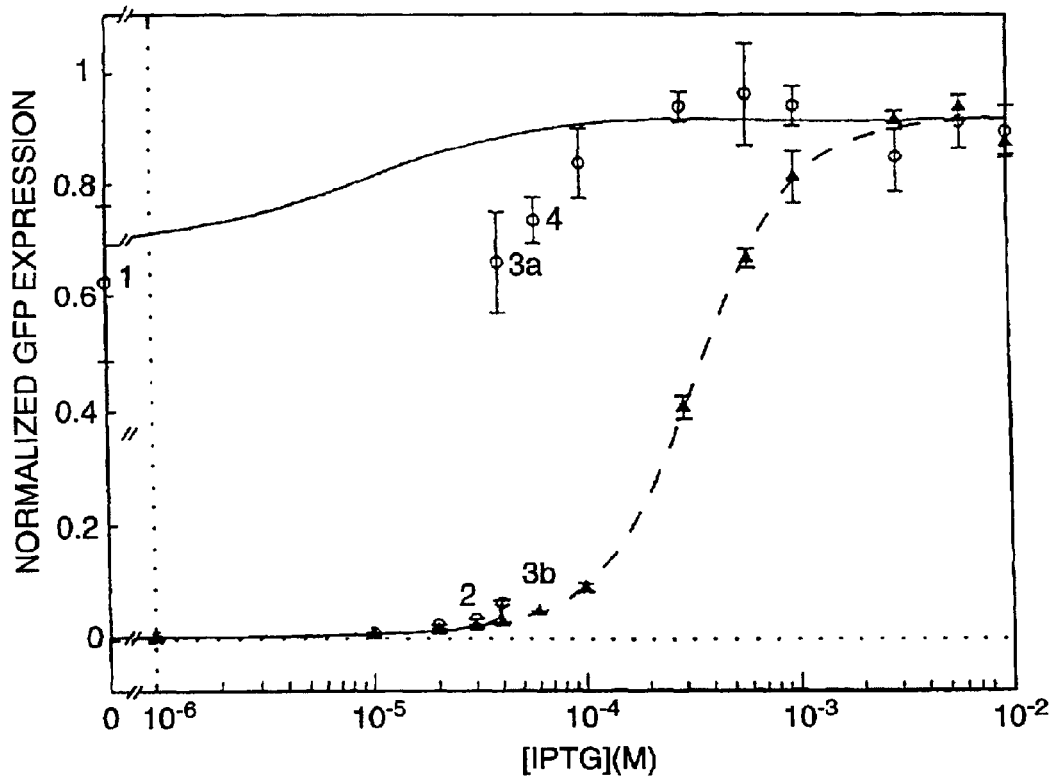
FIGS. 14A-C are graphs showing the toggle switch induction threshold.

FIG. 14A shows the steady-state gene expression after 17 hour induction. This was tested experimentally. In this experiment, pTAK117 (initially in the low state) and pTAK102 (as a control) were grown in 13 different concentrations of IPTG for 17 hours, diluting twice (at 6 and 12.5 hours) into fresh medium with the same IPTG concentration. The cells were grown for this length of time in order to ensure that they reached steady-state expression levels. The pTAK117 toggle plasmid (circles) exhibits a quasi-discontinuous jump to the high state whereas the pTAK102 control plasmid (triangles) exhibits a sigmoidal induction curve. Point 1 was taken from separate experiments measuring the high state of pTAK117 with no inducer. Points 3a and 3b are the high and low modes of a bimodally distributed cell population. The bimodality occurred apparently due to natural fluctuations in gene expression and the close proximity of the toggle switch to its bifurcation point. Induction of the pTAK102 control has the familiar sigmoidal shape (triangles). In contrast, the pTAK117 toggle follows the induction curve of pTAK102 up to an IPTG concentration of 40 μM, at which, point it exhibits a quasi-discontinuous jump to the high expression state (circles). This discontinuity is referred to as a saddle-node bifurcation.

Theoretical curves were calculated from equations (iii) and (iv) with the term $\hat{u}/(1+[RPTG]/K)^{72}$, where K is the dissociation constant of IPTG from LacR and η is the cooperativity of IPTG binding, replacing a in the denominator of equations (iv). The solid line curve shows the stable steady-states, and the dotted line curve shows the unstable steady-state of the toggle. The dashed curve shows the steady-state of the IPTG-inducible control plasmid. Model parameters for the theoretical curves were: $\alpha_1$=156.25, $\alpha_2$=15.6, β=2.5, γ=1, η=2.0015, K=2.9619×$10^{-5}$.

Figure 14B:
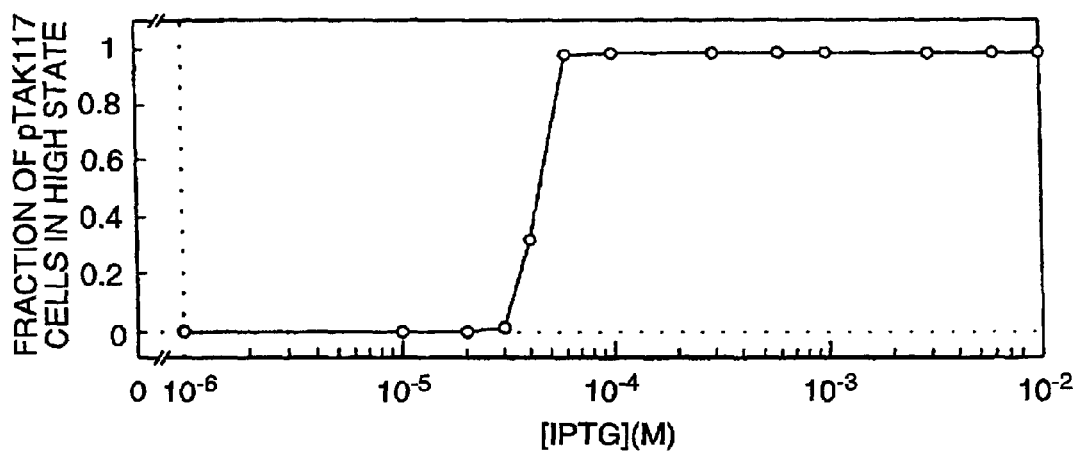
Figures 3, 14C:
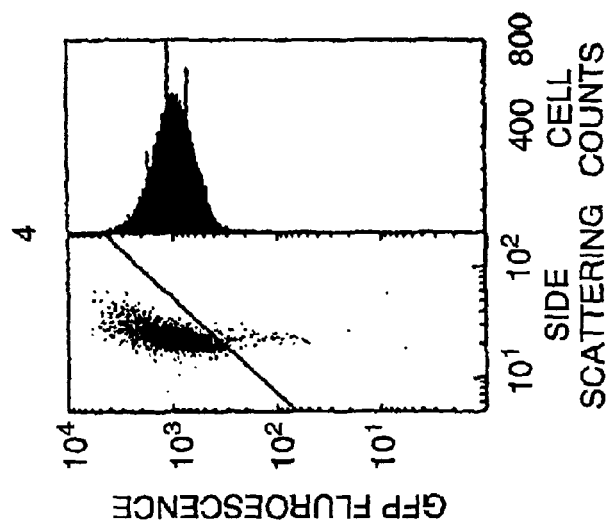
Figures 2, 14C:
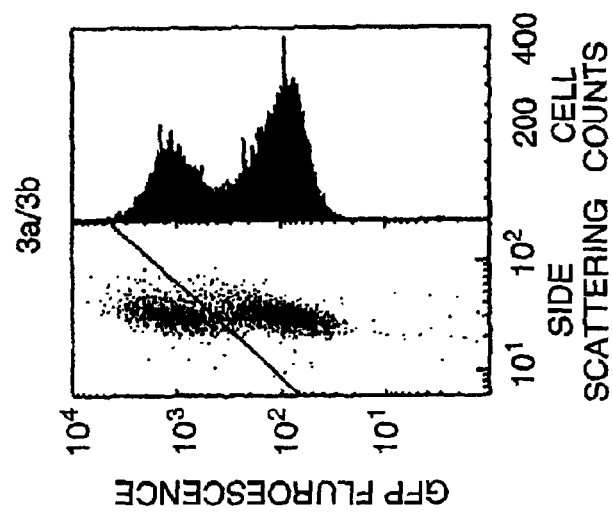
Figures 1, 14C:
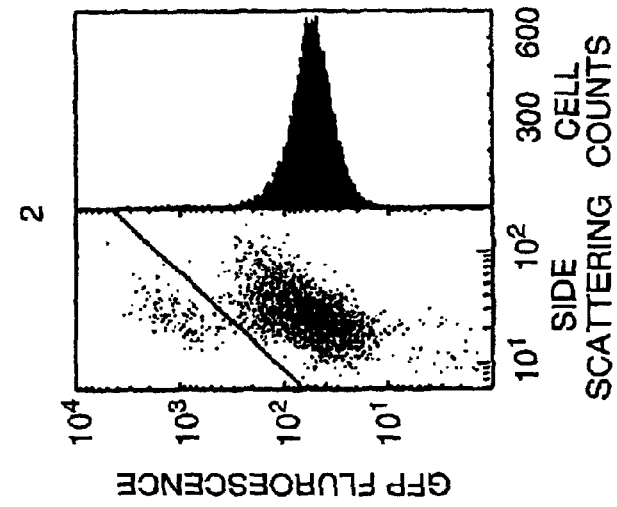

FIG. 14B shows the fraction of toggle cells in the high state at various concentrations of IPTG. The sudden switching to the high state is clearly visible. FIG. 14C shows scatter plots (left plots) and histograms (right plots) illustrating the condition of the toggle cells at points 2, 3 and 4 (of FIG. 14A) near the bifurcation point. High-state and low-state cell populations were divided by the line in the scatter plots. The two states of the toggle are clearly evident in the bimodally distributed cells (see, point 3a/3b data).

Due to the natural fluctuations in gene expression, the bifurcation was not a perfect discontinuity as predicted by the deterministic toggle equations. The stochastic nature of gene expression causes variability in the location of the switching threshold and thus blurred the bifurcation point. Near the bifurcation point, the blurriness was realized as a bimodal distribution of cells (FIG. 14C).

vi. Switching Time

Figure 15A:
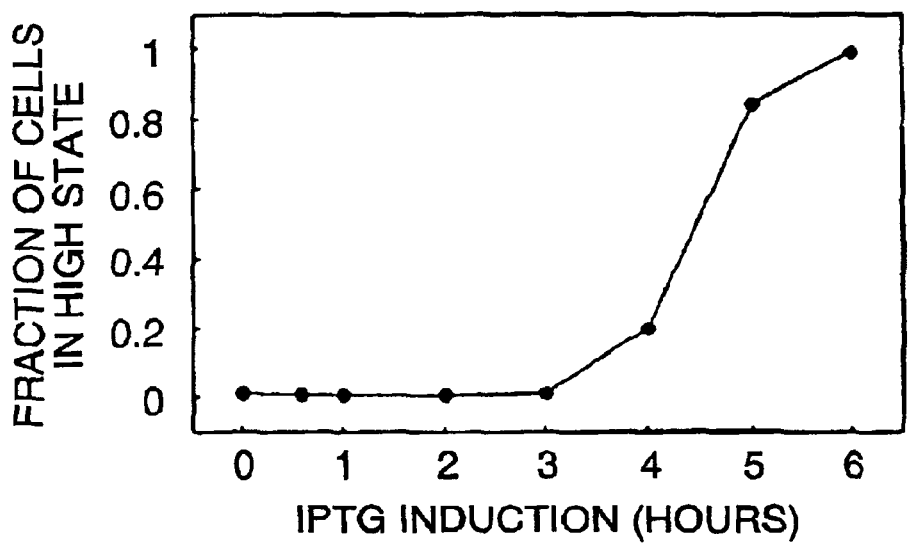
FIGS. 15A-C are graphs showing the switching time of the exemplary pTAK117 toggle switch.

The switching time of the pTAK117 plasmid from the low to high states and from the high to low states are illustrated in FIGS. 15A and B, respectively.

Figure 15B:
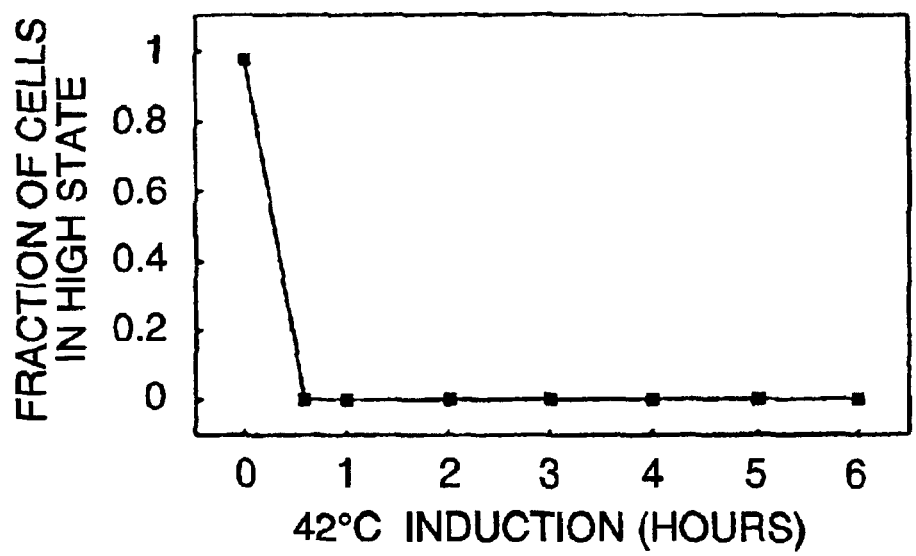

In this experiment, pTAK117 cells initially in the low state were diluted in fresh medium and induced with 2 mM IPTG. Separate cultures were grown for 35 minutes to 6 hours before pelleting, washing, and diluting the cells 500 fold in fresh medium with no inducer. Growth was continued until 10.25 hours after the start of the experiment and cells were assayed in the flow cytometer. The fraction of cells in the high state as a function of the induction time after IPTG induction is shown in FIG. 15A. Conversely, pTAK117 cells initially in the high state were diluted in fresh medium with no inducer. Separate cultures were grown at 41±1° C. for 35 minutes to 6 hours before diluting the cells 500 fold in fresh medium with no inducer. Growth was continued at standard temperature until 10.25 hours after the start of the experiment and cells were assayed in the flow cytometer. The fraction of cells in the high state as a function of the induction time after temperature induction is shown in FIG. 15B.

Figures 1, 15C:
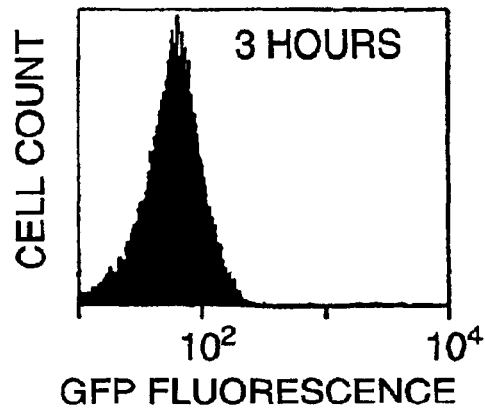
Figures 2, 15C:
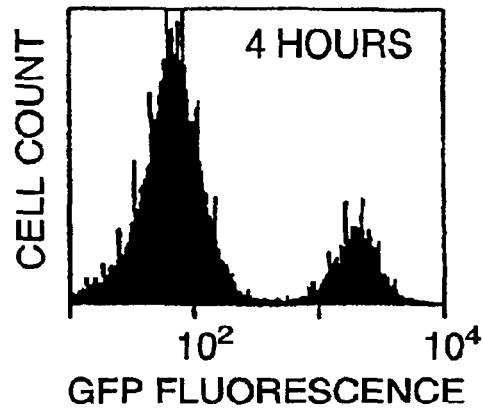
Figures 3, 15C:
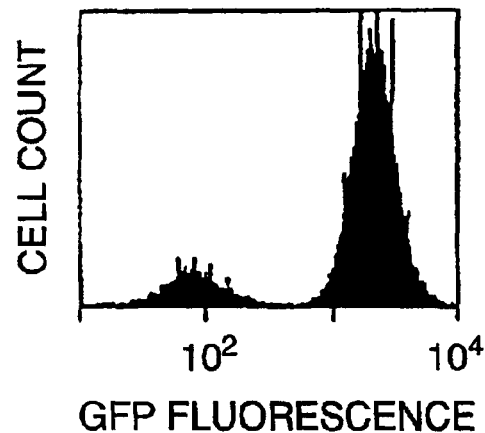
Figures 4, 15C:
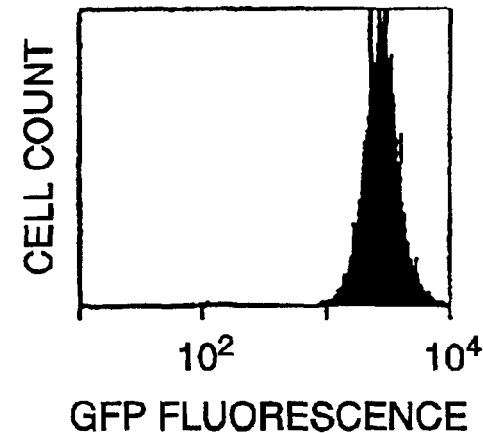

FIG. 15C shows switching of pTAK117 cells from the low to high state by IPTG induction. The cell population at four time points is illustrated. As evidenced by the appearance of a bimodal distribution at 4 hours (FIG. 15C), the pTAK117 plasmid began switching to the high state between 3 and 4 hours of IPTG induction. By five hours, the switching was nearly complete. By six hours, the switching was complete (FIGS. 15A and 15C). On the other hand, switching from the high state to the low state was completed in 35 minutes or less (FIG. 15B). In this experiment, the primary determinant of switching time appears to be the rate of destruction of the expressed transcribed repressor protein. The concentration of initial repressor must be reduced sufficiently to allow the system to cross into the basin of attraction of the ail opposing stable state.

Switching from low to high apparently requires gradual dilution, by cell growth, of the IPTG-based Lac repressor.

Since doubling time of the JM2.300 cells, when expressing in the high state, was 38 minutes, the switching time from low to high was on the order of hours. On the other hand, switching from high to low was accomplished by immediate thermal destabilization of the temperature-sensitive λ repressor. Thermal denaturation of the λ repressor was on the order of a few minutes. Thus, switching to the low state was substantially more rapid than switching to the high state. Furthermore, the configuration of the pTAK117 plasmid (the rate of Lac repressor synthesis was more than an order of magnitude higher than the rate of λ repressor synthesis) suggests that the low state was more stable (i.e., it has a larger basin of attraction) than the high state.

Example 4

Design Considerations for Construction of a Plasmid Carrying an Exemplary Toggle Switch that Functions in Mammalian Cells i. Design Considerations A mammalian genetic toggle switch may be constructed as described herein. A preferred mammalian system is similar to the pTAK and pIKE bacterial toggle switches described above: (i) the entire system is contained on a single plasmid; (ii) the two constitutive promoter-driven transcription units lie back to back in opposite orientation; and (iii) the repressor genes are arranged in bi-cistronic transcription units with the reporter genes (or other genes to be controlled). This design may be selected for the following reasons.

First, as suggested by mathematical modeling studies of the toggle switch and experimental results from the bacterial toggle switch, balanced promoter/repressor strengths are preferred for bistability. Promoter strength and repressor binding affinity can be controlled CO through proper selection or modification of these elements in order to achieve this balance. However, if the two promoter/repressor transcription units are separately transfected, they may integrate in different copy numbers and at different loci and thus disrupt the balance. To avoid a such a problem, both transcription units may be placed on a single vector. Moreover, the single vector design minimizes inconsistent results observed in existing two-plasmid expression systems. In addition, the single vector design requires only a single transfection to deliver the switch into a cell of interest and thus improves the switch's usability.

Second, although the back to back configuration of the transcription units is not necessary to achieve bistability, it minimizes the potential for unintended gene expression due to transcriptional read-through.

Third, although multiple configurations may be used to achieving regulation of a gene of interest using the toggle switch construct, this design places the gene of interest as the second cistron downstream of the one of the repressors. This configuration provides similar advantages to those stated above: it permits the use of a single expression construct and will likely improve the consistency of experimental results by minimizing differential copy number and chromatin effects on gene expression. In addition, the use of different internal ribosome entry sites (IRES) provides a means to separately adjust the expression strengths of genes for the toggle proteins and the expression strength of the gene of interest.

A. Component Selection

The mammalian genetic toggle switch requires the integration of multiple cis and trans regulatory elements into a single system. Suitable elements may be identified from gene databases and scientific literature. Candidate elements for use in an exemplary toggle switch are described below.

Promoters. The CMV immediate early promoter and the RSV-LTR promoter may be chosen, because they are strong constitutive promoters of similar strength and widely transcribed in a variety of cell types. Both promoters may be obtained from commercially available expression plasmids. Additional promoter candidates include EF-1α, SV40, UBC, HSVtk, and β-actin, though many other candidates may be easily identified in genomic databases. In principle, the same promoter may be utilized for both transcriptional units so long as it is modified with different operator sites (see below). However, it may be desirable to use two distinct promoters in order to minimize complications due to possible homologous recombination.

Operator sites. Operator sites preferably are inserted upstream, downstream, or within the constitutive promoter sequence such that binding by cognate repressor proteins modulates transcription. Initially, it may be possible to employ commercial constructs in which operator sites are already installed and tested; the operators in such constructs enable efficient binding and repression. If initial operator-promoter constructs do not work as intended, adjustments may be made to achieve desired properties. Previous work has demonstrated that effective regulation of gene expression can be attained if the operator sites are either within the promoter sequence itself [Yao F, et al., Hum Gene Ther. 9:1939, 1998], or placed downstream of the promoter in the 5' UTR of the transcript or the first intron of the transcript [U.S. Pat. No. 5,589,392]. Although prior data suggests that placing operators within the promoter achieves tighter regulation, the second configuration (downstream operators) offers the advantage of modularity i.e., an alternative constitutive promoter may be easily swapped into the toggle without modifying the remainder of the toggle network. If necessary, both configurations may be tried. In addition, multiple operator sequences may be inserted into or around each promoter. The use of multiple operator sequences typically provides better repression than single operators and may enhance the cooperativity repression; a feature that is important to the creation of bistability. Repressor genes. Repressor proteins used in the toggle (i) must tightly bind their cognate operator sites to block transcription, (ii) must be inhibited by the application of an inducing compound, and (iii) must not interact with native DNA sequences in the host cell. These design parameters are most easily satisfied by proteins cloned from prokaryotic organisms. Several proteins such as LacI, TetR, and Pip have been successfully used in the past in inducible expression systems [U.S. Pat. No. 5,589,392; Gossen, M., et al., 1992 supra; Fussenegger, M. (2000) supra]. Thus, two of these proteins may be used in the exemplary toggle switch. Alternative repressors may be identified from genomic databases and screening.

Repressor domains. Repressor domains including KRAB, v-erbA, NeP1, which are cloned from eukaryotic transcription factors, may be fused to prokaryotic or other DNA-binding proteins to enhance the proteins' ability to repress transcription. This approach has been used in other gene regulation systems [Fussenegger, M. (2000) supra].

Internal Ribosome Entry Sites. Internal Ribosome Entry Sites (IRES) typically are cloned from viral genomes, though such sites have been identified in native mammalian mRNA transcripts. The most common IRES in use was cloned from ECMV and may be used in the mammalian toggle switch. However, this IRES is relatively long (600 bp). Thus, an alternate, shorter IRES may improve the compactness of the toggle. Candidates include the Hepatitis C Virus and GB Virus B IRES as well as recently identified synthetic IRES composed of short repeated RNA elements complementary to ribosomal RNA [Chappell S A, et al., Proc. Natl. Acad. Sci. USA, 97:1536,2000].

Nuclear Localization Signals. It may be necessary to attach nuclear localization signal (NLS) sequences to facilitate the translocation of repressor proteins into the nucleus. Use of NLS sequences may be particularly important if the repressor proteins are large. However, prokaryotic DNA-binding proteins have been used successfully in the past both with and without NLS sequences.

Transcriptional/Translational Enhancers. In order to adjust the expression strength of either transcription unit, it may be desirable to use transcriptional or translational enhancers such as the CMV enhancer sequence, the UTR of VEGF, or the rabbit β-globin intron.

B. Vector Delivery

Transient transfection protocols (for example, DEAE-Dextran or lipofection) may be used for all testing of intermediate plasmid constructs used to build the mammalian toggle switch. Such protocols are simple and achieve sufficient transient transfection efficiencies for experiments. Once the final toggle construct has been completed, stable clones may be selected from a calcium phosphate transfection or an electroporation in order to thoroughly test the bistability, reversibility, and performance of the toggle switch.

C. Reporter Genes and Assays

To facilitate the construction and testing of the exemplary toggle switch, three different reporter genes may be used: one for each of the switch's transcription units and one for a reference plasmid that will be used to normalize for transfection efficiency in the transient transfection experiments. For the reference plasmid, human growth hormone (hGH) may be used. For the toggle plasmid, two of the following three reporters may be used: vascular endothelial growth factor (VEGF), human hepatocyte growth factor (hHGF), and human placental growth factor (hPlGF). hGH is already available in a standard constitutive expression vector. VEGF, hHGF, and hPlGF may be cloned into the toggle switch as the first or second cistron in the toggle transcription units. Although other reporters may be used, the above reporters are desirable for two reasons. First, they are physiologically relevant and may be used directly in experiments after the toggle is completed. Second, they are all secreted proteins that can be easily assayed with minimal disruption to the cell using highly sensitive commercial Enzyme Linked ImmunoSorbant Assay (ELISA) kits. Thus, they are ideal for testing leakage expression from the toggle as well as for testing the toggle's switching kinetics. In addition, the toggle switch may be coupled to GFP reporter genes for assay on a flow cytometer. Though less sensitive than the ELISA assays, the flow cytometer will provide information on the distribution of cells between high and low states. Such information could be helpful in determining the robustness of the toggle switch to variability in gene expression.

D. Cell Types

One or more of several common cell types may be used to develop and test the toggle, including: HeLa, 3T3, COS, HEK 293, CHO and L929 cells. As a starting point, L929 cells may be used because they can be cloned from low density, exhibit efficient uptake of DNA, and have performed well in other experiments.

ii. Steps in the Toggle Switch Construction and Testing

The mammalian toggle switch may be constructed in a sequential process that permits controlled testing and validation of the performance of each component of the switch. The information gathered from the intermediate plasmids may be used to calibrate the performance of each element alone and integrated into the regulatory network of the toggle switch. This information may be used to help troubleshoot problems that may arise in the performance of the final toggle switch plasmid.

A. Step 1: Backbone Plasmid

The backbone plasmid is the core bacterial/mammalian cell shuttle vector into which all other elements of the toggle switch are inserted. The primary candidate for this vector is the pcDNA4/TO vector produced by Invitrogen Corporation. The plasmid contains the ampicillin and Zeocin resistance genes for bacterial and mammalian selection; it contains a CWV/TO promoter—a CMV promoter modified with operator sites for the TetR gene; and it contains a multiple cloning site and polyadenylation (pA) sequence downstream of the CMVITO promoter. Thus, it contains the core elements necessary for the first transcription unit. To make the plasmid suitable for further development, a second multiple cloning site may be added between the $AmP^R$ cassette and the CMV/TO promoter with sufficient unique restriction sites (~8 sites) to enable direct insertion of each element of the second transcription unit. In order to make the plasmid as compact as possible, sections of the backbone plasmid that contain unnecessary control sequences such as the f1 and SV40 origins of replication may be deleted.

B. Step 2: Promoter 1 Testing

First the hPlGF or hVEGF gene may be inserted into a first multiple claiming site (MCS) downstream of the CMV/TO promoter in the backbone plasmid to collect data on the unrepressed expression efficiency of the promoter using an ELISA kit. To test repression, this "step 2" plasmid may be transiently transfected together with a plasmid in which the TetR protein is constitutively expressed. Data may then be collected on the repressed expression efficiency of the CMV/TO promoter using an ELISA for hPlGF or hVEGF. Induction of expression of hPlGF or hVEGF in response to the application of tetracycline may also be examined.

C. Step 3: Promoter 2 Testing

A copy of the RSV-LTR/LO promoter coupled to the hHGF gene may be inserted into the second MCS in opposite orientation to the CMV/TO promoter. The RSV-LTR/LO promoter contains operator sequences for the LacI repressor within the RSV-LTR sequence and in a downstream intron. The unrepressed expression efficiency of the RSV-LTR promoter may be assayed using an ELISA for hHGF. hPlGF or hVEGF expression may be simultaneously assayed with hHGF to determine if the insertion of the RSV-LTR has positive or negative effects on expression efficiency of the CMV/TO promoter. To test repression, this "step 3" plasmid and a plasmid in which the LacI protein is constitutively expressed may be transiently transfected in order to collect data on the repressed expression efficiency of the RSV-LTR/LO promoter using an ELISA for hHGF. Induction of expression of hHGF in response to the application of IPTG may also be examined.

D. Step 4: Individual Repressor Testing

If the CMV/TO and RSV-LTR promoters function effectively and exhibit similar KO expression efficiencies, each repressor gene may then be inserted into a separate copy of the "step 3" plasmid. First the TetR gene may be placed downstream of the RSV-LTR/LO promoter along with a downstream IRES that enables simultaneous expression of the hHGF protein. The hVEGF or hPlGF protein may then be assayed to examine the repression efficiency of the TetR protein when expressed from the RSV-LTR/LO promoter. Induction of expression of hVEGF or hPlGF in response to the application of tetracycline may also be examined.

Second, the LacI gene may also be placed downstream of the CMVITO promoter along with a downstream IRES that enables simultaneous expression of hVEGF or hPIGF. hHGF may then be assayed to examine the repression efficiency of the LacI protein when expressed from the CMV/TO promoter. Induction of expression of hHGF in response to the application of IPTG may also be examined. If suitable repression and induction is observed with both plasmids, the toggle switch plasmid may be constructed as in Step 5.

E. Step 5: Toggle Switch Construct Testing

Finally, both plasmids constructed in Step 4 may be combined to create the toggle switch plasmid. In order to test the plasmid, it may be stably transfected into a host cell. The existence of two stable and switchable expression states of the toggle switch may then be demonstrated by transiently introducing tetracycline into the culture medium to switch it into its first stable expression state and then transiently introducing IPTG into the culture medium to switch it into its second stable expression state.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

Incorporation by Reference

Each of the patent documents and scientific publications disclosed herein is incorporated by reference into this application in its entirety.

What is claimed is:

1. A recombinant bistable genetic toggle switch that is capable of being stable in a first state or in a second state in the absence of a switching agent, the toggle switch comprising:

(a) a first nucleic acid construct comprising a first promoter operably associated with a first gene encoding a first repressor protein, wherein transcription from the first promoter is active in the absence of a repressor; and (b) a second nucleic acid construct comprising a second promoter operably associated with a second gene encoding a second repressor protein, wherein transcription from the first promoter is active in the absence of a repressor, and wherein the second repressor protein, when produced, is capable of repressing transcription from the first promoter, and wherein repression of the first promoter by the second repressor protein is reducible by a first switching agent, and wherein the first repressor protein, when produced, is capable of repressing transcription from the second promoter, and wherein repression of the second promoter by the first repressor protein is reducible by a second switching agent, and wherein components of the bistable genetic toggle switch are selected so that the first switching agent causes the toggle switch to switch from a second stable state to a first stable state and the second switching agent causes the toggle switch to switch from a first stable state to a second stable state.

2. The toggle switch of claim 1, wherein repression of the first promoter by the second repressor is reduced by the first switching agent such that transcription of the first gene by the first promoter is derepressed thereby causing the toggle switch to be in the first state.

3. The toggle switch of claim 2, wherein transcription of the first gene by the first promoter is derepressed by transient application of the first switching agent.

4. The toggle switch of claim 1 or 2, wherein repression of the second promoter by the first repressor is reduced by the second switching agent such that transcription of the second gene by the second promoter is derepressed thereby causing the toggle switch to be in the second state.

5. The toggle switch of claim 4, wherein transcription of the second gene by the second promoter is derepressed by transient application of the second switching agent.

6. The toggle switch of claim 1, wherein the first construct further comprises a third gene encoding a protein of interest, wherein the third gene is in operable association with the first promoter.

7. The toggle switch of claim 6, wherein transcription of the third gene increases upon application of the first switching agent.

8. The toggle switch of claim 1 or 6, wherein the second construct further comprises a fourth gene encoding a protein of interest, wherein the fourth gene is in operable association with the second promoter.

9. The toggle switch of claim 8, wherein transcription of the fourth gene increases upon application of the second switching agent.

10. The toggle switch of claim 1, wherein the first and second constructs are comprised within a single contiguous nucleic acid sequence.

11. The toggle switch of claim 1, wherein the first promoter, the second promoter or both the first and second promoters are each in operable association with an operator.

12. An isolated host cell harboring the toggle switch of claim 1.

13. An isolated host cell harboring the toggle switch of claim 1, wherein the host cell is a prokaryotic cell.

14. The host cell of claim 13, wherein the prokaryotic cell is *Escherichia coli*.

15. The host cell of claim 12, wherein the host cell is a eukaryotic cell.

16. The host cell of claim 15, wherein the eukaryotic cell is a mammalian cell or a yeast cell.

* * * * *

SEQUENCE LISTING

<160> NUMBER OF SEQ ID NOS: 17

<210> SEQ ID NO 1
<211> LENGTH: 90
<212> TYPE: DNA
<213> ORGANISM: Artificial Sequence
<220> FEATURE:
<223> OTHER INFORMATION: Promoter Ptrc-2

<400> SEQUENCE: 1
ccatcgaatg gctgaaatga gctgttgaca attaatcatc cggctcgtat aatgtgtgga      60
attgtgagcg gataacaatt tcacacagga                                      90

<210> SEQ ID NO 2
<211> LENGTH: 102
<212> TYPE: DNA
<213> ORGANISM: Artificial Sequence
<220> FEATURE:
<223> OTHER INFORMATION: Promoter PL-s1con

<400> SEQUENCE: 2
gcatgcacag ataaccatct gcggtgataa attatctctg gcggtgttga cataaatacc      60
actggcggtt ataatgagca catcagcagg gtatgcaaag ga                        102

<210> SEQ ID NO 3
<211> LENGTH: 84
<212> TYPE: DNA
<213> ORGANISM: Artificial Sequence
<220> FEATURE:
<223> OTHER INFORMATION: Promoter Pltet0-1

<400> SEQUENCE: 3
gcatgctccc tatcagtgat agagattgac atccctatca gtgatagaga tactgagcac      60
atcagcagga cgcactgacc agga                                            84

<210> SEQ ID NO 4
<211> LENGTH: 15
<212> TYPE: DNA
<213> ORGANISM: Artificial Sequence
<220> FEATURE:
<223> OTHER INFORMATION: Ribosome Binding Site A

<400> SEQUENCE: 4

```
aggaggaaaa aaatg                                                15

<210> SEQ ID NO 5
<211> LENGTH: 13
<212> TYPE: DNA
<213> ORGANISM: Artificial Sequence
<220> FEATURE:
<223> OTHER INFORMATION: Ribosome Binding Site B

<400> SEQUENCE: 5
aggaatttaa atg                                                  13

<210> SEQ ID NO 6
<211> LENGTH: 15
<212> TYPE: DNA
<213> ORGANISM: Artificial Sequence
<220> FEATURE:
<223> OTHER INFORMATION: Ribosome Binding Site C

<400> SEQUENCE: 6
aggaaacaga ccatg                                                15

<210> SEQ ID NO 7
<211> LENGTH: 17
<212> TYPE: DNA
<213> ORGANISM: Artificial Sequence
<220> FEATURE:
<223> OTHER INFORMATION: Ribosome Binding Site D

<400> SEQUENCE: 7
aggaaaccgg ttcgatg                                              17

<210> SEQ ID NO 8
<211> LENGTH: 15
<212> TYPE: DNA
<213> ORGANISM: Artificial Sequence
<220> FEATURE:
<223> OTHER INFORMATION: Ribosome Binding Site E

<400> SEQUENCE: 8
aggaaaccgg ttatg                                                15

<210> SEQ ID NO 9
<211> LENGTH: 14
<212> TYPE: DNA
<213> ORGANISM: Artificial Sequence
<220> FEATURE:
<223> OTHER INFORMATION: Ribosome Binding Site F

<400> SEQUENCE: 9
aggacggttc gatg                                                 14

<210> SEQ ID NO 10
<211> LENGTH: 16
<212> TYPE: DNA
<213> ORGANISM: Artificial Sequence
<220> FEATURE:
<223> OTHER INFORMATION: Ribosome Binding Site G

<400> SEQUENCE: 10
aggaaaggcc tcgatg                                               16

<210> SEQ ID NO 11
<211> LENGTH: 14
<212> TYPE: DNA
```

<213> ORGANISM: Artificial Sequence
<220> FEATURE:
<223> OTHER INFORMATION: Ribosome Binding Site H

<400> SEQUENCE: 11
aggacggccg gatg                                                         14

<210> SEQ ID NO 12
<211> LENGTH: 6086
<212> TYPE: DNA
<213> ORGANISM: Artificial Sequence
<220> FEATURE:
<223> OTHER INFORMATION: Plasmid pTAK117

<400> SEQUENCE: 12

```
ccatcgaatg gctgaaatga gctgttgaca attaatcatc cggctcgtat aatgtgtgga      60
attgtgagcg ataacaatt  tcacacagga accggttat  gagcacaaaa aagaaaccat     120
taacacaaga gcagcttgag gacgcacgtc gccttaaagc aatttatgaa aaaagaaaa      180
atgaacttgg cttatcccag gaatctgtcg cagacaagat ggggatgggg cagtcaggcg     240
ttggtgcttt atttaatggc atcaatgcat taaatgctta taacgccgca ttgcttgcaa     300
aaattctcaa agttagcgtt gaagaattta gcccttcaat cgccagagaa atctacgaga     360
tgtatgaagc ggttagtatg cagccgtcac ttagaagtga gtatgagtac cctgttttt     420
ctcatgttca ggcagggatg ttctcacctg agcttagaac ctttaccaaa agtgatgcgg     480
agagatgggt aagcacaacc aaaaaagcca gtgattctgc attctggctt gaggttgaag     540
gtaattccat gaccgcacca acaggctcca agccaagctt tcctgacgga atgttaattc     600
tcgttgaccc tgaacaggct gttgagccag gtgatttctg catagccaga cttgggggtg     660
atgagtttac cttcaagaaa ctgatcaggg atagcggtca ggtgttttta caaccactaa     720
acccacagta cccaatgatc ccatgcaatg agagttgttc cgttgtgggg aaagttatcg     780
ctagtcagtg gcctgaagag acgtttggct gactgcagca taaataaccc cgctcttaca     840
cattccagcc ctgaaaaagg gcatcaaatt aaaccacacc tatggtgtat gcaaaggaat     900
ttaaatgggt accatgagta aggagaaga  acttttcact ggagttgtcc caattcttgt     960
tgaattagat ggcgatgtta atgggcaaaa attctctgtc agtggagagg gtgaaggtga    1020
tgcaacatac ggaaaactta cccttaaatt tatttgcact actgggaagc tacctgttcc    1080
atggccaaca cttgtcacta cttttcggtta tggtgttcaa tgctttgcga tacccagat    1140
tcatatgaaa cagcatgact ttttcaagag tgccatgccc gaaggttatg tacaggaaag    1200
aactatattt tacaaagatg acgggaacta caagacacgt gctgaagtca agtttgaagg    1260
tgatacccct gttaatagaa tcgagttaaa aggtattgat tttaaagaag atggaaacat    1320
tcttggacac aaaatggaat acaactataa ctcacataat gtatacatca tggcagacaa    1380
accaaagaat ggaatcaaag ttaacttcaa aattagacac aacattaaag atggaagcgt    1440
tcaattagca gaccattatc aacaaaatac tccaattggc gatggccctg tccttttacc    1500
agacaaccat tacctgtcca cacaatctgc cctttccaaa gatcccaacg aaaagagaga    1560
tcacatgatc cttcttgagt ttgtaacagc tgctgggatt acacatggca tggatgaact    1620
atacaaataa aagctagctt ggctgttttg gcggatgaga agatttttca gcctgatac     1680
agattaaatc agaacgcaga agcggtctga taaaacagaa tttgcctggc ggcagtagcg    1740
cggtggtccc acctgacccc atgccgaact cagaagtgaa acgccgtagc gccgatggta    1800
gtgtggggtc tccccatgcg agagtaggga actgccaggc atcaaataaa acgaaaggct    1860
```

-continued

```
cagtcgaaag actgggcctt tcgttttatc tgttgtttgt cggtgaacgc tctcctgagt   1920
aggacaaatc cgccgggagc ggatttgaac gttgcgaagc aacggcccgg agggtggcgg   1980
gcaggacgcc cgccataaac tgccaggcat caaattaagc agaaggccat cctgacggat   2040 ggccttttg cgtttctaca aactcttttt gtttatttt ctaaatacat tcaaatatgt    2100
atccgctcat gagacaataa ccctgataaa tgcttcaata atattgaaaa aggaagagta   2160
tgagtattca acatttccgt gtcgccctta ttcccttttt tgcggcattt tgccttcctg   2220
tttttgctca cccagaaacg ctggtgaaag taaaagatgc tgaagatcag ttgggtgcac   2280
gagtgggtta catcgaactg gatctcaaca gcggtaagat ccttgagagt tttcgccccg   2340
aagaacgttt tccaatgatg agcacttta aagttctgct atgtggcgcg gtattatccc   2400
gtgttgacgc cgggcaagag caactcggtc gccgcataca ctattctcag aatgacttgg   2460
ttgagtactc accagtcaca gaaaagcatc ttacggatgg catgacagta agagaattat   2520
gcagtgctgc cataaccatg agtgataaca ctgcggccaa cttacttctg acaacgatcg   2580
gaggaccgaa ggagctaacc gcttttttgc acaacatggg ggatcatgta actcgccttg   2640
atcgttggga accggagctg aatgaagcca taccaaacga cgagcgtgac accacgatgc   2700
ctacagcaat ggcaacaacg ttgcgcaaac tattaactgg cgaactactt actctagctt   2760
cccggcaaca attaatagac tggatggagg cggataaagt tgcaggacca cttctgcgct   2820
cggcccttcc ggctggctgg tttattgctg ataaatctgg agccggtgag cgtgggtctc   2880
gcggtatcat tgcagcactg gggccagatg gtaagccctc ccgtatcgta gttatctaca   2940
cgacggggag tcaggcaact atggatgaac gaaatagaca gatcgctgag ataggtgcct   3000
cactgattaa gcattggtaa ctgtcagacc aagtttactc atatatactt tagattgatt   3060
taaaacttca ttttaattt aaaaggatct aggtgaagat ccttttgat aatctcatga     3120 ccaaaatccc ttaacgtgag ttttcgttcc actgagcgtc agaccccgta gaaaagatca   3180
aaggatcttc ttgagatcct ttttttctgc gcgtaatctg ctgcttgcaa acaaaaaaac   3240
caccgctacc agcggtggtt tgtttgccgg atcaagagct accaactctt tttccgaagg   3300
taactggctt cagcagagcg cagataccaa atactgtcct tctagtgtag ccgtagttag   3360
gccaccactt caagaactct gtagcaccgc ctacatacct cgctctgcta atcctgttac   3420
cagtggctgc tgccagtggc gataagtcgt gtcttaccgg gttggactca agacgatagt   3480
taccggataa ggcgcagcgg tcgggctgaa cggggggttc gtgcacacag cccagcttgg   3540
agcgaacgac ctacaccgaa ctgagatacc tacagcgtga gctatgagaa agcgccacgc   3600
ttcccgaagg gagaaaggcg gacaggtatc cggtaagcgg cagggtcgga acaggagagc   3660
gcacgaggga gcttccaggg ggaaacgcct ggtatcttta tagtcctgtc gggtttcgcc   3720
acctctgact tgagcgtcga ttttttgtgat gctcgtcagg gggcggagc ctatggaaaa    3780 acgccagcaa cgcggccttt ttacggttcc tggccttttg ctggcctttt gctcacatgt   3840
tctttcctgc gttatcccct gattctgtgg ataaccgtat taccgccttt gagtgagctg   3900
ataccgctcg ccgcagccga acgaccgagc gcagcgagtc agtgagcgag gaagcggaag   3960
agcgagtttg tagaaacgca aaaaggccat ccgtcaggat ggccttctgc ttaatttgat   4020
gcctggcagt ttatggcggg cgtcctgccc gccaccctcc gggccgttgc ttcgcaacgt   4080
tcaaatccgc tcccgcggga tttgtcctac tcaggagagc gttcaccgac aaacaacaga   4140
taaaacgaaa ggcccagtct ttcgactgag cctttcgttt tatttgatgc ctggcagttc   4200
```

-continued

```
cctactctcg catgggaga ccccacacta ccatcggcgc tacggcgttt cacttctgag    4260
ttcggcatgg ggtcaggtgg gaccaccgcg ctactgccgc caggcaaatt ctgttttatc    4320
agaccgcttc tgcgttctga tttaatctgt atcaggctga aaatcttctc tcatccgcca    4380
aaacagccaa gcttacttaa ctgcagtcac tgcccgcttt ccagtcggga aacctgtcgt    4440
gccagctgca ttaatgaatc ggccaacgcg cggggagagg cggtttgcgt attgggcgcc    4500
agggtggttt ttcttttcac cagtgagacg ggcaacagct gattgccctt caccgcctgg    4560
ccctgagaga gttgcagcaa gcggtccacg ctggtttgcc ccagcaggcg aaaatcctgt    4620
ttgatggtgg ttaacggcgg gatataacat gagctgtctt cggtatcgtc gtatcccact    4680
accgagatat ccgcaccaac gcgcagcccg gactcggtaa tggcgcgcat tgcgcccagc    4740
gccatctgat cgttggcaac cagcatcgca gtgggaacga tgccctcatt cagcatttgc    4800
atggtttgtt gaaaaccgga catggcactc cagtcgcctt cccgttccgc tatcggctga    4860
atttgattgc gagtgagata tttatgccag ccagccagac gcagacgcgc cgagacagaa    4920
cttaatgggc ccgctaacag cgcgatttgc tggtgaccca atgcgaccag atgctccacg    4980
cccagtcgcg taccgtcttc atgggagaaa ataatactgt tgatgggtgt ctggtcagag    5040
acatcaagaa ataacgccgg aacattagtg caggcagctt ccacagcaat ggcatcctgg    5100
tcatccagcg gatagttaat gatcagccca ctgacgcgtt gcgcgagaag attgtgcacc    5160
gccgctttac aggcttcgac gccgcttcgt tctaccatcg acaccaccac gctggcaccc    5220
agttgatcgg cgcgagattt aatcgccgcg acaatttgcg acggcgcgtg cagggccaga    5280
ctggaggtgg caacgccaat cagcaacgac tgtttgcccg ccagttgttg tgccacgcgg    5340
ttgggaatgt aattcagctc cgccatcgcc gcttccactt tttcccgcgt tttcgcagaa    5400
acgtggctgg cctggttcac cacgcgggaa acggtctgat aagagacacc ggcatactct    5460
gcgacatcgt ataacgttac tggtttcata tgcatcgaac cggtttcctt tgcatacacc    5520
ataggtgtgg tttaatttga tgccctttt cagggctgga atgtgtaaga gcggggttat    5580
ttatgctgtt gttttttgt tactcgggaa gggctttacc tcttccgcat aaacgcttcc    5640
atcagcgttt atagttaaaa aaatctttcg gaactggttt tgcgcttacc ccaaccaaca    5700
ggggatttgc tgctttccat tgagcctgtt tctctgcgcg acgttcgcgg cggcgtgttt    5760
gtgcatccat ctggattctc ctgtcagtta gctttggtgg tgtgtggcag ttgtagtcct    5820
gaacgaaaac cccccgcgat tggcacattg gcagctaatc cggaatcgca cttacggcca    5880
atgcttcgtt tcgtatcaca caccccaaag ccttctgctt tgaatgctgc ccttcttcag    5940
ggcttaattt ttaagagcgt caccttcatg gtggtcagtg cgtcctgctg atgtgctcat    6000
tataaccgcc agtggtattt atgtcaacac cgccagagat aatttatcac cgcagatggt    6060
tatctgtgca tgcatttacg ttgaca                                        6086
```

<210> SEQ ID NO 13
<211> LENGTH: 6086
<212> TYPE: DNA
<213> ORGANISM: Artificial Sequence
<220> FEATURE:
<223> OTHER INFORMATION: Plasmid pTAK131

<400> SEQUENCE: 13

```
ccatcgaatg gctgaaatga gctgttgaca attaatcatc cggctcgtat aatgtgtgga     60
attgtgagcg gataacaatt tcacacagga accggttat gagcacaaaa aagaaaccat    120
taacacaaga gcagcttgag gacgcacgtc gccttaaagc aatttatgaa aaaaagaaaa    180
```

-continued

```
atgaacttgg cttatcccag gaatctgtcg cagacaagat ggggatgggg cagtcaggcg      240
ttggtgcttt atttaatggc atcaatgcat taaatgctta taacgccgca ttgcttgcaa      300
aaattctcaa agttagcgtt gaagaattta gcccttcaat cgccagagaa atctacgaga      360
tgtatgaagc ggttagtatg cagccgtcac ttagaagtga gtatgagtac cctgtttttt      420
ctcatgttca ggcagggatg ttctcacctg agcttagaac cttaaccaaa agtgatgcgg      480
agagatgggt aagcacaacc aaaaaagcca gtgattctgc attctggctt gaggttgaag      540
gtaattccat gaccgcacca acaggctcca agccaagctt tcctgacgga atgttaattc      600
tcgttgaccc tgaacaggct gttgagccag gtgatttctg catagccaga cttggggtg      660 atgagtttac cttcaagaaa ctgatcaggg atagcggtca ggtgtttta caaccactaa      720 acccacagta cccaatgatc ccatgcaatg agagttgttc cgttgtgggg aaagttatcg      780
ctagtcagtg gcctgaagag acgtttggct gactgcagca taaataaccc cgctcttaca      840
cattccagcc ctgaaaaagg gcatcaaatt aaaccacacc tatggtgtat gcaaaggaat      900
ttaaatgggt accatgagta aaggagaaga actttcact ggagttgtcc caattcttgt      960
tgaattagat ggcgatgtta atgggcaaaa attctctgtc agtggagagg gtgaaggtga     1020
tgcaacatac ggaaaactta cccttaaatt tatttgcact actgggaagc tacctgttcc     1080
atggccaaca cttgtcacta ctttcggtta tggtgttcaa tgctttgcga gatacccaga     1140
tcatatgaaa cagcatgact ttttcaagag tgccatgccc gaaggttatg tacaggaag     1200 aactatattt tacaaagatg acgggaacta caagacacgt gctgaagtca gtttgaagg     1260 tgataccctt gttaatagaa tcgagttaaa aggtattgat tttaagaag atggaaacat     1320 tcttggacac aaaatggaat acaactataa ctcacataat gtatacatca tggcagacaa     1380
accaaagaat ggaatcaaag ttaacttcaa aattagacac aacattaaag atggaagcgt     1440
tcaattagca gaccattatc aacaaaatac tccaattggc gatggccctg tccttttacc     1500
agacaaccat tacctgtcca cacaatctgc cctttccaaa gatcccaacg aaaagagaga     1560
tcacatgatc cttcttgagt ttgtaacagc tgctgggatt acacatggca tggatgaact     1620
atacaaataa aagctagctt ggctgttttg gcggatgaga aagattttc agcctgatac     1680 agattaaatc agaacgcaga agcggtctga taaaacagaa tttgcctggc ggcagtagcg     1740
cggtggtccc acctgacccc atgccgaact cagaagtgaa acgccgtagc gccgatggta     1800 gtgtgggtc tccccatgcg agagtaggga actgccaggc atcaaataaa acgaaaggct     1860
cagtcgaaag actgggcctt tcgttttatc tgttgtttgt cggtgaacgc tctcctgagt     1920
aggacaaatc cgccgggagc ggatttgaac gttgcgaagc aacggcccgg agggtggcgg     1980
gcaggacgcc cgccataaac tgccaggcat caaattaagc agaaggccat cctgacggat     2040
ggcctttttg cgtttctaca aactcttttt gtttatttt ctaaatacat tcaaatatgt     2100
atccgctcat gagacaataa ccctgataaa tgcttcaata atattgaaaa aggaagagta     2160
tgagtattca acatttccgt gtcgcccta ttccttttt tgcggcattt tgccttcctg     2220
tttttgctca cccagaaacg ctggtgaaag taaagatgc tgaagatcag ttgggtgcac     2280
gagtgggtta catcgaactg gatctcaaca gcggtaagat ccttgagagt tttcgccccg     2340
aagaacgttt tccaatgatg agcactttta aagttctgct atgtggcgcg gtattatccc     2400
gtgttgacgc cgggcaagag caactcggtc gccgcataca ctattctcag aatgacttgg     2460
ttgagtactc accagtcaca gaaaagcatc ttacggatgg catgacagta agagaattat     2520
```

```
gcagtgctgc cataaccatg agtgataaca ctgcggccaa cttacttctg acaacgatcg    2580
gaggaccgaa ggagctaacc gcttttttgc acaacatggg ggatcatgta actcgccttg    2640
atcgttggga accggagctg aatgaagcca taccaaacga cgagcgtgac accacgatgc    2700
ctacagcaat ggcaacaacg ttgcgcaaac tattaactgg cgaactactt actctagctt    2760
cccggcaaca attaatagac tggatggagg cggataaagt tgcaggacca cttctgcgct    2820
cggcccttcc ggctggctgg tttattgctg ataaatctgg agccggtgag cgtgggtctc    2880
gcggtatcat tgcagcactg gggccagatg gtaagccctc ccgtatcgta gttatctaca    2940
cgacggggag tcaggcaact atggatgaac gaaatagaca gatcgctgag ataggtgcct    3000
cactgattaa gcattggtaa ctgtcagacc aagtttactc atatatactt tagattgatt    3060
taaaacttca ttttaattt aaaaggatct aggtgaagat ccttttttgat aatctcatga    3120 ccaaaatccc ttaacgtgag ttttcgttcc actgagcgtc agaccccgta gaaaagatca    3180
aaggatcttc ttgagatcct ttttttctgc gcgtaatctg ctgcttgcaa acaaaaaaac    3240
caccgctacc agcggtggtt tgtttgccgg atcaagagct accaactctt tttccgaagg    3300
taactggctt cagcagagcg cagataccaa atactgtcct tctagtgtag ccgtagttag    3360
gccaccactt caagaactct gtagcaccgc ctacatacct cgctctgcta atcctgttac    3420
cagtggctgc tgccagtggc gataagtcgt gtcttaccgg gttggactca agacgatagt    3480
taccggataa ggcgcagcgg tcgggctgaa cggggggttc gtgcacacag cccagcttgg    3540
agcgaacgac ctacaccgaa ctgagatacc tacagcgtga gctatgagaa agcgccacgc    3600
ttcccgaagg gagaaaggcg gacaggtatc cggtaagcgg cagggtcgga acaggagagc    3660
gcacgaggga gcttccaggg ggaaacgcct ggtatcttta tagtcctgtc gggtttcgcc    3720
acctctgact tgagcgtcga tttttgtgat gctcgtcagg gggcggagc  ctatggaaaa    3780 acgccagcaa cgcggccttt ttacggttcc tggccttttg ctggcctttt gctcacatgt    3840
tctttcctgc gttatcccct gattctgtgg ataaccgtat taccgccttt gagtgagctg    3900
ataccgctcg ccgcagccga acgaccgagc gcagcgagtc agtgagcgag gaagcggaag    3960
agcgagtttg tagaaacgca aaaaggccat ccgtcaggat ggccttctgc ttaatttgat    4020
gcctggcagt ttatggcggg cgtcctgccc gccaccctcc gggccgttgc ttcgcaacgt    4080
tcaaatccgc tcccggcgga tttgtcctac tcaggagagc gttcaccgac aaacaacaga    4140
taaaacgaaa ggcccagtct ttcgactgag cctttcgttt tatttgatgc ctggcagttc    4200
cctactctcg catggggaga ccccacacta ccatcggcgc tacggcgttt cacttctgag    4260
ttcggcatgg ggtcaggtgg gaccaccgcg ctactgccgc caggcaaatt ctgttttatc    4320
agaccgcttc tgcgttctga tttaatctgt atcaggctga aaatcttctc tcatccgcca    4380
aaacagccaa gctataagg cgcgcctcac tgcccgcttt ccagtcggga aacctgtcgt    4440
gccagctgca ttaatgaatc ggccaacgcg cggggagagg cggtttgcgt attgggcgcc    4500
agggtggttt ttcttttcac cagtgagacg ggcaacagct gattgccctt caccgcctgg    4560
ccctgagaga gttgcagcaa gcggtccacg ctggtttgcc ccagcaggcg aaaatcctgt    4620
ttgatggtgg ttaacggcgg gatataacat gagctgtctt cggtatcgtc gtatcccact    4680
accgagatat ccgcaccaac gcgcagcccg gactcggtaa tggcgcgcat tgcgcccagc    4740
gccatctgat cgttggcaac cagcatcgca gtgggaacga tgccctcatt cagcatttgc    4800
atggtttgtt gaaaaccgga catggcactc cagtcgcctt cccgttccgc tatcggctga    4860
atttgattgc gagtgagata tttatgccag ccagccagac gcagacgcgc cgagacagaa    4920
```

-continued

```
cttaatgggc cgctaacag cgcgatttgc tggtgaccca atgcgaccag atgctccacg      4980
cccagtcgcg taccgtcttc atgggagaaa ataatactgt tgatgggtgt ctggtcagag      5040
acatcaagaa ataacgccgg aacattagtg caggcagctt ccacagcaat ggcatcctgg      5100
tcatccagcg gatagttaat gatcagccca ctgacgcgtt gcgcgagaag attgtgcacc      5160
gccgctttac aggcttcgac gccgcttcgt tctaccatcg acaccaccac gctggcaccc      5220
agttgatcgg cgcgagattt aatcgccgcg acaatttgcg acggcgcgtg cagggccaga      5280
ctggaggtgg caacgccaat cagcaacgac tgtttgcccg ccagttgttg tgccacgcgg      5340
ttgggaatgt aattcagctc cgccatcgcc gcttccactt tttcccgcgt tttcgcagaa      5400
acgtggctgg cctggttcac cacgcgggaa acggtctgat aagagacacc ggcatactct      5460
gcgacatcgt ataacgttac tggtttcatg acgtccatcg aaccgtcctt tgcatacacc      5520
ataggtgtgg tttaatttga tgcccttttt cagggctgga atgtgtaaga gcggggttat      5580
ttatgctgtt gttttttttgt tactcgggaa gggctttacc tcttccgcat aaacgcttcc      5640
atcagcgttt atagttaaaa aaatctttcg gaactggttt tgcgcttacc ccaaccaaca      5700
ggggatttgc tgctttccat tgagcctgtt tctctgcgcg acgttcgcgg cggcgtgttt      5760
gtgcatccat ctggattctc ctgtcagtta gctttggtgg tgtgtggcag ttgtagtcct      5820
gaacgaaaac cccccgcgat tggcacattg gcagctaatc cggaatcgca cttacggcca      5880
atgcttcgtt tcgtatcaca cacccccaaag ccttctgctt tgaatgctgc ccttcttcag      5940
ggcttaattt ttaagagcgt caccttcatg gtggtcagtg cgtcctgctg atgtgctcat      6000
tataaccgcc agtggtattt atgtcaacac cgccagagat aatttatcac cgcagatggt      6060
tatctgtgca tgcatttacg ttgaca                                           6086
```

<210> SEQ ID NO 14
<211> LENGTH: 6086
<212> TYPE: DNA
<213> ORGANISM: Artificial Sequence
<220> FEATURE:
<223> OTHER INFORMATION: Plasmid pTAK132

<400> SEQUENCE: 14

```
ccatcgaatg gctgaaatga gctgttgaca attaatcatc cggctcgtat aatgtgtgga       60
attgtgagcg gataacaatt tcacacagga accggttat gagcacaaaa aagaaaccat      120
taacacaaga gcagcttgag gacgcacgtc gccttaaagc aatttatgaa aaaagaaaa      180 atgaacttgg cttatcccag gaatctgtcg cagacaagat ggggatgggg cagtcaggcg      240
ttggtgcttt atttaatggc atcaatgcat taaatgctta taacgccgca ttgcttgcaa      300
aaattctcaa agttagcgtt gaagaattta gcccttcaat cgccagagaa atctacgaga      360
tgtatgaagc ggttagtatg cagccgtcac ttagaagtga gtatgagtac ctgtttttt      420 ctcatgttca ggcagggatg ttctcacctg agcttagaac ctttaccaaa agtgatgcgg      480
agagatgggt aagcacaacc aaaaaagcca gtgattctgc attctggctt gaggttgaag      540
gtaattccat gaccgcacca acaggctcca agccaagctt tcctgacgga atgttaattc      600
tcgttgaccc tgaacaggct gttgagccag gtgattctg catagccaga cttgggggtg      660
atgagtttac cttcaagaaa ctgatcaggg atagcggtca ggtgttttta caaccactaa      720
acccacagta cccaatgatc ccatgcaatg agagttgttc cgttgtgggg aaagttatcg      780
ctagtcagtg gcctgaagag acgtttggct gactgcagca taaataaccc cgctcttaca      840
```

-continued

```
cattccagcc ctgaaaaagg gcatcaaatt aaaccacacc tatggtgtat gcaaaggaat      900
ttaaatgggt accatgagta aaggagaaga acttttcact ggagttgtcc caattcttgt      960
tgaattagat ggcgatgtta atgggcaaaa attctctgtc agtggagagg gtgaaggtga     1020
tgcaacatac ggaaaactta cccttaaatt tatttgcact actgggaagc tacctgttcc     1080
atggccaaca cttgtcacta ctttcggtta tggtgttcaa tgctttgcga gatacccaga     1140
tcatatgaaa cagcatgact ttttcaagag tgccatgccc gaaggttatg tacaggaaag     1200
aactatattt tacaaagatg acgggaacta caagacacgt gctgaagtca agtttgaagg     1260
tgataccctt gttaatagaa tcgagttaaa aggtattgat tttaaagaag atggaaacat     1320
tcttggacac aaaatggaat acaactataa ctcacataat gtatacatca tggcagacaa     1380
accaaagaat ggaatcaaag ttaacttcaa aattagacac aacattaaag atggaagcgt     1440
tcaattagca gaccattatc aacaaaatac tccaattggc gatggccctg tccttttacc     1500
agacaaccat tacctgtcca cacaatctgc cctttccaaa gatcccaacg aaaagagaga     1560
tcacatgatc cttcttgagt ttgtaacagc tgctgggatt acacatggca tggatgaact     1620
atacaaataa aagctagctt ggctgttttg gcggatgaga aagattttc agcctgatac     1680 agattaaatc agaacgcaga agcggtctga taaaacagaa tttgcctggc ggcagtagcg     1740
cggtggtccc acctgacccc atgccgaact cagaagtgaa acgccgtagc gccgatggta     1800
gtgtggggtc tccccatgcg agagtaggga actgccaggc atcaaataaa acgaaaggct     1860
cagtcgaaag actgggcctt tcgttttatc tgttgtttgt cggtgaacgc tctcctgagt     1920
aggacaaatc cgccgggagc ggatttgaac gttgcgaagc aacggcccgg agggtggcgg     1980
gcaggacgcc cgccataaac tgccaggcat caaattaagc agaaggccat cctgacggat     2040
ggcctttttg cgtttctaca aactcttttt gtttattttt ctaaatacat tcaaatatgt     2100
atccgctcat gagacaataa ccctgataaa tgcttcaata atattgaaaa aggaagagta     2160
tgagtattca acatttccgt gtcgccctta ttcccttttt tgcggcatt tgccttcctg     2220 tttttgctca cccagaaacg ctggtgaaag taaaagatgc tgaagatcag ttgggtgcac     2280
gagtgggtta catcgaactg gatctcaaca gcggtaagat ccttgagagt tttcgccccg     2340
aagaacgttt tccaatgatg agcacttta aagttctgct atgtggcgcg gtattatccc     2400
gtgttgacgc cgggcaagag caactcggtc gccgcataca ctattctcag aatgacttgg     2460
ttgagtactc accagtcaca gaaaagcatc ttacggatgg catgacagta agagaattat     2520
gcagtgctgc cataaccatg agtgataaca ctgcggccaa cttacttctg acaacgatcg     2580
gaggaccgaa ggagctaacc gcttttttgc acaacatggg ggatcatgta actcgccttg     2640
atcgttggga accggagctg aatgaagcca taccaaacga cgagcgtgac accacgatgc     2700
ctacagcaat ggcaacaacg ttgcgcaaac tattaactgg cgaactactt actctagctt     2760
cccggcaaca attaatagac tggatggagg cggataaagt tgcaggacca cttctgcgct     2820
cggcccttcc ggctggctgg tttattgctg ataaatctgg agccggtgag cgtgggtctc     2880
gcggtatcat tgcagcactg gggccagatg gtaagccctc ccgtatcgta gttatctaca     2940
cgacggggag tcaggcaact atggatgaac gaaatagaca gatcgctgag ataggtgcct     3000
cactgattaa gcattggtaa ctgtcagacc aagtttactc atatatactt tagattgatt     3060
taaaacttca ttttaattt aaaaggatct aggtgaagat ccttttttgat aatctcatga     3120 ccaaaatccc ttaacgtgag ttttcgttcc actgagcgtc agaccccgta gaaaagatca     3180
aaggatcttc ttgagatcct ttttttctgc gcgtaatctg ctgcttgcaa acaaaaaaac     3240
```

```
caccgctacc agcggtggtt tgtttgccgg atcaagagct accaactctt tttccgaagg   3300
taactggctt cagcagagcg cagataccaa atactgtcct tctagtgtag ccgtagttag   3360
gccaccactt caagaactct gtagcaccgc ctacatacct cgctctgcta atcctgttac   3420
cagtggctgc tgccagtggc gataagtcgt gtcttaccgg gttggactca agacgatagt   3480
taccggataa ggcgcagcgg tcgggctgaa cggggggttc gtgcacacag cccagcttgg   3540
agcgaacgac ctacaccgaa ctgagatacc tacagcgtga gctatgagaa agcgccacgc   3600
ttcccgaagg gagaaaggcg gacaggtatc cggtaagcgg cagggtcgga acaggagagc   3660
gcacgaggga gcttccaggg ggaaacgcct ggtatcttta tagtcctgtc gggtttcgcc   3720
acctctgact tgagcgtcga ttttttgtgat gctcgtcagg ggggcggagc ctatggaaaa   3780
acgccagcaa cgcggccttt ttacggttcc tggccttttg ctggcctttt gctcacatgt   3840
tctttcctgc gttatcccct gattctgtgg ataaccgtat taccgccttt gagtgagctg   3900
ataccgctcg ccgcagccga acgaccgagc gcagcgagtc agtgagcgag gaagcggaag   3960
agcgagtttg tagaaacgca aaaaggccat ccgtcaggat ggccttctgc ttaatttgat   4020
gcctggcagt ttatggcggg cgtcctgccc gccaccctcc gggccgttgc ttcgcaacgt   4080
tcaaatccgc tcccggcgga tttgtcctac tcaggagagc gttcaccgac aaacaacaga   4140
taaaacgaaa ggcccagtct ttcgactgag cctttcgttt tatttgatgc ctggcagttc   4200
cctactctcg catggggaga ccccacacta ccatcggcgc tacggcgttt cacttctgag   4260
ttcggcatgg ggtcaggtgg gaccaccgcg ctactgccgc caggcaaatt ctgttttatc   4320
agaccgcttc tgcgttctga tttaatctgt atcaggctga aaatcttctc tcatccgcca   4380
aaacagccaa gctataaggg cgcgcctcac tgcccgcttt ccagtcggga aacctgtcgt   4440
gccagctgca ttaatgaatc ggccaacgcg cggggagagg cggtttgcgt attgggcgcc   4500
agggtggttt ttcttttcac cagtgagacg ggcaacagct gattgccctt caccgcctgg   4560
ccctgagaga gttgcagcaa gcggtccacg ctggtttgcc ccagcaggcg aaaatcctgt   4620
ttgatggtgg ttaacggcgg gatataacat gagctgtctt cggtatcgtc gtatcccact   4680
accgagatat ccgcaccaac gcgcagcccg gactcggtaa tggcgcgcat tgcgcccagc   4740
gccatctgat cgttggcaac cagcatcgca gtgggaacga tgccctcatt cagcatttgc   4800
atggtttgtt gaaaaccgga catggcactc cagtcgcctt cccgttccgc tatcggctga   4860
atttgattgc gagtgagata tttatgccag ccagccagac gcagacgcgc cgagacagaa   4920
cttaatgggc ccgctaacag cgcgatttgc tggtgaccca atgcgaccag atgctccacg   4980
cccagtcgcg taccgtcttc atgggagaaa ataatactgt tgatgggtgt ctggtcagag   5040
acatcaagaa ataacgccgg aacattagtg caggcagctt ccacagcaat ggcatcctgg   5100
tcatccagcg gatagttaat gatcagccca ctgacgcgtt gcgcgagaag attgtgcacc   5160
gccgctttac aggcttcgac gccgcttcgt tctaccatcg acaccaccac gctggcaccc   5220
agttgatcgg cgcgagattt aatcgccgcg acaatttgcg acggcgcgtg cagggccaga   5280
ctggaggtgg caacgccaat cagcaacgac tgtttgcccg ccagttgttg tgccacgcgg   5340
ttgggaatgt aattcagctc cgccatcgcc gcttccactt tttcccgcgt tttcgcagaa   5400
acgtggctgg cctggttcac cacgcgggaa acggtctgat aagagacacc ggcatactct   5460
gcgacatcgt ataacgttac tggtttcatg acgtccatcc ggccgtcctt tgcatacacc   5520
ataggtgtgg tttaatttga tgcccttttt cagggctgga atgtgtaaga gcggggttat   5580
```

-continued

```
ttatgctgtt gttttttttgt tactcgggaa gggctttacc tcttccgcat aaacgcttcc    5640
atcagcgttt atagttaaaa aaatctttcg gaactggttt tgcgcttacc ccaaccaaca    5700
ggggatttgc tgcttttccat tgagcctgtt tctctgcgcg acgttcgcgg cggcgtgttt    5760
gtgcatccat ctggattctc ctgtcagtta gctttggtgg tgtgtggcag ttgtagtcct    5820
gaacgaaaac cccccgcgat tggcacattg gcagctaatc cggaatcgca cttacggcca    5880
atgcttcgtt tcgtatcaca caccccaaag ccttctgctt tgaatgctgc ccttcttcag    5940
ggcttaattt ttaagagcgt caccttcatg gtggtcagtg cgtcctgctg atgtgctcat    6000
tataaccgcc agtggtattt atgtcaacac cgccagagat aatttatcac cgcagatggt    6060
tatctgtgca tgcatttacg ttgaca                                        6086
```

<210> SEQ ID NO 15
<211> LENGTH: 6088
<212> TYPE: DNA
<213> ORGANISM: Artificial Sequence
<220> FEATURE:
<223> OTHER INFORMATION: Plasmid pTAK130

<400> SEQUENCE: 15

```
ccatcgaatg gctgaaatga gctgttgaca attaatcatc cggctcgtat aatgtgtgga     60
attgtgagcg gataacaatt tcacacagga accggttat gagcacaaaa aagaaaccat    120
taacacaaga gcagcttgag gacgcacgtc gccttaaagc aatttatgaa aaaagaaaa    180 atgaacttgg cttatcccag gaatctgtcg cagacaagat ggggatgggg cagtcaggcg    240
ttggtgcttt atttaatggc atcaatgcat taaatgctta taacgccgca ttgcttgcaa    300
aaattctcaa agttagcgtt gaagaattta gcccttcaat cgccagagaa atctacgaga    360
tgtatgaagc ggttagtatg cagccgtcac ttagaagtga gtatgagtac cctgttttt    420 ctcatgttca ggcagggatg ttctcacctg agcttagaac cttaccaaa agtgatgcgg    480 agagatgggt aagcacaacc aaaaaagcca gtgattctgc attctggctt gaggttgaag    540
gtaattccat gaccgcacca acaggctcca agccaagctt tcctgacgga atgttaattc    600
tcgttgaccc tgaacaggct gttgagccag gtgatttctg catagccaga cttggggtg    660 atgagtttac cttcaagaaa ctgatcaggg atagcggtca ggtgttttta caaccactaa    720
acccacagta cccaatgatc ccatgcaatg agagttgttc cgttgtgggg aaagttatcg    780
ctagtcagtg gcctgaagag acgtttggct gactgcagca taaataaccc cgctcttaca    840
cattccagcc ctgaaaaagg gcatcaaatt aaaccacacc tatggtgtat gcaaaggaat    900
ttaaatgggt accatgagta aaggagaaga acttttcact ggagttgtcc caattcttgt    960
tgaattagat ggcgatgtta atgggcaaaa attctctgtc agtggagagg gtgaaggtga   1020
tgcaacatac ggaaaactta cccttaaatt tatttgcact actgggaagc tacctgttcc   1080
atggccaaca cttgtcacta cttttcggtta tggtgttcaa tgctttgcga tacccagat   1140 tcatatgaaa cagcatgact ttttcaagag tgccatgccc gaaggttatg tacaggaaag   1200
aactatattt tacaaagatg acgggaacta caagacacgt gctgaagtca gtttgaagg   1260 tgataccctt gttaatagaa tcgagttaaa aggtattgat tttaagaag atggaaacat   1320 tcttggacac aaaatggaat acaactataa ctcacataat gtatacatca tggcagacaa   1380
accaaagaat ggaatcaaag ttaacttcaa aattagacac aacattaaag atggaagcgt   1440
tcaattagca gaccattatc aacaaaatac tccaattggc gatggccctg tccttttacc   1500
agacaaccat tacctgtcca cacaatctgc cctttccaaa gatcccaacg aaaagagaga   1560
```

```
tcacatgatc cttcttgagt ttgtaacagc tgctgggatt acacatggca tggatgaact    1620
atacaaataa aagctagctt ggctgttttg gcggatgaga aagattttc agcctgatac     1680 agattaaatc agaacgcaga agcggtctga taaaacagaa tttgcctggc ggcagtagcg    1740
cggtggtccc acctgacccc atgccgaact cagaagtgaa acgccgtagc gccgatggta    1800
gtgtggggtc tccccatgcg agagtaggga actgccaggc atcaaataaa acgaaaggct    1860
cagtcgaaag actgggcctt tcgttttatc tgttgtttgt cggtgaacgc tctcctgagt    1920
aggacaaatc cgccgggagc ggatttgaac gttgcgaagc aacggcccgg agggtggcgg    1980
gcaggacgcc cgccataaac tgccaggcat caaattaagc agaaggccat cctgacggat    2040
ggcctttttg cgtttctaca aactctttt gtttattttt ctaaatacat tcaaatatgt     2100
atccgctcat gagacaataa ccctgataaa tgcttcaata atattgaaaa aggaagagta    2160
tgagtattca acatttccgt gtcgccctta ttcccttttt tgcggcattt tgccttcctg    2220 ttttgctca cccagaaacg ctggtgaaag taaaagatgc tgaagatcag ttgggtgcac     2280
gagtgggtta catcgaactg gatctcaaca gcggtaagat ccttgagagt tttcgccccg    2340
aagaacgttt tccaatgatg agcacttta aagttctgct atgtggcgcg gtattatccc     2400
gtgttgacgc cgggcaagag caactcggtc gccgcataca ctattctcag aatgacttgg    2460
ttgagtactc accagtcaca gaaaagcatc ttacggatgg catgacagta agagaattat    2520
gcagtgctgc cataaccatg agtgataaca ctgcggccaa cttacttctg acaacgatcg    2580
gaggaccgaa ggagctaacc gcttttttgc acaacatggg ggatcatgta actcgccttg    2640
atcgttggga accggagctg aatgaagcca taccaaacga cgagcgtgac accacgatgc    2700
ctacagcaat ggcaacaacg ttgcgcaaac tattaactgg cgaactactt actctagctt    2760
cccggcaaca attaatagac tggatggagg cggataaagt tgcaggacca cttctgcgct    2820
cggcccttcc ggctggctgg tttattgctg ataaatctgg agccggtgag cgtgggtctc    2880
gcggtatcat tgcagcactg gggccagatg gtaagccctc ccgtatcgta gttatctaca    2940
cgacggggag tcaggcaact atggatgaac gaaatagaca gatcgctgag ataggtgcct    3000
cactgattaa gcattggtaa ctgtcagacc aagtttactc atatatactt tagattgatt    3060
taaaacttca ttttaatt aaaggatct aggtgaagat cctttttgat aatctcatga       3120
ccaaaatccc ttaacgtgag ttttcgttcc actgagcgtc agaccccgta gaaaagatca    3180
aaggatcttc ttgagatcct ttttttctgc gcgtaatctg ctgcttgcaa acaaaaaaac    3240
caccgctacc agcggtggtt tgtttgccgg atcaagagct accaactctt tttccgaagg    3300
taactggctt cagcagagcg cagataccaa atactgtcct tctagtgtag ccgtagttag    3360
gccaccactt caagaactct gtagcaccgc ctacatacct cgctctgcta atcctgttac    3420
cagtggctgc tgccagtggc gataagtcgt gtcttaccgg gttggactca agacgatagt    3480
taccggataa ggcgcagcgg tcgggctgaa cggggggttc gtgcacacag cccagcttgg    3540
agcgaacgac ctacaccgaa ctgagatacc tacagcgtga gctatgagaa agcgccacgc    3600
ttcccgaagg gagaaaggcg gacaggtatc cggtaagcgg cagggtcgga acaggagagc    3660
gcacgaggga gcttccaggg ggaaacgcct ggtatcttta tagtcctgtc gggtttcgcc    3720
acctctgact tgagcgtcga ttttgtgat gctcgtcagg gggcggagc ctatggaaaa      3780 acgccagcaa cgcggccttt ttacggttcc tggccttttg ctggccttt gctcacatgt     3840 tctttcctgc gttatcccct gattctgtgg ataaccgtat taccgccttt gagtgagctg    3900
```

-continued

```
ataccgctcg ccgcagccga acgaccgagc gcagcgagtc agtgagcgag gaagcggaag      3960
agcgagtttg tagaaacgca aaaaggccat ccgtcaggat ggccttctgc ttaatttgat      4020
gcctggcagt ttatggcggg cgtcctgccc gccacccctcc gggccgttgc ttcgcaacgt     4080
tcaaatccgc tcccggcgga tttgtcctac tcaggagagc gttcaccgac aaacaacaga     4140
taaaacgaaa ggcccagtct ttcgactgag cctttcgttt tatttgatgc ctggcagttc      4200
cctactctcg catggggaga ccccacacta ccatcggcgc tacggcgttt cacttctgag     4260
ttcggcatgg ggtcaggtgg gaccaccgcg ctactgccgc caggcaaatt ctgttttatc     4320
agaccgcttc tgcgttctga tttaatctgt atcaggctga aaatcttctc tcatccgcca     4380
aaacagccaa gcttataagg cgcgcctcac tgcccgcttt ccagtcggga aacctgtcgt     4440
gccagctgca ttaatgaatc ggccaacgcg cggggagagg cggtttgcgt attgggcgcc     4500
agggtggttt ttcttttcac cagtgagacg ggcaacagct gattgcccctt caccgcctgg    4560 ccctgagaga gttgcagcaa gcggtccacg ctggtttgcc ccagcaggcg aaaatcctgt     4620
ttgatggtgg ttaacggcgg gatataacat gagctgtctt cggtatcgtc gtatcccact    4680
accgagatat ccgcaccaac gcgcagcccg gactcggtaa tggcgcgcat tgcgcccagc   4740
gccatctgat cgttggcaac cagcatcgca gtgggaacga tgccctcatt cagcatttgc    4800
atggtttgtt gaaaaccgga catggcactc cagtcgcctt cccgttccgc tatcggctga    4860
atttgattgc gagtgagata tttatgccag ccagccagac gcagacgcgc cgagacagaa   4920
cttaatgggc ccgctaacag cgcgatttgc tggtgaccca atgcgaccag atgctccacg   4980
cccagtcgcg taccgtcttc atgggagaaa ataatactgt tgatgggtgt ctggtcagag   5040
acatcaagaa ataacgccgg aacattagtg caggcagctt ccacagcaat ggcatcctgg   5100
tcatccagcg gatagttaat gatcagccca ctgacgcgtt gcgcgagaag attgtgcacc   5160
gccgctttac aggcttcgac gccgcttcgt tctaccatcg acaccaccac gctggcaccc    5220
agttgatcgg cgcgagattt aatcgccgcg acaatttgcg acggcgcgtg cagggccaga   5280
ctggaggtgg caacgccaat cagcaacgac tgtttgcccg ccagttgttg tgccacgcgg    5340
ttgggaatgt aattcagctc cgccatcgcc gcttccactt tttcccgcgt tttcgcagaa    5400
acgtggctgg cctggttcac cacgcgggaa acggtctgat aagagacacc ggcatactct    5460
gcgacatcgt ataacgttac tggtttcatg acgtccatcg aggcctttcc tttgcataca    5520
ccataggtgt ggtttaattt gatgcccttt tcagggctg gaatgtgtaa gagcggggtt     5580
atttatgctg ttgttttttt gttactcggg aagggcttta cctcttccgc ataaacgctt    5640
ccatcagcgt ttatagttaa aaaaatcttt cggaactggt tttgcgctta ccccaaccaa   5700 cagggggattt gctgctttcc attgagcctg tttctctgcg cgacgttcgc ggcggcgtgt   5760
ttgtgcatcc atctggattc tcctgtcagt tagctttggt ggtgtgtggc agttgtagtc   5820
ctgaacgaaa acccccgcg attggcacat tggcagctaa tccggaatcg cacttacggc   5880
caatgcttcg tttcgtatca cacacccaa agccttctgc tttgaatgct gcccttcttc    5940
agggcttaat ttttaagagc gtcaccttca tggtggtcag tgcgtcctgc tgatgtgctc   6000
attataaccg ccagtggtat ttatgtcaac accgccagag ataatttatc accgcagatg   6060
gttatctgtg catgcatta cgttgaca                                        6088
```

<210> SEQ ID NO 16
<211> LENGTH: 5522
<212> TYPE: DNA
<213> ORGANISM: Artificial Sequence
<220> FEATURE:
<223> OTHER INFORMATION: Plasmid pIKE105

<400> SEQUENCE: 16

| | | | | | |
|---|---|---|---|---|---:|
| ccatcgaatg | gctgaaatga | gctgttgaca | attaatcatc | cggctcgtat aatgtgtgga | 60 |
| attgtgagcg | gataacaatt | tcacacagga | accggttat | ggaattcatg tctagattag | 120 |
| ataaaagtaa | agtgattaac | agcgcattag | agctgcttaa | tgaggtcgga atcgaaggtt | 180 |
| taacaacccg | taaactcgcc | cagaagctag | gtgtagagca | gcctacattg tattggcatg | 240 |
| taaaaaataa | gcgggctttg | ctcgacgcct | tagccattga | gatgttagat aggcaccata | 300 |
| ctcacttttg | ccctttagaa | ggggaaagct | ggcaagattt | tttacgtaat aacgctaaaa | 360 |
| gttttagatg | tgctttacta | agtcatcgcg | atggagcaaa | agtacattta ggtacacggc | 420 |
| ctacagaaaa | acagtatgaa | actctcgaaa | atcaattagc | cttttatgc caacaaggtt | 480 |
| tttcactaga | gaatgcatta | tatgcactca | gcgctgtggg | gcattttact ttaggttgcg | 540 |
| tattggaaga | tcaagagcat | caagtcgcta | agaagaaag | ggaaacacct actactgata | 600 |
| gtatgccgcc | attattacga | caagctatcg | aattatttga | tcaccaaggt gcagagccag | 660 |
| ccttcttatt | cggccttgaa | ttgatcatat | gcggattaga | aaaacaactt aaatgtgaaa | 720 |
| gtgggtctta | actgcagcat | aaataacccc | gctcttacac | attccagccc tgaaaagggg | 780 |
| catcaaatta | aaccacacct | atggtgtatg | caaaggaatt | taaatgggta ccatgagtaa | 840 |
| aggagaagaa | cttttcactg | gagttgtccc | aattcttgtt | gaattagatg gcgatgttaa | 900 |
| tgggcaaaaa | ttctctgtca | gtggagaggg | tgaaggtgat | gcaacatacg gaaaacttac | 960 |
| ccttaaattt | atttgcacta | ctgggaagct | acctgttcca | tggccaacac ttgtcactac | 1020 |
| tttcggttat | ggtgttcaat | gctttgcgag | atacccagat | catatgaaac agcatgactt | 1080 |
| tttcaagagt | gccatgcccg | aaggttatgt | acaggaaaga | actatatttt acaaagatga | 1140 |
| cgggaactac | aagacacgtg | ctgaagtcaa | gtttgaaggt | gatacccttg ttaatagaat | 1200 |
| cgagttaaaa | ggtattgatt | ttaaagaaga | tggaaacatt | cttggacaca aaatggaata | 1260 |
| caactataac | tcacataatg | tatacatcat | ggcagacaaa | ccaaagaatg gaatcaaagt | 1320 |
| taacttcaaa | attagacaca | acattaaaga | tggaagcgtt | caattagcag accattatca | 1380 |
| acaaaatact | ccaattggcg | atggccctgt | ccttttacca | gacaaccatt acctgtccac | 1440 |
| acaatctgcc | ctttccaaag | atcccaacga | aaagagagat | cacatgatcc ttcttgagtt | 1500 |
| tgtaacagct | gctgggatta | cacatggcat | ggatgaacta | tacaaataaa agctagcttg | 1560 |
| gctgttttgg | cggatgagag | aagattttca | gcctgataca | gattaaatca gaacgcagaa | 1620 |
| gcggtctgat | aaaacagaat | ttgcctggcg | gcagtagcgc | ggtggtccca cctgacccca | 1680 |
| tgccgaactc | agaagtgaaa | cgccgtagcg | ccgatggtag | tgtggggtct ccccatgcga | 1740 |
| gagtagggaa | ctgccaggca | tcaaataaaa | cgaaaggctc | agtcgaaaga ctgggccttt | 1800 |
| cgttttatct | gttgtttgtc | ggtgaacgct | ctcctgagta | ggacaaatcc gccgggagcg | 1860 |
| gatttgaacg | ttgcgaagca | acggcccgga | gggtggcggg | caggacgccc gccataaact | 1920 |
| gccaggcatc | aaattaagca | gaaggccatc | ctgacggatg | gcctttttgc gtttctacaa | 1980 |
| actctttttg | tttatttttc | taaatacatt | caaatatgta | tccgctcatg agacaataac | 2040 |
| cctgataaat | gcttcaataa | tattgaaaaa | ggaagagtat | gagtattcaa catttccgtg | 2100 |
| tcgcccttat | tccctttttt | gcggcatttt | gccttcctgt | ttttgctcac ccagaaacgc | 2160 |
| tggtgaaagt | aaaagatgct | gaagatcagt | tgggtgcacg | agtgggttac atcgaactgg | 2220 |

```
atctcaacag cggtaagatc cttgagagtt ttcgccccga agaacgtttt ccaatgatga    2280 gcactttttaa agttctgcta tgtggcgcgg tattatcccg tgttgacgcc gggcaagagc   2340
aactcggtcg ccgcatacac tattctcaga atgacttggt tgagtactca ccagtcacag   2400
aaaagcatct tacggatggc atgacagtaa gagaattatg cagtgctgcc ataaccatga   2460
gtgataacac tgcggccaac ttacttctga caacgatcgg aggaccgaag gagctaaccg   2520
cttttttgca acacatgggg gatcatgtaa ctcgccttga tcgttgggaa ccggagctga   2580
atgaagccat accaaacgac gagcgtgaca ccacgatgcc tacagcaatg caacaacgt    2640 tgcgcaaact attaactggc gaactactta ctctagcttc ccggcaacaa ttaatagact   2700
ggatggaggc ggataaagtt gcaggaccac ttctgcgctc ggcccttccg gctggctggt   2760
ttattgctga taaatctgga gccggtgagc gtgggtctcg cggtatcatt gcagcactgg   2820
ggccagatgg taagccctcc cgtatcgtag ttatctacac gacggggagt caggcaacta   2880
tggatgaacg aaatagacag atcgctgaga taggtgcctc actgattaag cattggtaac   2940
tgtcagacca gtttactca tatatacttt agattgattt aaaacttcat ttttaattta    3000
aaaggatcta ggtgaagatc ttttttgata atctcatgac caaaatccct taacgtgagt   3060
tttcgttcca ctgagcgtca gaccccgtag aaaagatcaa aggatcttct tgagatcctt   3120
tttttctgcg cgtaatctgc tgcttgcaaa caaaaaaacc accgctacca gcggtggttt   3180
gtttgccgga tcaagagcta ccaactcttt ttccgaaggt aactggcttc agcagagcgc   3240
agataccaaa tactgtcctt ctagtgtagc cgtagttagg ccaccacttc aagaactctg   3300
tagcaccgcc tacatacctc gctctgctaa tcctgttacc agtggctgct gccagtggcg   3360
ataagtcgtg tcttaccggg ttggactcaa gacgatagtt accggataag cgcagcggt    3420 cgggctgaac ggggggttcg tgcacacagc ccagcttgga gcgaacgacc tacaccgaac   3480
tgagatacct acagcgtgag ctatgagaaa gcgccacgct tcccgaaggg agaaaggcgg   3540
acaggtatcc ggtaagcggc agggtcggaa caggagagcg cacgagggag cttccagggg   3600
gaaacgcctg gtatctttat agtcctgtcg ggtttcgcca cctctgactt gagcgtcgat   3660
ttttgtgatg ctcgtcaggg gggcggagcc tatggaaaaa cgccagcaac gcggcctttt   3720
tacggttcct ggccttttgc tggccttttg ctcacatgtt ctttcctgcg ttatcccctg   3780
attctgtgga taaccgtatt accgcctttg agtgagctga taccgctcgc cgcagccgaa   3840
cgaccgagcg cagcgagtca gtgagcgagg aagcggaaga gcgagtttgt agaaacgcaa   3900
aaaggccatc cgtcaggatg gccttctgct taatttgatg cctggcagtt tatggcgggc   3960
gtcctgcccg ccaccctccg ggccgttgct tcgcaacgtt caaatccgct cccggcggat   4020
ttgtcctact caggagagcg ttcaccgaca acaacagat aaaacgaaag gcccagtctt    4080
tcgactgagc ctttcgtttt atttgatgcc tggcagttcc ctactctcgc atgggagac    4140 cccacactac catcggcgct acggcgtttc acttctgagt tcggcatggg gtcaggtggg   4200
accaccgcgc tactgccgcc aggcaaattc tgttttatca gaccgcttct gcgttctgat   4260
ttaatctgta tcaggctgaa aatcttctct catccgccaa acagccaag cttataaggc     4320 gcgcctcact gcccgctttc cagtcgggaa acctgtcgtg ccagctgcat taatgaatcg   4380
gccaacgcgc ggggagaggc ggtttgcgta ttgggcgcca gggtggtttt cttttcacc    4440 agtgagacgg gcaacagctg attgcccttc accgcctggc cctgagagag ttgcagcaag   4500
cggtccacgc tggtttgccc cagcaggcga aaatcctgtt tgatggtggt taacggcggg   4560
atataacatg agctgtcttc ggtatcgtcg tatcccacta ccgagatatc cgcaccaacg   4620
```

```
cgcagcccgg actcggtaat ggcgcgcatt gcgcccagcg ccatctgatc gttggcaacc      4680
agcatcgcag tgggaacgat gccctcattc agcatttgca tggtttgttg aaaaccggac      4740
atggcactcc agtcgccttc ccgttccgct atcggctgaa tttgattgcg agtgagatat      4800
ttatgccagc cagccagacg cagacgcgcc gagacagaac ttaatgggcc cgctaacagc      4860
gcgatttgct ggtgacccaa tgcgaccaga tgctccacgc ccagtcgcgt accgtcttca      4920
tgggagaaaa taatactgtt gatgggtgtc tggtcagaga catcaagaaa taacgccgga      4980
acattagtgc aggcagcttc cacagcaatg catcctggt catccagcgg atagttaatg       5040
atcagcccac tgacgcgttg cgcgagaaga ttgtgcaccg ccgctttaca ggcttcgacg      5100
ccgcttcgtt ctaccatcga caccaccacg ctggcaccca gttgatcggc gcgagattta      5160
atcgccgcga caatttgcga cggcgcgtgc agggccagac tggaggtggc aacgccaatc      5220
agcaacgact gtttgcccgc cagttgttgt gccacgcgt tgggaatgta attcagctcc       5280
gccatcgccg cttccacttt tcccgcgtt ttcgcagaaa cgtggctggc ctggttcacc       5340
acgcgggaaa cggtctgata agagacaccg gcatactctg cgacatcgta taacgttact     5400
ggtttcatga cgtccatttt tttcctcctg gtcagtgcgt cctgctgatg tgctcagtat      5460
ctctatcact gatagggatg tcaatctcta tcactgatag ggagcatgca tttacgttga     5520
ca                                                                    5522

<210> SEQ ID NO 17
<211> LENGTH: 5525
<212> TYPE: DNA
<213> ORGANISM: Artificial Sequence
<220> FEATURE:
<223> OTHER INFORMATION: Plasmid pIKE107

<400> SEQUENCE: 17
ccatcgaatg gctgaaatga gctgttgaca attaatcatc cggctcgtat aatgtgtgga       60
attgtgagcg gataacaatt tcacacagga accggttat ggaattcatg tctagattag       120 ataaagtaa agtgattaac agcgcattag agctgcttaa tgaggtcgga atcgaaggtt       180
taacaacccg taaactcgcc cagaagctag gtgtagagca gcctacattg tattggcatg       240 taaaaataa gcgggctttg ctcgacgcct tagccattga gatgttagat aggcaccata       300
ctcacttttg ccctttagaa ggggaaagct ggcaagattt tttacgtaat aacgctaaaa       360
gttttagatg tgctttacta agtcatcgcg atggagcaaa agtacattta ggtacacggc       420
ctacagaaaa acagtatgaa actctcgaaa atcaattagc cttttatgc caacaaggtt       480 tttcactaga gaatgcatta tatgcactca gcgctgtggg gcattttact ttaggttgcg       540
tattggaaga tcaagagcat caagtcgcta agaagaaag ggaaacacct actactgata       600
gtatgccgcc attattacga caagctatcg aattatttga tcaccaaggt gcagagccag       660
ccttcttatt cggccttgaa ttgatcatat gcggattaga aaacaacttt aaatgtgaaa       720
gtgggtctta actgcagcat aaataacccc gctcttacac attccagccc tgaaaaaggg      780
catcaaatta aaccacacct atggtgtatg caaaggaatt taaatgggta ccatgagtaa      840
aggagaagaa ctttcactg gagttgtccc aattcttgtt gaattagatg gcgatgttaa      900
tgggcaaaaa ttctctgtca gtggagaggg tgaaggtgat gcaacatacg gaaaacttac      960
ccttaaattt atttgcacta ctgggaagct acctgttcca tggccaacac ttgtcactac     1020
tttcggttat ggtgttcaat gctttgcgag atacccagat catatgaaac agcatgactt     1080
```

-continued

```
tttcaagagt gccatgcccg aaggttatgt acaggaaaga actatatttt acaaagatga    1140
cgggaactac aagacacgtg ctgaagtcaa gtttgaaggt gatacccttg ttaatagaat    1200
cgagttaaaa ggtattgatt ttaaagaaga tggaaacatt cttggacaca aaatggaata    1260
caactataac tcacataatg tatacatcat ggcagacaaa ccaaagaatg gaatcaaagt    1320
taacttcaaa attagacaca acattaaaga tggaagcgtt caattagcag accattatca    1380
acaaaatact ccaattggcg atggccctgt ccttttacca gacaaccatt acctgtccac    1440
acaatctgcc ctttccaaag atcccaacga aaagagagat cacatgatcc ttcttgagtt    1500
tgtaacagct gctgggatta cacatggcat ggatgaacta tacaaataaa agctagcttg    1560
gctgttttgg cggatgagag aagattttca gcctgataca gattaaatca gaacgcagaa    1620
gcggtctgat aaaacagaat ttgcctggcg cagtagcgc ggtggtccca cctgacccca     1680
tgccgaactc agaagtgaaa cgccgtagcg ccgatggtag tgtggggtct ccccatgcga    1740
gagtagggaa ctgccaggca tcaaataaaa cgaaaggctc agtcgaaaga ctgggccttt    1800
cgttttatct gttgtttgtc ggtgaacgct ctcctgagta ggacaaatcc gccgggagcg    1860
gatttgaacg ttgcgaagca acggcccgga gggtggcggg caggacgccc gccataaact    1920
gccaggcatc aaattaagca gaaggccatc ctgacggatg ccttttttgc gtttctacaa    1980 actcttttg tttattttc taaatacatt caaatatgta tccgctcatg agacaataac     2040
cctgataaat gcttcaataa tattgaaaaa ggaagagtat gagtattcaa catttccgtg    2100
tcgcccttat tcccttttt gcggcatttt gccttcctgt ttttgctcac ccagaaacgc    2160
tggtgaaagt aaaagatgct gaagatcagt tgggtgcacg agtgggttac atcgaactgg    2220
atctcaacag cggtaagatc cttgagagtt ttcgccccga agaacgtttt ccaatgatga    2280 gcactttaa agttctgcta tgtggcgcgg tattatcccg tgttgacgcc gggcaagagc    2340
aactcggtcg ccgcatacac tattctcaga atgacttggt tgagtactca ccagtcacag    2400
aaaagcatct tacggatggc atgacagtaa gagaattatg cagtgctgcc ataaccatga    2460
gtgataacac tgcggccaac ttacttctga caacgatcgg aggaccgaag gagctaaccg    2520
cttttttgca acatgggg gatcatgtaa ctcgccttga tcgttgggaa ccggagctga     2580
atgaagccat accaaacgac gagcgtgaca ccacgatgcc tacagcaatg gcaacaacgt    2640
tgcgcaaact attaactggc gaactactta ctctagcttc ccggcaacaa ttaatagact    2700
ggatggaggc ggataaagtt gcaggaccac ttctgcgctc ggcccttccg gctggctggt    2760
ttattgctga taaatctgga gccggtgagc gtgggtctcg cggtatcatt gcagcactgg    2820
ggccagatgg taagccctcc cgtatcgtag ttatctacac gacggggagt caggcaacta    2880
tggatgaacg aaatagacag atcgctgaga taggtgcctc actgattaag cattggtaac    2940
tgtcagacca agtttactca tatatacttt agattgattt aaaacttcat ttttaattta    3000
aaaggatcta ggtgaagatc cttttttgata atctcatgac caaaatccct aacgtgagt    3060 tttcgttcca ctgagcgtca gaccccgtag aaaagatcaa aggatcttct tgagatcctt    3120
tttttctgcg cgtaatctgc tgcttgcaaa caaaaaaacc accgctacca gcggtggttt    3180
gtttgccgga tcaagagcta ccaactcttt ttccgaaggt aactggcttc agcagagcgc    3240
agataccaaa tactgtcctt ctagtgtagc cgtagttagg ccaccacttc aagaactctg    3300
tagcaccgcc tacatacctc gctctgctaa tcctgttacc agtggctgct gccagtggcg    3360
ataagtcgtg tcttaccggg ttggactcaa gacgatagtt accggataag cgcagcggt    3420 cgggctgaac ggggggttcg tgcacacagc ccagcttgga gcgaacgacc tacaccgaac    3480
```

-continued

```
tgagatacct acagcgtgag ctatgagaaa gcgccacgct tcccgaaggg agaaaggcgg      3540
acaggtatcc ggtaagcggc agggtcggaa caggagagcg cacgagggag cttccagggg      3600
gaaacgcctg gtatctttat agtcctgtcg ggtttcgcca cctctgactt gagcgtcgat      3660
ttttgtgatg ctcgtcaggg gggcggagcc tatggaaaaa cgccagcaac gcggcctttt      3720
tacggttcct ggccttttgc tggccttttg ctcacatgtt ctttcctgcg ttatcccctg      3780
attctgtgga taaccgtatt accgcctttg agtgagctga taccgctcgc cgcagccgaa      3840
cgaccgagcg cagcgagtca gtgagcgagg aagcggaaga gcgagtttgt agaaacgcaa      3900
aaaggccatc cgtcaggatg gccttctgct taatttgatg cctggcagtt tatggcgggc      3960
gtcctgcccg ccaccctccg ggccgttgct tcgcaacgtt caaatccgct cccggcggat      4020
ttgtcctact caggagagcg ttcaccgaca acaacagat aaaacgaaag gcccagtctt      4080
tcgactgagc ctttcgtttt atttgatgcc tggcagttcc ctactctcgc atgggagac      4140 cccacactac catcggcgct acggcgtttc acttctgagt tcggcatggg gtcaggtggg      4200
accaccgcgc tactgccgcc aggcaaattc tgttttatca gaccgcttct gcgttctgat      4260
ttaatctgta tcaggctgaa aatcttctct catccgccaa aacagccaag cttataaggc      4320
gcgcctcact gcccgctttc cagtcgggaa acctgtcgtg ccagctgcat taatgaatcg      4380
gccaacgcgc ggggagaggc ggtttgcgta ttgggcgcca gggtggtttt tcttttcacc      4440
agtgagacgg gcaacagctg attgcccttc accgcctggc cctgagagag ttgcagcaag      4500
cggtccacgc tggtttgccc cagcaggcga aaatcctgtt tgatggtggt taacggcggg      4560
atataacatg agctgtcttc ggtatcgtcg tatcccacta ccgagatatc cgcaccaacg      4620
cgcagcccgg actcggtaat ggcgcgcatt gcgcccagcg ccatctgatc gttggcaacc      4680
agcatcgcag tgggaacgat gccctcattc agcatttgca tggtttgttg aaaaccggac      4740
atggcactcc agtcgccttc ccgttccgct atcggctgaa tttgattgcg agtgagatat      4800
ttatgccagc cagccagacg cagacgcgcc gagacagaac ttaatgggcc cgctaacagc      4860
gcgatttgct ggtgacccaa tgcgaccaga tgctccacgc ccagtcgcgt accgtcttca      4920
tgggagaaaa taatactgtt gatgggtgtc tggtcagaga catcaagaaa taacgccgga      4980
acattagtgc aggcagcttc cacagcaatg gcatcctggt catccagcgg atagttaatg      5040
atcagcccac tgacgcgttg cgcgagaaga ttgtgcaccg ccgctttaca ggcttcgacg      5100
ccgcttcgtt ctaccatcga caccaccacg ctggcaccca gttgatcggc gcgagattta      5160
atcgccgcga caatttgcga cggcgcgtgc agggccagac tggaggtggc aacgccaatc      5220
agcaacgact gtttgcccgc cagttgttgt gccacgcggt tgggaatgta attcagctcc      5280
gccatcgccg cttccacttt ttcccgcgtt ttcgcagaaa cgtggctggc ctggttcacc      5340
acgcgggaaa cggtctgata agagacaccg gcatactctg cgacatcgta taacgttact      5400
ggtttcatga cgtccatggt ctgtttcctc ctggtcagtg cgtcctgctg atgtgctcag      5460
tatctctatc actgataggg atgtcaatct ctatcactga tagggagcat gcatttacgt      5520
tgaca                                                                 5525
```